(12) United States Patent
Gockel et al.

(10) Patent No.: US 10,513,498 B2
(45) Date of Patent: Dec. 24, 2019

(54) PROCESS FOR PREPARING PYRAZOLES

(71) Applicant: BASF SE, Ludwigshafen (DE)

(72) Inventors: Birgit Gockel, Ludwigshafen (DE); Daniel Saelinger, Ludwigshafen (DE); Sebastian Soergel, Ludwigshafen (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/292,773

(22) Filed: Mar. 5, 2019

(65) Prior Publication Data

US 2019/0194141 A1 Jun. 27, 2019

Related U.S. Application Data

(62) Division of application No. 15/329,104, filed as application No. PCT/EP2015/067507 on Jul. 30, 2015.

(30) Foreign Application Priority Data

Jul. 31, 2014 (EP) .................................... 14179249

(51) Int. Cl.
*C07D 231/14* (2006.01)
*C07D 401/12* (2006.01)
*C07D 405/06* (2006.01)
*C07D 403/12* (2006.01)

(52) U.S. Cl.
CPC ......... *C07D 231/14* (2013.01); *C07D 401/12* (2013.01); *C07D 403/12* (2013.01); *C07D 405/06* (2013.01)

(58) Field of Classification Search
CPC ............................ C07D 231/14; C07D 401/12
See application file for complete search history.

(56) References Cited

U.S. PATENT DOCUMENTS

| 4,728,355 | A | 3/1988 | Henrie |
| 6,140,332 | A | 10/2000 | Traxler et al. |
| 6,258,822 | B1 | 7/2001 | Geyer et al. |
| 8,987,461 | B2 | 3/2015 | Nie et al. |
| 2010/0305124 | A1 | 12/2010 | Fusslein et al. |
| 2013/0324547 | A1 | 12/2013 | Boivin et al. |
| 2014/0135368 | A1 | 5/2014 | Humljan et al. |
| 2016/0345581 | A1 | 12/2016 | Soergel et al. |
| 2017/0210712 | A1 | 7/2017 | Gockel et al. |

FOREIGN PATENT DOCUMENTS

| EP | 2671873 A1 | 12/2013 |
| JP | 2007326784 A | 12/2007 |
| WO | 199618628 A1 | 6/1996 |
| WO | 1999064402 A1 | 12/1999 |
| WO | 2001007436 A2 | 2/2001 |
| WO | 2002100352 A2 | 12/2002 |
| WO | 2009027393 A2 | 3/2009 |
| WO | 2009068652 A1 | 6/2009 |
| WO | 2009152325 A1 | 12/2009 |
| WO | 2010034737 A1 | 4/2010 |
| WO | 2010034738 A2 | 4/2010 |
| WO | 2010049841 A1 | 5/2010 |
| WO | 2010112177 A1 | 10/2010 |
| WO | 2010142628 A1 | 12/2010 |
| WO | 2011038572 A1 | 4/2011 |
| WO | 2011124524 A1 | 10/2011 |
| WO | 2012019015 A2 | 2/2012 |
| WO | 2012098387 A1 | 7/2012 |
| WO | 2012142217 A1 | 10/2012 |
| WO | 2012143317 A1 | 10/2012 |
| WO | 2013004984 A1 | 1/2013 |
| WO | 2013142269 A1 | 9/2013 |
| WO | 2013189801 A1 | 12/2013 |
| WO | 2014091368 A1 | 6/2014 |
| WO | 2015162133 A1 | 10/2015 |
| WO | 2015169734 A1 | 11/2015 |
| WO | 2015189080 A1 | 12/2015 |
| WO | 2016016369 A1 | 2/2016 |
| WO | 2016128239 A1 | 8/2016 |
| WO | 2016128240 A1 | 8/2016 |
| WO | 2016128261 A2 | 8/2016 |
| WO | 2016180833 A1 | 11/2016 |
| WO | 2017133942 A1 | 8/2017 |

OTHER PUBLICATIONS

Yukawa, et al., Pine Organic Chemistry, 5th Edition, Feb. 25, 1994, pp. 264-266.
Altenbach, et al., "Synthesis, Potency, and In Vivo Profiles of Quinoline Containing Histamine H3 Receptor Inverse Agonists", Journal of Medicinal Chemistry, vol. 50, Issue 22, 2007, pp. 5439-5448.
Alemagna, A., et al., "Arylazomethylenetriphenylphosphoranes: intra molecular reactions with aldonitronyl substituent in the ortho position with respect to the azophosphorane group", Tetrahedron, vol. 41, No. 12, Jan. 1, 1985, pp. 2503-2511.
Holschbach, MH et al., "Synthesis of 2-benzyl-2H-pyrazole-3,4-diamine dihydrochloride," Tetrahedron Letters, Pergamon, GB, vol. 44, No. 1, Jan. 1, 2003, pp. 41-43.
Konyukhova, N.A., et al., "Chemistry of Heterocyclic Compounds," vol. 37, No. 6, Jan. 1, 2001, pp. 779-780.

(Continued)

*Primary Examiner* — Shawquia Jackson
(74) *Attorney, Agent, or Firm* — Brinks Gilson & Lione

(57) ABSTRACT

The present invention relates to a process for preparing a pyrazole compound of formula V, which comprises cyclizing a hydrazone substituted α,β-unsaturated carbonyl compound of formula IV by reacting it with a suitable reagent, e.g. a reducing agent, an organometallic reagent or a nucleophilic reagent. The compounds of formula V are versatile reaction tools for the preparation of pyrazole derived fine chemicals. The present invention also relates to pyrazole compounds of formulae Va, Vb, Vc, and VI.

5 Claims, No Drawings

(56) References Cited

OTHER PUBLICATIONS

Kralj D et al., "3-(Dimethylamino) Propenoate-Based Regioselective Synthesis of 1, 4-Dusibstituted 5-Hydroxy-1-Hpyrazoles," Heterocycles: An International Journal for Review and Communications in Heterocyclic Chemistry, Japan Institute of Heterocyclic Chemistry, JP, vol. 68, No. 5, Mar. 31, 2006, pp. 897-914.

Lipunova, G.N. et al., "Fluorine-Containing Heterocycles: VIII. Transformations of 2-Polyfluorobenzoylacrylates Having a Thiosemicarbazide Fragment," Russian Journal of Organic Chemistry, Consultants Bureau, US, vol. 38, No. 12, Dec. 1, 2002, pp. 1851-1856.

Yakimovich, S.I., et al., "Reactions of 3-ethoxymethylidenipentane-2, 4-dione and ethyl 2-ethoxymethylidene-3, oxobutanoate with benzohydrazide," Russian Journal of Organic Chemistry, vol. 44, No. 4, Apr. 1, 2008, pp. 621-623.

Baranov, et al. Russian Journal of Applied Chemistry, vol. 77, No. 12, 2004, pp. 1997-2000.

Botteghi, et al. Journal of Organometallic Chemistry, 1989, 370, pp. 17-31. English Abstract.

Chang, Fei et al: "Pd-catalyzed Dehalogenation of Aromatic Halides Under Solvent-free Conditions Using Hydrogen Balloon", Bulletin of the Korean Chemical Society, vol. 32, No. 3, 20 Mar. 2011, pp. 1074-1076.

Kuraishi, Tsukasa et al: "Synthesis of 4-Aminopyridazine", Pharmaceutical Bulletin, vol. 4, No. 2, Jan. 1, 1956, pp. 137-138.

Peet, Journal of Heterocyclic Chemistry 21(5), 1984, pp. 1389-1392.

Romero et al. "Targeting Delavirdine/Atevirdine Resistant HIV-1: Identification of (Alkylamino)piperidine-Containing 3is(heteroaryl)piperazines as Broad Spectrum HIV-1 Reverse Transcriptase Inhibitors," J. Med. Chem, 1996, 39, 3769-3789.

PROCESS FOR PREPARING PYRAZOLES

CROSS-REFERENCE TO RELATED APPLICATIONS

This application is a divisional of U.S. application Ser. No. 15/329,104, filed Jan. 25, 2017, the entire contents of which is hereby incorporated herein by reference. U.S. application Ser. No. 15/329,104 is a National Stage application of International Application No. PCT/EP2015/067507, filed Jul. 30, 2015, the entire contents of which is hereby incorporated herein by reference. U.S. application Ser. No. 15/329,104 also claims priority under 35 U.S.C. § 119 to European Patent Application No. 14179249.9, filed Jul. 31, 2014, the contents of which are expressly incorporated herein by reference.

DESCRIPTION

The present invention relates to a process for preparing a pyrazole compound according to the following reaction sequence:

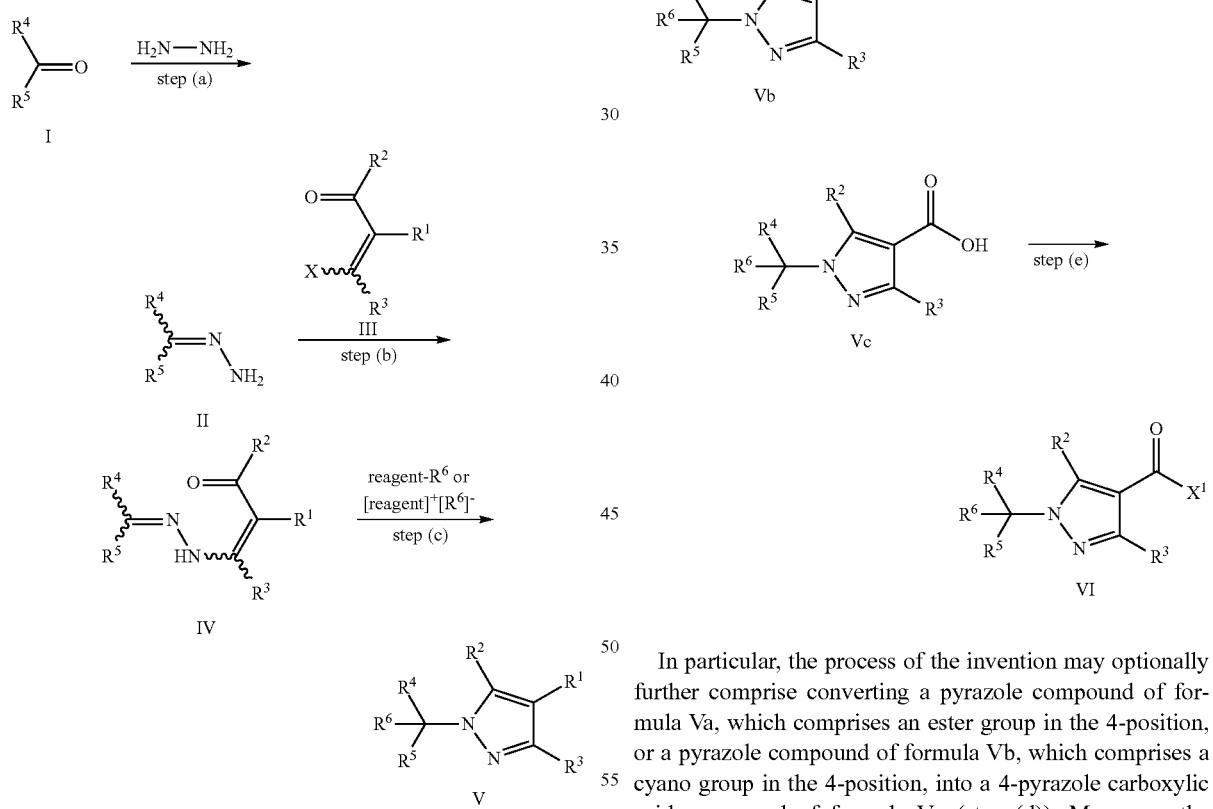

In particular, the present invention is directed to a process of preparing a pyrazole compound of formula V, which comprises cyclizing a hydrazone substituted α,β-unsaturated carbonyl compound of formula IV by reacting it with a suitable reagent, e.g. a reducing agent, an organometallic reagent or a nucleophilic reagent (step (c)). The process may further comprise preparing the hydrazone substituted α,β-unsaturated carbonyl compound of formula IV by reacting an α,β-unsaturated carbonyl compound of formula III, which contains a leaving group in the β-position, with a hydrazone compound of formula II (step (b)), and preparing said hydrazone compound of formula II by reacting a carbonyl compound of formula I with hydrazine (step (a)).

The process of the present invention may further comprise steps of converting certain 4-substituted pyrazole compounds into activated 4-pyrazole carboxylic acid derivatives according to the following reaction sequence:

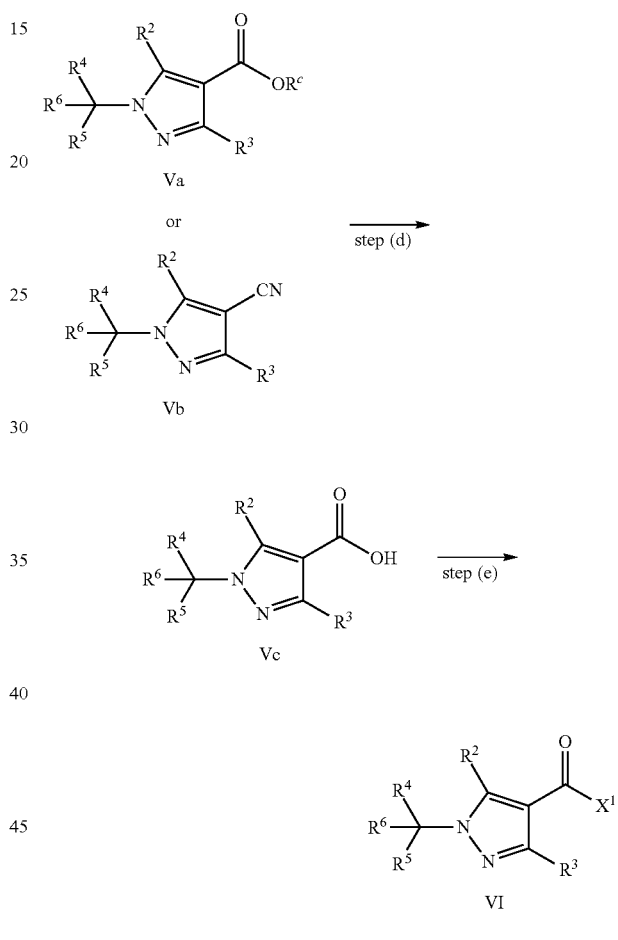

In particular, the process of the invention may optionally further comprise converting a pyrazole compound of formula Va, which comprises an ester group in the 4-position, or a pyrazole compound of formula Vb, which comprises a cyano group in the 4-position, into a 4-pyrazole carboxylic acid compound of formula Vc (step (d)). Moreover, the process may further comprise converting a 4-pyrazole carboxylic acid compound of formula Vc into an activated 4-pyrazole carboxylic acid derivative of formula VI (step (e)).

The process of the present invention may still further comprise the step of converting 4-activated pyrazole carboxylic acid derivatives into 4-pyrazole N-(het)arylamide compounds, which are known as pesticidally active compounds, according to the following reaction:

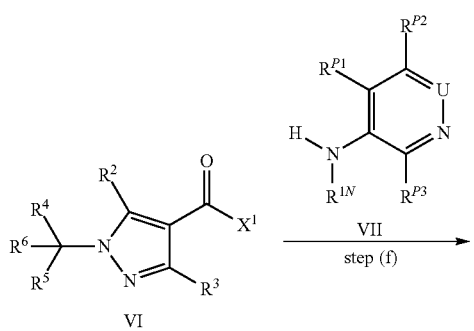

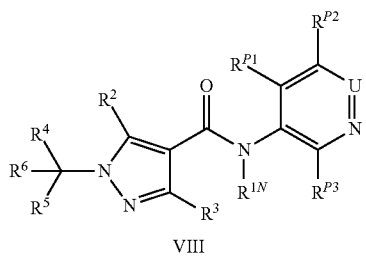

In particular, the process may still further comprise the step of reacting an activated 4-pyrazole carboxylic acid derivative of formula VI with a suitable suitable N-(het) arylamine compound of formula VII to yield a 4-pyrazole N-(het)arylamide compound of formula VIII (step (f)).

The present invention also relates to novel pyrazole compounds of formulae Va, Vb, Vc and VI.

Pyrazole compounds, in particular 4-pyrazole carboxylic acid derivatives, such as esters, nitriles, acids and activated acid derivatives, are versatile intermediate compounds for the preparation of pyrazole derived fine chemicals, such as compounds in the pharmaceutical or agrochemical field. In particular the compounds are versatile intermediate compounds for the preparation of pyrazole derived pesticides, such as 4-pyrazole N-(het)arylamide compounds, which are known to be particularly useful for combating invertebrate pests (see WO 2009/027393, WO 2010/034737, WO 2010/034738, and WO 2010/112177). Of particular interest are pyrazole compounds and 4-pyrazole carboxylic acid derivatives, which are substituted at one nitrogen atom and optionally also substituted in the 3- and/or 5-position because also the pyrazole derived pesticides including the above mentioned 4-pyrazole amide compounds often comprise pyrazole moieties, which are substituted accordingly.

In view of the above, there is a need for a process for preparing N-substituted pyrazole compounds and optionally further converting them into pyrazole derived pesticides. A particular problem accompanying the preparation of N-substituted pyrazole compounds is the regioselectivity, if substituents are present in the 3- and/or 5-position of the pyrazole ring, in particular, if a substituent is present in the 3-position, but not in the 5-position, if a substituent is present in the 5-position, but not in the 3-position, or if different substituents are present in the 3- and 5-position. Accordingly, there is a particular need for a process for regioselectively preparing N-substituted pyrazole compounds, which have a substituent either in the 3- or in the 5-position or different substituents in the 3- and 5-position of the pyrazole ring. In view of the preparation of 4-pyrazole N-(het)arylamide compounds as pesticides, such a process should particularly be suitable for regioselectively obtaining N-substituted 4-pyrazole carboxylic acid derivatives, which have a substituent either in the 3- or in the 5-position or different substituents in the 3- and 5-position of the pyrazole ring.

It is noted that the numbering of the atoms of an N-substituted pyrazole compound is usually as follows.

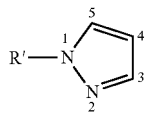

The positions of the substituents are indicated by the same numbers. The substituent at the nitrogen atom is typically referred to as the N-substituent rather than as substituent in the 1-position, although this is also suitable. The 2-position, i.e. the second nitrogen atom of the N-substituted pyrazole compounds, is typically unsubstituted. In contrast, the 3-, 4- and 5-positions may each be substituted.

There are principally two processes known for the preparation of N-substituted 4-pyrazole carboxylic acid derivatives, which are 3- and/or 5-substituted.

Firstly, such N-substituted 4-pyrazole carboxylic acid derivatives can be prepared by reacting an α,β-unsaturated carbonyl compound, e.g. an α,β-unsaturated ketone, which contains a leaving group in the β-position, with a hydrazine derivative, which has a substituent at one of the two nitrogen atoms. In view of the fact that the substituted hydrazine derivative comprises two amino groups, which are often very similar in terms of their nucleophilic reactivity, two regioisomers of the desired N-substituted pyrazole compound are usually obtained because either the substituted nitrogen atom or the unsubstituted nitrogen atom of the hydrazine derivative may react. Reactions, wherein the substituted hydrazine derivatives are used in the form of salts, have already been described, e.g., in JP 2007/326784, WO 2010/142628, and WO 2012/019015, and reactions, wherein mono-protected substituted hydrazine derivatives are used, have been described in WO 2012/019015. However, the regioselectivity problem in terms of the 3-/5-substitution pattern of the resulting N-substituted 4-pyrazole carboxylic acid derivatives could not be solved.

Secondly, N-substituted 4-pyrazole carboxylic acid derivatives, which are 3- and/or 5-substituted, can be prepared by reacting an α,β-unsaturated carbonyl compound, e.g. an α,β-unsaturated ketone, which contains a leaving group in the β-position, with hydrazine and then N-alkylating the resulting pyrazole derivative. Due to the tautomerism of the pyrazole compound, which is obtained as an intermediate, two regioisomers of the desired N-substituted pyrazole compound are usually obtained upon alkylation. Such reaction sequences have, e.g., been described in Heterocycles 2000, 2775, Liebigs Analen der Chemie 1985, 794, or Journal of Heterocyclic Chemistry 1985, 1109.

A process for regioselectively preparing N-substituted 4-pyrazole carboxylic acid derivatives, which are 3-substituted or 3- and 5-substituted with different substituents, was published by Glorius et al. in Angew. Chem. Int. Ed. 2010, 7790, and Green Chem. 2012, 14, 2193. Said process is performed by reacting an enamine compound with an excess of a suitable nitrile compound in the presence of stochiometric or catalytic amounts of copper.

Although the process regioselectively provides N-substituted 4-pyrazole carboxylic acid derivatives, which are 3-substituted or 3- and 5-substituted with different substituents, the process is disadvantageous in that copper is involved as a heavy metal, and an excess of at least three equivalents of the nitrile compound has to be used, so that the process is not environmentally friendly and not economical. Furthermore, the process has not been described for HCN as nitrile compound, most likely for the reason that HCN would polymerize under the reaction conditions, so that a cyclization reaction with the enamine compound according to the above reaction scheme would not take place. As a consequence, N-substituted 4-pyrazole carboxylic acid derivatives, which are 5-substituted, but not 3-substituted, can obviously not be obtained according to the process described by Glorius et al.

In view of the above, it is an object of the invention to provide a process for preparing N-substituted pyrazole compounds and optionally further converting them into pyrazole derived pesticides. In particular, it is an object to provide a process for preparing N-substituted pyrazole compounds, which are substituted e.g. in the 3- and/or 5-position and/or in the 4-position, wherein these substituents may be identical or different, preferably different.

It is another object of the invention to provide a process for regioselectively preparing N-substituted pyrazole compounds, which are 3- and/or 5-substituted. In particular, it is an object to provide regioselective access to a variety of N-substituted pyrazole compounds, which are 3-substituted, 5-substituted or 3- and 5-substituted with different substituents, and preferably 5-substituted, but not 3-substituted.

It is yet another object of the invention to provide a process for regioselectively preparing N-substituted 4-pyrazole carboxylic acid derivatives, for example esters or nitriles, which are 3- and/or 5-substituted. In particular, it is an object to provide regioselective access to a variety of N-substituted 4-pyrazole carboxylic acid derivatives, which are 3-substituted, 5-substituted or 3- and 5-substituted with different substituents, and preferably 5-substituted, but not 3-substituted.

In connection with the above objects, it is a further object to provide a process, which can be performed from readily and cheaply available starting materials. Furthermore, it is an object in connection with the above objects to provide a process, which is economical in terms of the yields and the amounts of the reactants, which are reacted with each other. Moreover, it is an object in connection with the above objects to provide a process, which is suitable for a technical scale.

It is yet another object of the invention to provide a process, which further allows for the provision of the free N-substituted 4-pyrazole carboxylic acids and activated derivatives thereof, wherein said compounds are preferably 3- and/or 5-substituted, e.g. 3-substituted, 5-substituted or 3- and 5-substituted with different substituents, and particularly preferably 5-substituted, but not 3-substituted.

It is yet another object of the invention to provide a process, which further allows for the provision of N-substituted 4-pyrazole amides, wherein the pyrazole moiety is preferably 3- and/or 5-substituted, e.g. 3-substituted, 5-substituted or 3- and 5-substituted with different substituents, and particularly preferably 5-substituted, but not 3-substituted.

Furthermore, it is an object of the invention to provide N-substituted 4-pyrazole carboxylic acid derivatives, for example esters or nitriles, N-substituted 4-pyrazole carboxylic acids and activated derivatives thereof, which may in each case be 3- and/or 5-substituted, e.g. 3-substituted, 5-substituted or 3- and 5-substituted with different substituents, and preferably 5-substituted, but not 3-substituted. In particular, it is an object to provide N-substituted 4-pyrazole carboxylic acid derivatives, N-substituted 4-pyrazole carboxylic acids and activated derivatives thereof, which have specific N-substituents and specific substituents in the 5-position, but are unsubstituted in the 3-position, because such pyrazole compounds are suitable for the preparation of 4-pyrazole N-(het)arylamide compounds with an exceptionally high pesticidally activity.

The above objects are achieved by the processes and compounds described in detail in the claims and hereinafter.

In one aspect, the present invention relates to preparing a pyrazole compound of formula V or a salt, stereoisomer, tautomer or N-oxide thereof

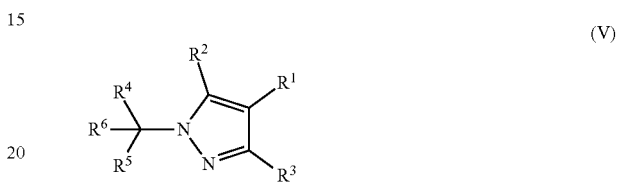

comprising the step of cyclizing a hydrazone substituted α,β-unsaturated carbonyl compound of formula IV

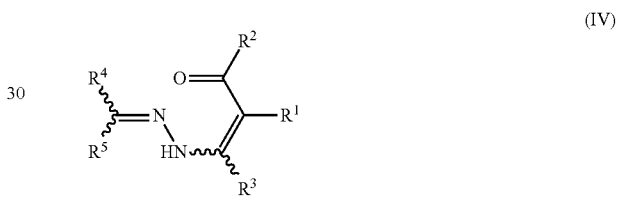

by reacting it with a reagent comprising a $R^6$ group, wherein $R^1$ is selected from H, halogen, CN, $NO_2$, $C_1$-$C_{10}$-alkyl, $C_2$-$C_{10}$-alkenyl, $C_2$-$C_{10}$-alkynyl, wherein the C-atoms be unsubstituted, may be partially or fully halogenated or may be substituted by 1, 2, or 3 identical or different substituents $R^x$;
  $OR^a$, $SR^a$, $C(Y)OR^c$, $S(O)_mR^d$, $S(O)_mY^1R^d$, $NR^eR^f$, $C(Y)NR^gR^h$, heterocyclyl, hetaryl, $C_3$-$C_{10}$-cycloalkyl, $C_3$-$C_{10}$-cycloalkenyl and aryl, wherein the cyclic moieties may be unsubstituted or substituted by 1, 2, 3, 4, or 5 identical or different substituents selected from the radicals $R^y$ and $R^x$;

$R^2$ is selected from H, $C_1$-$C_{10}$-alkyl, $C_2$-$C_{10}$-alkenyl, $C_2$-$C_{10}$-alkynyl, wherein the C-atoms may be unsubstituted, may be partially or fully halogenated or may be substituted by 1, 2, or 3 identical or different substituents $R^x$;
  $C(Y)OR^c$, $C(Y)NR^gR^h$, heterocyclyl, hetaryl, $C_3$-$C_{10}$-cycloalkyl, $C_3$-$C_{10}$-cycloalkenyl and aryl, wherein the cyclic moieties may be unsubstituted or may be substituted by 1, 2, 3, 4, or 5 identical or different substituents selected from the radicals $R^y$ and $R^x$; and $R^3$ is selected from H, halogen, CN, $NO_2$, $C_1$-$C_{10}$-alkyl, $C_2$-$C_{10}$-alkenyl, $C_2$-$C_{10}$-alkynyl, wherein the C-atoms may be unsubstituted, may be partially or fully halogenated or may be substituted by 1, 2, or 3 identical or different substituents $R^x$;
  $OR^a$, $SR^a$, $C(Y)OR^c$, $S(O)_mR^d$, $S(O)_mY^1R^d$, $NR^eR^f$, $C(Y)NR^gR^h$, heterocyclyl, hetaryl, $C_3$-$C_{10}$-cycloalkyl, $C_3$-$C_{10}$-cycloalkenyl and aryl, wherein the cyclic moieties may be unsubstituted or may be substituted by 1, 2, 3, 4, or 5 identical or different substituents selected from the radicals $R^y$ and $R^x$;

and wherein $R^4$ and $R^5$ are independently of each other selected from H, $NO_2$, $C_1$-$C_{10}$-alkyl, $C_2$-$C_{10}$-alkenyl, $C_2$-$C_{10}$-alkynyl, wherein the C-atoms may be unsubstituted, may be partially or fully halogenated or may be substituted by 1, 2 or 3 identical or different substituents $R^x$; $C_1$-$C_{10}$-haloalkyl, $C_1$-$C_4$-alkoxy-$C_1$-$C_{10}$-alkyl, wherein the C-atoms may be unsubstituted, or partially or fully substituted by identical or different substituents $R^y$; $C(Y)OR^c$, $C(Y)NR^gR^h$, $C(Y)NR^iNR^eR^f$, $C_1$-$C_5$-alkylen-$OR^a$, $C_1$-$C_5$-alkylen-CN, $C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_mR^d$, $C_1$-$C_5$-alkylen-$S(O)_mNR^eR^f$, $C_1$-$C_5$-alkylen-$NR^iNR^eR^f$;

heterocyclyl, $C_3$-$C_{10}$-cycloalkyl, $C_3$-$C_{10}$-cycloalkenyl, hetaryl, aryl, heterocyclyl-$C_1$-$C_5$-alkyl, $C_3$-$C_{10}$-cycloalkyl-$C_1$-$C_5$-alkyl, $C_3$-$C_{10}$-cycloalkenyl-$C_1$-$C_5$-alkyl, hetaryl-$C_1$-$C_5$-alkyl, aryl-$C_1$-$C_5$-alkyl, wherein the cyclic moieties may be unsubstituted or may be substituted by 1, 2, 3, 4, or 5 identical or different substituents $R^y$;

groups -D-E, wherein
  D is a direct bond, $C_1$-$C_6$-alkylene, $C_2$-$C_6$-alkenylene, or $C_2$-$C_6$-alkynylene, which carbon chains can be partially or fully substituted by $R^n$, and
  E is a non-aromatic 3- to 12-membered carbo- or heterocycle, which may contain 1, 2, 3, or 4 heteroatoms selected from N—$R^l$, O, and S, wherein S may be oxidized, which carbo- or heterocycle may be partially or fully substituted by $R^n$;

and groups -A-$SO_m$-G, wherein
  A is $C_1$-$C_6$-alkylene, $C_2$-$C_6$-alkenylene and $C_2$-$C_6$-alkynylene, wherein the C-atoms may be unsubstituted, or partially or fully substituted by $R^p$, and
  G is $C_1$-$C_4$-haloalkyl or $C_3$-$C_6$-cycloalkyl which may be halogenated;

or $R^4$ and $R^5$ together with the carbon atom to which they are attached form a 3- to 12-membered non-aromatic carbo- or heterocycle, which heterocycle may contain 1, 2, 3, 4, or 5 heteroatoms selected from N—$R^l$, O, and S, wherein S may be oxidized, and which carbo- or heterocycle may be partially or fully substituted by $R^j$;

and wherein $R^6$ is selected from H, CN, $C_1$-$C_6$-fluoroalkyl, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_2$-alkyl, $C_3$-$C_6$-cycloalkenyl, $C_3$-$C_6$-cycloalkenyl-$C_1$-$C_2$-alkyl, heterocyclyl, heterocyclyl-$C_1$-$C_2$-alkyl, aryl, aryl-$C_1$-$C_2$-alkyl, hetaryl, hetaryl-$C_1$-$C_2$-alkyl, wherein the carbon chains or cyclic moieties may be unsubstituted, partially or fully substituted by identical or different substituents $R^x$;

$OR^a$, $SR^a$, $NR^eR^f$, and groups of general formula (i)

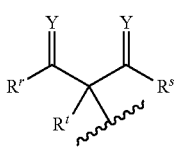

(i)

and wherein $R^a$, $R^b$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the cyclic moieties may be unsubstituted or may be substituted by 1, 2, 3, 4, or 5 substituents which, independently of each other, are selected from halogen, CN, $C(O)NH_2$, $NO_2$, $C_1$-$C_4$-alkyl, $C_1$-$C_4$-haloalkyl, $C_1$-$C_4$-alkoxy and $C_1$-$C_4$-haloalkoxy;

$R^c$ is selected from H, $C_1$-$C_{10}$-alkyl, $C_1$-$C_{10}$-haloalkyl, $C_3$-$C_{10}$-cycloalkyl, $C_3$-$C_{10}$-cycloalkylmethyl, $C_3$-$C_{10}$-halocycloalkyl, $C_3$-$C_6$-cycloalkenyl, $C_3$-$C_6$-cycloalkenylmethyl, $C_3$-$C_6$-halocycloalkenyl, $C_2$-$C_{10}$-alkenyl, $C_2$-$C_{10}$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the ring in the six last mentioned radicals may be unsubstituted or may be substituted by 1, 2, 3, 4, or 5 substituents which, independently of each other, are selected from halogen, CN, $C(O)NH_2$, $NO_2$, $C_1$-$C_4$-alkyl, $C_1$-$C_4$-haloalkyl, $C_1$-$C_4$-alkoxy and $C_1$-$C_4$-haloalkoxy; or $R^c$ together with the $C(Y)O$ group forms a salt $[C(Y)O]^-NR_4^+$, $[C(Y)O]^-M_a^+$ or $[C(Y)O]^-\frac{1}{2}M_{ea}^{2+}$, wherein $M_a$ is an alkali metal and $M_{ea}$ is an alkaline earth metal, and wherein the substituents R at the nitrogen atom are independently of each other selected from H, $C_1$-$C_{10}$-alkyl, phenyl and phenyl-$C_1$-$C_4$-alkyl;

$R^d$ is selected from $C_1$-$C_4$-alkoxy, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the cyclic moieties may be unsubstituted or may be substituted by 1, 2, 3, 4, or 5 substituents which are independently of each other selected from halogen, CN, $C(O)NH_2$, $NO_2$, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, heterocyclyl, heterocyclyl-$C_1$-$C_4$-alkyl, heterocyclylcarbonyl, heterocyclyl-$C_1$-$C_4$-sulfonyl, aryl, arylcarbonyl, arylsulfonyl, hetaryl, hetarylcarbonyl, hetarylsulfonyl, aryl-$C_1$-$C_4$-alkyl and hetaryl-$C_1$-$C_4$-alkyl, wherein the cyclic moieties may be unsubstituted or may be substituted by 1, 2, 3, 4, or 5 substituents which, independently of each other, are selected from halogen, CN, $C(O)NH_2$, $NO_2$, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the N atom to which they are bonded form a 5- or 6-membered, saturated or unsaturated heterocycle, which may comprise a further heteroatom being selected from O, S and N as a ring member atom and wherein the heterocycle may be unsubstituted or may by substituted by 1, 2, 3, 4, or 5 substituents which are independently of each other selected from halogen, CN, C(O)NH$_2$, NO$_2$, C$_1$-C$_4$-alkyl, C$_1$-C$_4$-haloalkyl, C$_1$-C$_4$-alkoxy and C$_1$-C$_4$-haloalkoxy;

R$^g$, R$^h$ are independently of each other selected from H, C$_1$-C$_4$-alkyl, C$_1$-C$_4$-haloalkyl, C$_3$-C$_6$-cycloalkyl, C$_3$-C$_6$-halocycloalkyl, C$_3$-C$_6$-cycloalkenyl, C$_3$-C$_6$-halocycloalkenyl, C$_2$-C$_4$-alkenyl, C$_2$-C$_4$-haloalkenyl, C$_2$-C$_4$-alkynyl, C$_1$-C$_4$-alkoxy-C$_1$-C$_4$-alkyl, heterocyclyl, heterocyclyl-C$_1$-C$_4$-alkyl, aryl, hetaryl, aryl-C$_1$-C$_4$-alkyl and hetaryl-C$_1$-C$_4$-alkyl, wherein the cyclic moieties may be unsubstituted or may be substituted by 1, 2, 3, 4, or 5 substituents which are independently of each other selected from halogen, CN, C(O)NH$_2$, NO$_2$, C$_1$-C$_4$-alkyl, C$_1$-C$_4$-haloalkyl, C$_1$-C$_4$-alkoxy and C$_1$-C$_4$-haloalkoxy;

R$^i$ is selected from H, C$_1$-C$_4$-alkyl, C$_1$-C$_4$-haloalkyl, C$_3$-C$_6$-cycloalkyl, C$_3$-C$_6$-cycloalkylmethyl, C$_3$-C$_6$-halocycloalkyl, C$_3$-C$_6$-cycloalkenyl, C$_3$-C$_6$-cycloalkenylmethyl, C$_3$-C$_6$-halocycloalkenyl, C$_2$-C$_4$-alkenyl, C$_2$-C$_4$-haloalkenyl, C$_2$-C$_4$-alkynyl, C$_1$-C$_4$-alkoxy-C$_1$-C$_4$-alkyl, aryl, aryl-C$_1$-C$_4$-alkyl, wherein the aryl ring may be unsubstituted or may be substituted by 1, 2, 3, 4, or 5 substituents which are independently of each other selected from halogen, CN, C(O)NH$_2$, NO$_2$, C$_1$-C$_4$-alkyl, C$_1$-C$_4$-haloalkyl, C$_1$-C$_4$-alkoxy and C$_1$-C$_4$-haloalkoxy;

R$^j$ is halogen, OH, CN, C(O)NH$_2$, NO$_2$, C$_1$-C$_{10}$-alkyl, C$_1$-C$_{10}$-haloalkyl, C$_1$-C$_{10}$-alkoxy, C$_1$-C$_{10}$-haloalkoxy, benzyloxy, S(O)$_m$R$^k$, C$_3$-C$_6$-cycloalkyl, or a 3- to 6-membered heterocycle, which may contain 1 or 2 heteroatoms selected from N—R$^l$, O, and S, wherein S may be oxidized, which R$^j$ groups are unsubstituted or partially or fully substituted by R$^m$, and wherein two groups R$^j$ connected to the same or adjacent ring atoms may together form a 3- to 6-membered carbo- or heterocycle which heterocycle may contain 1 or 2 heteroatoms selected from N—R$^l$, O, and S, wherein S may be oxidized, which cycles may be partially or fully substituted by R$^m$ radicals;

R$^k$ is H, C$_1$-C$_4$-alkyl, C$_1$-C$_4$-haloalkyl, or C$_3$-C$_6$-cycloalkyl, which cycle may be partially or fully substituted by R$^l$;

R$^l$ is H, halogen, C$_1$-C$_4$-alkyl, C$_1$-C$_4$-haloalkyl, C$_1$-C$_4$-alkylcarbonyl, or C$_1$-C$_4$-alkoxycarbonyl;

R$^m$ is halogen, OH, CN, C(O)NH$_2$, NO$_2$, C$_1$-C$_4$-alkyl, C$_1$-C$_4$-haloalkyl, C$_3$-C$_6$-cycloalkyl, C$_1$-C$_4$-alkoxy, C$_1$-C$_4$-haloalkoxy, or S(O)$_m$R$^k$;

R$^n$ is halogen, CN, C(Y)OR$^c$, C(O)NH$_2$, NO$_2$, C$_1$-C$_2$-alkyl, C$_1$-C$_4$-haloalkyl, C$_2$-C$_6$-alkenyl, C$_2$-C$_6$-alkynyl, C$_3$-C$_6$-cycloalkyl, C$_3$-C$_6$-cycloalkenyl, C$_1$-C$_4$-alkoxy, C$_1$-C$_4$-haloalkoxy, C$_1$-C$_4$-alkoxy-C$_1$-C$_4$-alkyl, C$_1$-C$_4$-alkyliden, or S(O)$_m$R$^o$, two adjacent groups R$^n$ may form together with the atoms to which they are bonded a 3- to 8-membered carbo- or heterocycle, which may contain 1, 2, 3, or 4 heteroatoms selected from N—R$^l$, O, and S, wherein S may be oxidized, which cyclic R$^n$ moieties may be substituted by halogen, R$^o$, or R$^l$;

R$^o$ is H, C$_1$-C$_4$-alkyl, C$_1$-C$_4$-haloalkyl, C$_3$-C$_6$-cycloalkyl, or C$_1$-C$_4$-alkoxy;

R$^p$ is halogen, CN, C(O)NH$_2$, NO$_2$, C$_1$-C$_2$-alkyl, C$_1$-C$_2$-haloalkyl, C$_3$-C$_6$-cycloalkyl, C$_1$-C$_4$-alkoxy, or C$_1$-C$_2$-haloalkoxy, or two groups R$^p$ can together form a 3- to 6-membered carbo- or heterocyclic ring, which heterocycle contains 1 or 2 heteroatoms selected from N—R$^l$, O, and S, wherein S may be oxidized, which carbo- or heterocyclic ring is unsubstituted or partly or fully substituted by groups R$^q$;

R$^q$ is halogen, CN, C(O)NH$_2$, NO$_2$, C$_1$-C$_4$-alkyl, C$_1$-C$_4$-haloalkyl, C$_3$-C$_6$-cycloalkyl, C$_1$-C$_4$-alkoxy, or C$_1$-C$_4$-haloalkoxy;

R$^r$ and R$^s$ are independently of each other selected from R$^b$, OR$^{c1}$, and NR$^g$R$^h$;

R$^{c1}$ is C$_1$-C$_{10}$-alkyl, C$_1$-C$_{10}$-haloalkyl, C$_3$-C$_{10}$-cycloalkyl, C$_3$-C$_{10}$-cycloalkylmethyl, C$_3$-C$_{10}$-halocycloalkyl, C$_3$-C$_6$-cycloalkenyl, C$_3$-C$_6$-cycloalkenylmethyl, C$_3$-C$_6$-halocycloalkenyl, C$_2$-C$_{10}$-alkenyl, C$_2$-C$_{10}$-haloalkenyl, C$_2$-C$_4$-alkynyl, C$_1$-C$_4$-alkoxy-C$_1$-C$_4$-alkyl, heterocyclyl, heterocyclyl-C$_1$-C$_4$-alkyl, aryl, hetaryl, aryl-C$_1$-C$_4$-alkyl or hetaryl-C$_1$-C$_4$-alkyl, wherein the ring in the six last mentioned radicals may be unsubstituted or may be substituted with 1, 2, 3, 4 or substituents which, independently of each other, are selected from halogen, CN, C(O)NH$_2$, NO$_2$, C$_1$-C$_4$-alkyl, C$_1$-C$_4$-haloalkyl, C$_1$-C$_4$-alkoxy or C$_1$-C$_4$-haloalkoxy;

R$^t$ is H or R$^a$;

R$^x$ is halogen, CN, C(Y)OR$^c$, C(Y)NR$^g$R$^h$, NO$_2$, C$_1$-C$_4$-alkyl, C$_1$-C$_4$-haloalkyl, C$_1$-C$_4$-alkoxy, C$_1$-C$_4$-haloalkoxy, S(O)$_m$R$^d$, S(O)$_m$NR$^e$R$^f$, C$_1$-C$_5$-alkylen-NHC(O)OR$^c$, C$_1$-C$_{10}$-alkylcarbonyl, C$_1$-C$_4$-haloalkylcarbonyl, C$_1$-C$_4$-alkoxycarbonyl, C$_1$-C$_4$-haloalkoxycarbonyl, C$_3$-C$_6$-cycloalkyl, 5- to 7-membered heterocyclyl, 5- or 6-membered hetaryl, aryl, C$_3$-C$_6$-cycloalkoxy, 3- to 6-membered heterocyclyloxy, or aryloxy, wherein the cyclic moieties may be unsubstituted or may be substituted by 1, 2, 3, 4, or 5 radicals R$^y$; and R$^y$ is selected from halogen, CN, C(Y)OR$^c$, C(Y)NR$^g$R$^h$, NO$_2$, C$_1$-C$_4$-alkyl, C$_1$-C$_4$-haloalkyl, C$_1$-C$_4$-alkoxy, C$_1$-C$_4$-haloalkoxy, benzyloxymethyl, S(O)$_m$R$^d$, S(O)$_m$NR$^e$R$^f$, C$_1$-C$_4$-alkylcarbonyl, C$_1$-C$_4$-haloalkylcarbonyl, C$_1$-C$_4$-alkoxycarbonyl, C$_1$-C$_4$-haloalkoxycarbonyl, C$_3$-C$_6$-cycloalkyl, C$_3$-C$_6$-halocycloalkyl, C$_2$-C$_4$-alkenyl, C$_2$-C$_4$-haloalkenyl, C$_2$-C$_4$-alkynyl and C$_1$-C$_4$-alkoxy-C$_1$-C$_4$-alkyl;

and wherein

Y is O or S;

Y is O, S, or N—R$^{1a}$;

R$^{1a}$ is H, C$_1$-C$_{10}$-alkyl, C$_3$-C$_{12}$-cycloalkyl, aryl, or hetaryl; and m is 0, 1 or 2.

Preferably, formula IV is to be understood as not only covering the compounds as such, but also as covering salts, stereoisomers, tautomers or N-oxides of the compounds of formula IV.

The process as defined above is suitable for providing a variety of N-substituted pyrazole compounds of formula V, which may be further converted to give pyrazole derived pesticides.

Furthermore, it has surprisingly been found that the process is suitable for regioselectively preparing a variety of N-substituted pyrazole compounds, which are 3- or 5-substituted or substituted with different substituents in the 3- and 5-position. In particular, the substitution pattern of the compounds of formula IV predefines the substitution pattern of the resulting N-substituted pyrazole compounds, so that the problem of regioselectivity can completely be avoided. The compound of formula IV can be selected as such, that a variety of substituents in the 3- and/or 5- as well as in the 4-position of the N-substituted pyrazole compounds can be realized. In this context, it has also been found that N-substituted 4-pyrazole carboxylic acid derivatives, which are 3- or 5-substituted or substituted with different substituents in the 3- and 5-position, can regioselectively be obtained by the process according to the present invention.

The process provides the N-substituted pyrazole compounds of formula V in high yields based on the amounts of the compounds of formula IV.

Furthermore, it is an advantage of the process that the compounds of formula IV can be obtained from readily and cheaply available starting materials. In particular, it is an advantage that the compounds of formula IV can be obtained by reacting α,β-unsaturated carbonyl compounds of formula III, which contain a leaving group in the β-position, with hydrazone compounds of formula II, wherein the α,β-unsaturated carbonyl compounds of formula III are readily available either commercially or by methods known in the art, and the hydrazone compounds of formula II can easily be obtained by reacting commercially available carbonyl compounds of formula I with hydrazine. This will be outlined in further detail below. By varying the carbonyl compounds of formula I and the α,β-unsaturated carbonyl compounds of formula III, a variety of compounds of formulae II, IV and V can thus easily be obtained.

Furthermore, the compounds of formula V can be further converted into pyrazole derived pesticides. For example, if the pyrazole compound of formula V is a pyrazole compound of formula Va or Vb with an ester or a cyano group in the 4-position, said compound can easily be converted into the corresponding 4-pyrazole carboxylic acid compound of formula Vc. Alternatively, such 4-pyrazole carboxylic acid compounds of formula Vc may directly be obtained from suitable compounds of formula IV. From the 4-pyrazole carboxylic acid compound of formula Vc, activated 4-pyrazole carboxylic acid derivatives of formula VI can be obtained by standard activation processes. The compounds of formula VI may then be converted into 4-pyrazole N-(het)arylamide compounds of formula VIII, which may represent highly active pesticides.

In view of the above, certain preferred embodiments of the invention relate to a process, wherein the hydrazone substituted α,β-unsaturated carbonyl compound of formula IV

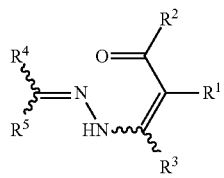

(IV)

is prepared by reacting an α,β-unsaturated carbonyl compound of formula III

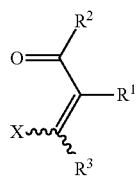

(III)

with a hydrazone compound of formula II

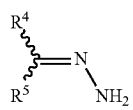

(II)

wherein

X is a leaving group and $R^1$, $R^2$, $R^3$, $R^4$ and $R^5$ are as defined above.

Furthermore, certain more preferred embodiments of the invention relate to a process, wherein the above hydrazone compound of formula II is prepared by reacting a carbonyl compound of formula I

(I)

with hydrazine or a salt thereof, wherein $R^4$ and $R^5$ are as defined above.

Preferably, formulae I, II, III and IV are to be understood as not only covering the compounds as such, but also as covering salts, stereoisomers, tautomers or N-oxides of these compounds. However, N-oxides are of course only possible, if a nitrogen atom is present in the compounds.

In view of the above, certain preferred embodiments of the invention further relate to a process, wherein the compound of formula V is a compound of formula Va or Vb

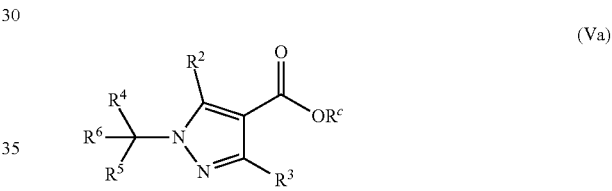

(Va)

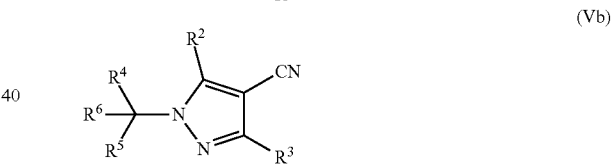

(Vb)

and wherein said compound of formula Va or Vb is converted into a compound of formula Vc

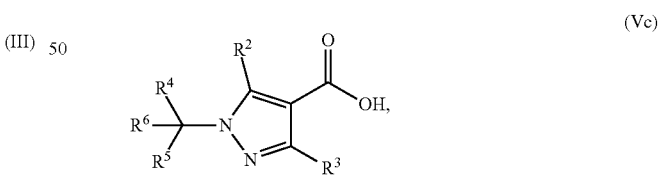

(Vc)

wherein $R^2$, $R^3$, $R^4$, $R^5$ and $R^6$ are as defined above, and wherein $R^c$ in formula Va is $C_1$-$C_4$-alkyl or aryl-$C_1$-$C_4$-alkyl.

Preferably, formulae Va, Vb and Vc are to be understood as not only covering the compounds as such, but also as covering salts, stereoisomers, tautomers or N-oxides of these compounds.

Furthermore, certain preferred embodiments of the invention relate to a process, wherein a compound of formula Vc is converted into a compound of formula VI

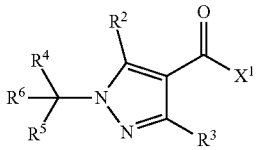

(VI)

wherein $X^1$ is a leaving group, and wherein $R^2$, $R^3$, $R^4$, $R^5$ and $R^6$ are as defined above.

With regard to $X^1$, it is noted that $X^1$ may be any leaving group, preferably a leaving group, which is suitable for amide coupling reactions.

For example, $X^1$ may be a leaving group, which is based on a peptide coupling reagent. Suitable peptide coupling reagents are described by Han et al. in Tetrahedron 60 (2004) 2447-2467. In this regard, N,N'-bis(2-oxo-3-oxazolidinyl)-phosphinic chloride (BOP-Cl) and O-(7-azabenzotriazol-1-yl)-1,1,3,3-tetramethyluronium hexafluorophosphate (HATU) are preferred according to the present invention.

Furthermore, $X^1$ may be a leaving group selected from active esters, azide and halogens.

Preferably, $X^1$ is selected from halogen, $N_3$, p-nitrophenoxy, and pentafluorophenoxy, and is particularly preferably halogen, such as Cl.

Preferably, formula VI is again to be understood as not only covering the compounds as such, but also as covering salts, stereoisomers, tautomers or N-oxides of these compounds.

Moreover, certain more preferred embodiments of the invention relate to a process, wherein the above compound of formula VI is converted into a compound of formula VIII

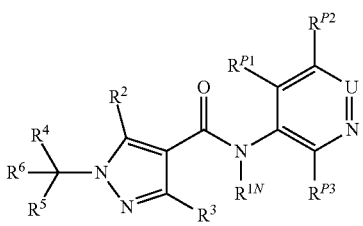

(VIII)

by reacting it with a compound of formula VII

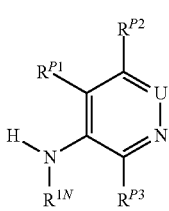

(VII)

wherein $R^2$, $R^3$, $R^4$, $R^5$ and $R^6$ are as defined above, and wherein

U is N or $CR^U$;

$R^{P1}$, $R^{P2}$, $R^{P3}$, and $R^U$ are independently of each other selected from H, halogen, $C_1$-$C_4$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl; and $R^{1N}$ is H, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_1$-$C_4$-alkoxy-$C_1$-$C_4$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_5$-alkylen-CN, $OR^a$, $C_1$-$C_5$-alkylen-$OR^a$, $C(Y)R^b$, $C_1$-$C_5$-alkylen-$C(Y)R^b$, $C(Y)OR^c$, $C_1$-$C_5$-alkylen-$C(Y)OR^c$, $S(O)_2R^d$, $NR^eR^f$, $C_1$-$C_5$-alkylen-$NR^eR^f$, $C(Y)NR^gR^h$, $C_1$-$C_5$-alkylen-$C(Y)NR^gR^h$, $S(O)_mNR^eR^f$, $C(Y)NR^iNR^eR^f$, $C_1$-$C_5$-alkylen-$S(O)_2R^d$, $C_1$-$C_5$-alkylen-$S(O)_mNR^eR^f$, $C_1$-$C_5$-alkylen-$C(Y)NR^iNR^eR^f$, aryl, heterocyclyl, hetaryl, aryl-$C_1$-$C_5$-alkyl, $C_3$-$C_{10}$-cycloalkyl-$C_1$-$C_5$-alkyl, heterocyclyl-$C_1$-$C_5$-alkyl or hetaryl-$C_1$-$C_5$-alkyl, wherein the cyclic moieties may be unsubstituted or may be substituted by 1, 2, 3, 4, or 5 identical or different substituents selected from the radicals $R^y$ and $R^x$.

Preferably, formulae VI and VIII are again to be understood as not only covering the compounds as such, but also as covering salts, stereoisomers, tautomers or N-oxides of these compounds.

In another aspect, the present invention relates to a compound of formula Va or a salt, stereoisomer, tautomer or N-oxide thereof

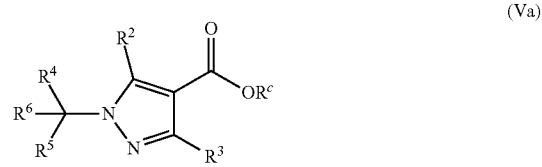

(Va)

wherein $R^2$ is $CH_3$, $R_3$ is H, $R^4$ is $CH(CH_3)_2$, $R^5$ is $CH_3$ and $R^6$ is H; or $R^2$ is $CH_3$, $R_3$ is H, $R^4$ is $CHFCH_3$, $R^5$ is $CH_3$ and $R^6$ is H; or $R^2$ is $CH_3$, $R_3$ is H, $R^4$ is 1-CN-$cC_3H_4$, $R^5$ is $CH_3$ and $R^6$ is H; or $R^2$ is $CH_3$, $R_3$ is H, $R^4$ is 1-C(O)NH$_2$-$cC_3H_4$, $R^5$ is $CH_3$ and $R^6$ is H; or $R^2$ is $CH_3$, $R_3$ is H, $R^4$ and $R^5$ together are $CH_2CH_2CF_2CH_2CH_2$, and $R^6$ is H;

and wherein $R^c$ is $C_1$-$C_4$-alkyl or aryl-$C_1$-$C_4$-alkyl, or wherein $R^c$ together with the C(O)O group forms a salt [C(O)O]—$NR_4^+$, $[C(O)O]^-M_a^+$ or $[C(O)O]^-\frac{1}{2}M_{ea}^{2+}$, wherein $M_a$ is an alkali metal and $M_{ea}$ is an alkaline earth metal; and wherein the substituents R at the nitrogen atom are independently of each other selected from H, $C_1$-$C_{10}$-alkyl, phenyl and phenyl-$C_1$-$C_4$-alkyl.

In yet another aspect, the present invention relates to a compound of formula Vb or a salt, stereoisomer, tautomer or N-oxide thereof

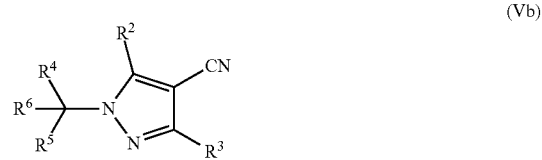

(Vb)

wherein
R$^2$ is CH$_3$, R$_3$ is H, R$^4$ is CH(CH$_3$)$_2$, R$^5$ is CH$_3$ and R$^6$ is H; or
R$^2$ is CH$_3$, R$_3$ is H, R$^4$ is CHFCH$_3$, R$^5$ is CH$_3$ and R$^6$ is H; or
R$^2$ is CH$_3$, R$_3$ is H, R$^4$ is 1-CN-cC$_3$H$_4$, R$^5$ is CH$_3$ and R$^6$ is H; or
R$^2$ is CH$_3$, R$_3$ is H, R$^4$ is 1-C(O)NH$_2$-cC$_3$H$_4$, R$^5$ is CH$_3$ and R$^6$ is H; or
R$^2$ is CH$_3$, R$_3$ is H, R$^4$ and R$^5$ together are CH$_2$CH$_2$CF$_2$CH$_2$CH$_2$, and R$^6$ is H.

The compounds of formula Va and Vb represent precursors for N-substituted 4-pyrazole carboxylic acids Vc, which itself represent versatile reaction tools for the preparation of certain 4-pyrazole N-(het)arylamide compounds of formula VIII, which are highly active pesticides.

Thus, in another aspect, the present invention relates to a compound of formula Vc or a salt, stereoisomer, tautomer or N-oxide thereof

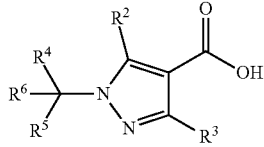

(Vc)

wherein
R$^2$ is CH$_3$, R$_3$ is H, R$^4$ is CH(CH$_3$)$_2$, R$^5$ is CH$_3$ and R$^6$ is H; or
R$^2$ is CH$_3$, R$_3$ is H, R$^4$ is CHFCH$_3$, R$^5$ is CH$_3$ and R$^6$ is H; or
R$^2$ is CH$_3$, R$_3$ is H, R$^4$ is 1-CN-cC$_3$H$_4$, R$^5$ is CH$_3$ and R$^6$ is H; or
R$^2$ is CH$_3$, R$_3$ is H, R$^4$ is 1-C(O)NH$_2$-cC$_3$H$_4$, R$^5$ is CH$_3$ and R$^6$ is H; or
R$^2$ is CH$_3$, R$_3$ is H, R$^4$ and R$^5$ together are CH$_2$CH$_2$CF$_2$CH$_2$CH$_2$, and R$^6$ is H.

The 4-pyrazole carboxylic acid compounds of formula Vc can easily be activated for a subsequent amidation reaction to give the 4-pyrazole N-(het)arylamide compounds of formula VIII.

Thus, in yet another aspect, the present invention relates to a compound of formula VI or a salt, stereoisomer, tautomer or N-oxide thereof

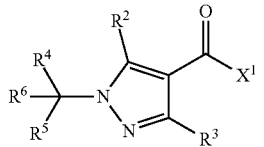

(VI)

wherein
R$^2$ is CH$_3$, R$_3$ is H, R$^4$ is CH(CH$_3$)$_2$, R$^5$ is CH$_3$ and R$^6$ is H; or
R$^2$ is CH$_3$, R$_3$ is H, R$^4$ is CHFCH$_3$, R$^5$ is CH$_3$ and R$^6$ is H; or
R$^2$ is CH$_3$, R$_3$ is H, R$^4$ is 1-CN-cC$_3$H$_4$, R$^5$ is CH$_3$ and R$^6$ is H; or
R$^2$ is CH$_3$, R$_3$ is H, R$^4$ is 1-C(O)NH$_2$-cC$_3$H$_4$, R$^5$ is CH$_3$ and R$^6$ is H; or
R$^2$ is CH$_3$, R$_3$ is H, R$^4$ and R$^5$ together are CH$_2$CH$_2$CF$_2$CH$_2$CH$_2$, and R$^6$ is H;
and wherein
X$^1$ is a leaving group, which is preferably selected from halogen, N$_3$, p-nitrophenoxy, and pentafluorophenoxy, and which is particularly preferably Cl.

The compounds of formula VI represent activated species, which can either be formed in situ or isolated after activation of the 4-pyrazole carboxylic acid compounds of formula Vc, and which can be easily converted into the 4-pyrazole N-(het)arylamide compounds of formula VIII by reacting them with a suitable N-(het)arylamine.

Further embodiments of the present invention can be found in the claims, the description and the examples. It is to be understood that the features mentioned above and those still to be illustrated below of the subject matter of the invention can be applied not only in the respective given combination but also in other combinations without leaving the scope of the invention.

In the context of the present invention, the terms used generically are each defined as follows: The term "compound(s) according to the invention" in the context of the compounds of formulae I, II, III, IV, V, Va, Vb, Vc, VI, VII and VIII comprises the compound(s) as defined herein as well as stereoisomers, salts, tautomers or N-oxides thereof. The term "compound(s) of the present invention" is to be understood as equivalent to the term "compound(s) according to the invention".

N-oxides of the compounds of the present invention can only be obtained, if the compounds contain a nitrogen atom, which may be oxidized. This is principally the case for the compounds of formulae II, IV, V, Va, Vb, Vc, VI, VII and VIII, but not necessarily the case for compounds of formulae I and III. Accordingly, the term "compound(s) according to the invention" will only cover stereoisomers, salts and tautomers of the compounds of formulae I and III, if these compounds do not contain a nitrogen substituent, which would allow for the formation of an N-oxide. N-oxides may principally be prepared by standard methods, e.g. by the method described in Journal of Organometallic Chemistry 1989, 370, 17-31. However, it is preferred according to the invention that the intermediate compounds I, II, III and IV in the preparation of the compounds of formula V are not present in the form of the N-oxides. Furthermore, if it is desired to convert compounds of formula Va or Vb into compounds of formula Vc, or to convert compounds of formula Vc into compounds of formula VI, or to convert compounds of formula VI into compounds of formula VIII, it is also preferred that the compounds are not present in the form of N-oxides. On the other hand, under certain reaction conditions, it cannot be avoided that N-oxides are formed at least intermediary.

Stereoisomers of the compounds of formulae I, II, III, IV, V, Va, Vb, Vc, VI, VII and VIII will be present, if the compounds contain one or more centers of chirality in the substituents. In this case, the compounds will be present in the form of different enantiomers or diastereomers, if more than one center of chirality is present. The compounds of the present invention cover every possible stereoisomer, i.e. single enantiomers or diastereomers, as well as mixtures thereof. With regard to the compounds of formula V, it is noted that a center of chirality is also present in the generic formula, if the substituents R$^4$, R$^5$ and R$^6$ are different from each other. Said center of chirality is newly formed, when the compounds of formula V are prepared from the compounds of formula IV. In particular, the sp$^2$-hybridized carbon atom, to which the substituents R$^4$ and R$^5$ are attached in the compounds of formula IV, may be attacked by the reagent comprising the $R^6$ group from two sides, so that principally two configurations can be obtained at the resulting sp$^3$-hybridized carbon atom. The two possible stereoisomers of the compounds of formula V, V:SI-A and V:SI-B, which can be obtained according to the process according to the present invention, are depicted below.

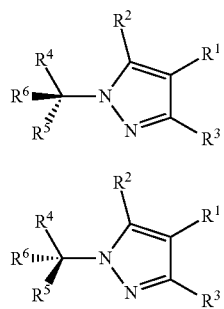

(V:SI-A)

(V:SI-B)

Analogous stereoisomers are also possible for the compounds of formula Va, Vb, Vc, VI and VIII. Thus, if the substituents $R^4$, $R^5$ and $R^6$ are different from each other, so that a center of chirality is present, the generic formulae V, Va, Vb, Vc, VI and VIII as used herein are in each case intended to cover two stereoisomers analogous to the two stereoisomers as depicted above. For reasons of clarity, it is not distinguished between the two stereoisomers of the generic formulae V, Va, Vb, Vc, VI and VIII throughout the specification. Instead the —CR$^4$R$^5$R$^6$ group is depicted without any indication regarding the three dimensional structure, but it is to be understood that the generic formulae V, Va, Vb, Vc, VI and VIII in each case embrace both possible stereoisomers, if the —CR$^4$R$^5$R$^6$ group is chiral due to different meanings of $R^4$, $R^5$ and $R^6$.

Geometric isomers of the compounds of the present invention are usually possible, if the compounds contain at least one carbon-carbon or carbon-nitrogen double bond because E- and Z-isomers of the compounds may then be present. The compounds of the present invention cover every possible geometric isomer, i.e. single E- or Z-isomers as well as mixtures thereof. With regard to the compounds of formulae II, III and IV, it is noted that a carbon-carbon double bond and/or a carbon-nitrogen double bond is already present in the generic formula. As in each case the E- and Z-isomers are both intended to be covered, the generic formulae are depicted with wavy lines to the substituents, which indicates that the two substituents at one sp$^2$-hybridized carbon atom may be present in each position. The possible E- and Z-isomers for the compounds of formula II (i.e. II:GI-A$^1$ and II:GI-B$^1$), III (i.e. III:GI-A$^2$ and III:GI-B$^2$) and IV (i.e. IV:GIA$^1$A$^2$, IV:GI-B$^1$A$^2$, IV:GI-A$^1$B$^2$ and IV:GI-B$^1$B$^2$) are depicted below.

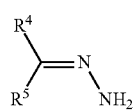

(II:GI-A$^1$)

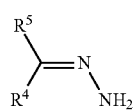

(II:GI-B$^1$)

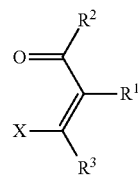

(III:GI-A$^2$)

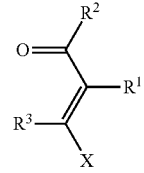

(III:GI-B$^2$)

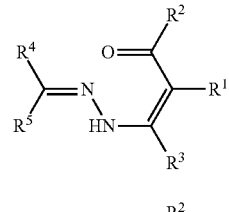

(IV:GI-A$^1$A$^2$)

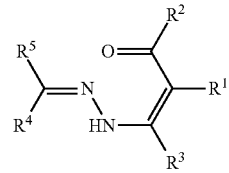

(IV:GI-B$^1$A$^2$)

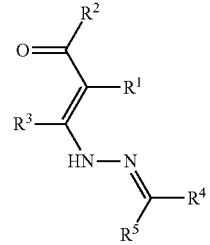

(IV:GI-A$^1$B$^2$)

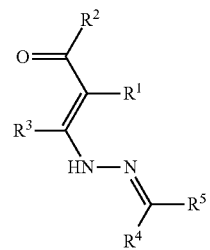

(IV:GI-B$^1$B$^2$)

Thus, if E- and Z-isomers are possible, the generic formulae II, III and IV as used herein are in each case intended to cover all geometric isomers as depicted above, which is indicated by the wavy lines to the substituents in the generic formulae.

Tautomers of the compounds of formulae I, II, III, IV, V, Va, Vb, Vc, VI, VII and VIII include keto-enol tautomers, imine-enamine tautomers, amide-imidic acid tautomers and the like. Such tautomerism is possible, e.g., for the generic formulae I, II, III, IV and VIII (if $R^{1N}$ is H). Depending on the substituents, which are defined for the compounds of formulae I, II, III, IV, V, Va, Vb, Vc, VI, VII and VIII, further tautomers may be formed. The compounds of the present invention cover every possible tautomer.

Depending on the acidity or basicity as well as the reaction conditions, the compounds of formulae I, II, III, IV, V, Va, Vb, Vc, VI, VII and VIII may be present in the form of salts. Such salts will typically be obtained by reacting the compound with an acid, if the compound has a basic functionality such as an amine, or by reacting the compounds with a base, if the compound as an acidic functionality such as a carboxylic acid group. For example, the compounds of formula Vb include 4-pyrazole carboxylic acid salts, wherein the cation stems from the base, with which the 4-pyrazole carboxylic acid has been reacted to give an anionic carboxylate. If a carboxylic acid group COOH is present in the form of a carboxylate, said anion may be referred to as $[C(O)O]^-$, wherein the negative charge is typically delocalized over the two oxygen atoms of the carboxylate group. On the other hand, the cationic charge of an ammonium cation, which may be formed from an amino group in the presence of an acid, is typically not delocalized.

Cations, which stem from a base, with which the compounds of the present invention are reacted, are e.g. alkali metal cations $M_a^+$, alkaline earth metal cations $M_{ea}^{2+}$ or ammonium cations $NR_4^+$, wherein the alkali metals are preferably sodium, potassium or lithium and the alkaline earth metal cations are preferably magnesium or calcium, and wherein the substituents R of the ammonium cation $NR_4^+$ are preferably independently selected from H, $C_1$-$C_{10}$-alkyl, phenyl and phenyl-$C_1$-$C_2$-alkyl.

Anions, which stem from an acid, with which the compounds of the present invention have been reacted, are e.g. chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate.

The compounds of the invention may be in the form of solids or liquids. If the compounds are present as solids, the compounds may be amorphous or may exist in one or more different crystalline forms. The compounds of the present invention cover mixtures of different crystalline forms of the respective compounds as well as amorphous or crystalline salts thereof.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 10, frequently 1 to 4, preferably 1 to 2 carbon atoms, wherein 1 carbon atom is substituted by an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluorethoxy, 2,2,2-trichloroethoxy, pentafluoroethoxy and the like.

The term "alkylthio "(alkylsulfanyl: alkyl-S—)" as used herein refers to a straight-chain or branched saturated alkyl group having 1 to 10 carbon atoms, preferably 1 to 4 carbon atoms (=$C_1$-$C_4$-alkylthio), more preferably 1 to 3 carbon atoms, which is attached via a sulfur atom.

The term "haloalkylthio" as used herein refers to an alkylthio group as mentioned above wherein the hydrogen atoms are partially or fully substituted by fluorine, chlorine, bromine and/or iodine.

The term "alkylsulfinyl" (alkylsulfoxyl: $C_1$-$C_6$-alkyl-S(=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl), more preferably 1 to 3 carbon atoms bonded through the sulfur atom of the sulfinyl group at any position in the alkyl group.

The term "haloalkylsulfinyl" as used herein refers to an alkylsulfinyl group as mentioned above wherein the hydrogen atoms are partially or fully substituted by fluorine, chlorine, bromine and/or iodine.

The term "alkylsulfonyl" (alkyl-S(=O)$_2$—) as used herein refers to a straight-chain or branched saturated alkyl group having 1 to 10 carbon atoms, preferably 1 to 4 carbon atoms (=$C_1$-$C_4$-alkylsulfonyl), preferably 1 to 3 carbon atoms, which is bonded via the sulfur atom of the sulfonyl group at any position in the alkyl group.

The term "haloalkylsulfonyl" as used herein refers to an alkylsulfonyl group as mentioned above wherein the hydrogen atoms are partially or fully substituted by fluorine, chlorine, bromine and/or iodine.

The term "alkylcarbonyl" refers to an alkyl group as defined above, which is bonded via the carbon atom of a carbonyl group (C=O) to the remainder of the molecule.

The term "haloalkylcarbonyl" refers to an alkylcarbonyl group as mentioned above, wherein the hydrogen atoms are partially or fully substituted by fluorine, chlorine, bromine and/or iodine.

The term "alkoxycarbonyl" refers to an alkylcarbonyl group as defined above, which is bonded via an oxygen atom to the remainder of the molecule.

The term "haloalkoxycarbonyl" refers to an alkoxycarbonyl group as mentioned above, wherein the hydrogen atoms are partially or fully substituted by fluorine, chlorine, bromine and/or iodine.

The term "alkenyl" as used herein denotes in each case a singly unsaturated hydrocarbon radical having usually 2 to 10, frequently 2 to 6, preferably 2 to 4 carbon atoms, e.g. vinyl, allyl (2-propen-1-yl), 1-propen-1-yl, 2-propen-2-yl, methallyl (2-methyl prop-2-en-1-yl), 2-buten-1-yl, 3-buten-1-yl, 2-penten-1-yl, 3-penten-1-yl, 4-penten-1-yl, 1-methyl-but-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkynyl" as used herein denotes in each case a singly unsaturated hydrocarbon radical having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "halocycloalkyl" as used herein and in the halocycloalkyl moieties of halocycloalkoxy and halocycloalkylthio denotes in each case a monocyclic cycloaliphatic radical having usually from 3 to 10 C atoms or 3 to 6 C atoms, wherein at least one, e.g. 1, 2, 3, 4, or 5 of the hydrogen atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkoxy" refers to a cycloalkyl group as defined above, which is bonded via an oxygen atom to the remainder of the molecule.

The term "halocycloalkoxy" refers to a halocycloalkyl group as defined above, which is bonded via an oxygen atom to the remainder of the molecule.

The term "cycloalkylthio" refers to a cycloalkyl group as defined above, which is bonded via a sulfur atom to the remainder of the molecule.

The term "halocycloalkylthio" refers to a halocycloalkyl group as defined above, which is bonded via a sulfur atom to the remainder of the molecule.

The term "cycloalkylalkyl" refers to a cycloalkyl group as defined above which is bonded via an alkyl group, such as a $C_1$-$C_5$-alkyl group or a $C_1$-$C_4$-alkyl group, in particular a methyl group (=cycloalkylmethyl), to the remainder of the molecule.

The term "cycloalkenyl" as used herein and in the cycloalkenyl moieties of cycloalkenyloxy and cycloalkenylthio denotes in each case a monocyclic singly unsaturated non-aromatic radical having usually from 3 to 10, e.g. 3, or 4 or from 5 to 10 carbon atoms, preferably from 3- to 8 carbon atoms. Exemplary cycloalkenyl groups include cyclopropenyl, cycloheptenyl or cyclooctenyl.

The term "halocycloalkenyl" as used herein and in the halocycloalkenyl moieties of halocycloalkenyloxy and halocycloalkenylthio denotes in each case a monocyclic singly unsaturated nonaromatic radical having usually from 3 to 10, e.g. 3, or 4 or from 5 to 10 carbon atoms, preferably from 3- to 8 carbon atoms, wherein at least one, e.g. 1, 2, 3, 4, or 5 of the hydrogen atoms, are replaced by halogen, in particular by fluorine or chlorine. Examples are 3,3-difluorocyclopropen-1-yl and 3,3-dichlorocyclopropen-1-yl.

The term "cycloalkenyloxy" refers to a cycloalkenyl group as defined above, which is bonded via an oxygen atom to the remainder of the molecule.

The term "halocycloalkenyloxy" refers to a halocycloalkenyl group as defined above, which is bonded via an oxygen atom to the remainder of the molecule.

The term "cycloalkenylthio" refers to a cycloalkenyl group as defined above, which is bonded via a sulfur atom to the remainder of the molecule.

The term "halocycloalkenylthio" refers to a halocycloalkenyl group as defined above, which is bonded via a sulfur atom to the remainder of the molecule.

The term "cycloalkenylalkyl" refers to a cycloalkenyl group as defined above which is bonded via an alkyl group, such as a $C_1$-$C_5$-alkyl group or a $C_1$-$C_4$-alkyl group, in particular a methyl group (=cycloalkenylmethyl), to the remainder of the molecule.

The term "carbocycle" or "carbocyclyl" includes in general a 3- to 12-membered, preferably a 3- to 8-membered or a 5- to 8-membered, more preferably a 5- or 6-membered mono-cyclic, non-aromatic ring comprising 3 to 12, preferably 3 to 8 or 5 to 8, more preferably 5 or 6 carbon atoms. Preferably, the term "carbocycle" covers cycloalkyl and cycloalkenyl groups as defined above.

The term "heterocycloalkyl" includes in general 3- to 8-membered, in particular 6-membered monocyclic saturated heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The term "heterocycloalkenyl" includes in general 3- to 8-membered, in particular 6-membered monocyclic singly unsaturated heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The term "heterocycle" or "heterocyclyl" includes in general 3- to 12-membered, preferably 3- to 8-membered or 5- to 8-membered, more preferably 5- or 6-membered, in particular 6-membered monocyclic heterocyclic non-aromatic radicals. The heterocyclic non-aromatic radicals usually comprise 1, 2, 3, 4, or 5, preferably 1, 2 or 3 heteroatoms selected from N, O and S as ring members, where S-atoms as ring members may be present as S, SO or $SO_2$. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "aryl" includes mono-, bi- or tricyclic aromatic radicals having usually from 6 to 14, preferably 6, 10, or 14 carbon atoms. Exemplary aryl groups include phenyl, naphthyl and anthracenyl. Phenyl is preferred as aryl group.

The term "hetaryl" includes monocyclic 5- or 6-membered heteroaromatic radicals comprising as ring members 1, 2, 3, or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4-, or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3-, or 5-oxazolyl, isoxazolyl, i.e. 3-, 4-, or 5-isoxazolyl, thiazolyl, i.e. 2-, 3- or 5-thiazolyl, isothiazolyl, i.e. 3-, 4-, or 5-isothiazolyl, pyrazolyl, i.e. 1-, 3-, 4-, or 5-pyrazolyl, i.e. 1-, 2-, 4-, or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocyclyloxy", "hetaryloxy", "aryloxy" and "phenoxy" refer to heterocyclyl, hetaryl and aryl as defined above and phenyl, which are bonded via an oxygen atom to the remainder of the molecule.

The terms "heterocyclylsulfonyl", "hetarylsulfonyl", "arylsulfonyl", and "phenylsulfonyl" refer to heterocyclyl, hetaryl and aryl as defined above, and phenyl, respectively, which are bonded via the sulfur atom of a sulfonyl group to the remainder of the molecule.

The terms "heterocyclylcarbonyl", "hetarylcarbonyl", "arylcarbonyl", and "phenylcarbonyl" refer to heterocyclyl, hetaryl and aryl as defined above, and phenyl, respectively, which are bonded via the carbon atom of a carbonyl group (C=O) to the remainder of the molecule.

The terms "heterocyclylalkyl" and "hetarylalkyl" refer to heterocyclyl or hetaryl, respectively, as defined above which are bonded via a $C_1$-$C_5$-alkyl group or a $C_1$-$C_4$-alkyl group, in particular a methyl group (=heterocyclylmethyl or hetarylmethyl, respectively), to the remainder of the molecule.

The terms "arylalkyl" and "phenylalkyl" refer to aryl as defined above and phenyl, respectively, which are bonded via $C_1$-$C_5$-alkyl group or a $C_1$-$C_4$-alkyl group, in particular a methyl group (=arylmethyl or phenylmethyl), to the remainder of the molecule, examples including benzyl, 1-phenylethyl, 2-phenylethyl, etc.

The term "arylalkoxy" and "benzyloxy" refer to arylalkyl as defined above and phenyl-$C_1$-alkyl, respectively, which are bonded via an oxygen atom, to the remainder of the molecule.

The terms "alkylene", "cycloalkylene", "heterocycloalkylene", "alkenylene", "cycloalkenylene", "heterocycloalkenylene" and "alkynylene" refer to alkyl, cycloalkyl, heterocycloalkyl, alkenyl, cycloalkenyl, heterocycloalkenyl and alkynyl as defined above, respectively, which are bonded to the remainder of the molecule, via two atoms, preferably via two carbon atoms, of the respective group, so that they represent a linker between two moieties of the molecule.

The term "cyclic moiety" can refer to any cyclic groups, which are present in the compounds of the present invention, and which are defined above, e.g. cycloalkyl, cycloalkenyl, carbocycle, heterocycloalkyl, heterocycloalkenyl, heterocycle, aryl, hetaryl and the like.

The remarks made below concerning preferred embodiments of the variables of the compounds of formulae I, II, III, IV, V, Va, Vb, Vc, VI, VII and VIII, and their subvariants are valid on their own as well as preferably in combination with each other as well as concerning the processes and the compounds according to the invention.

As already indicated above, the present invention relates in one embodiment to a process for preparing a pyrazole compound of formula V comprising the step of cyclizing a hydrazone substituted α,β-unsaturated carbonyl compound of formula IV by reacting it with a reagent comprising a $R^6$ group. Preferred embodiments of the invention relate to the preparation of the compounds of formula IV and to further conversions of specific compounds falling under the generic formula V, in particular Va, Vb, and Vc.

In view of the fact that the compounds of formula V of the present invention can be obtained according to the sequence comprising the steps (a) I→II, (b) II+111→IV, and (c) IV→V as described above and herein after, and in view of the fact that the compounds of formula V, if provided e.g. as compounds of formula Va and Vb, may be further converted according to the sequence comprising the steps (d) Va or Vb→Vc, (e) Vc→VI, and (f) VI+VII→VIII as described above and herein after, the substituents, which are preferred for the compounds of formula V will also be preferred for its precursors I, II, III and IV, provided that the substituents are present, and the same substituents will also be preferred for the compounds, which are obtainable from the compounds of formula Va, Vb and Vc, i.e. the compounds of formula VI and VIII, provided that the substituents are present.

The substituent $R^1$ is present in the 4-position of the pyrazole ring of the compounds of formula V. The substituent $R^1$ is also present in the precursors III and IV of the compounds of formula V.

In a preferred embodiment of the invention, R¹ is H, halogen, CN, NO₂, $C_1$-$C_{10}$-alkyl, which may be unsubstituted, may be partially or fully halogenated, or may be substituted by 1, 2 or 3 identical or different substituents $R^x$, $C(Y)OR^c$, $S(O)_mR^d$, $S(O)_mY^1R^d$, $C_3$-$C_{12}$-cycloalkyl, aryl, or hetaryl, wherein the cyclic moieties may be unsubstituted or may be substituted by 1, 2, 3, 4, or 5 identical or different substituents selected from the radicals $R^y$ and $R^x$;

wherein $R^c$ is H, $C_1$-$C_4$-alkyl or aryl-$C_1$-$C_4$-alkyl, or wherein $R^c$ together with the C(Y)O group forms a salt $[C(Y)O]^-NH_4^+$, $[C(Y)O]^-M^a$ or $[C(Y)O]^-\frac{1}{2}M_{ea}^{2+}$, wherein $M_a$ is an alkali metal and $M_{ea}$ is an alkaline earth metal;

wherein $R^d$ is $C_1$-$C_4$-alkyl, $C_3$-$C_6$-cycloalkyl, aryl or hetaryl;

wherein Y is O; and wherein $Y^1$ is O or $NR^{1a}$, wherein $R^{1a}$ is $C_1$-$C_4$-alkyl, $C_3$-$C_6$-cycloalkyl, aryl or hetaryl.

In a more preferred embodiment of the invention, R¹ is CN or $C(Y)OR^c$, wherein Y is O and $R^c$ is $C_1$-$C_4$-alkyl or benzyl, preferably ethyl or tert-butyl.

Compounds of formula V, wherein R¹ is $C(Y)OR^c$ with Y being O and $R^c$ being $C_1$-$C_4$-alkyl or aryl-$C_1$-$C_4$-alkyl, or wherein $R^c$ together with the C(O)O group forms a salt $[C(O)O]$—$NR_{4+}$, $[C(O)O]^-M_a^+$ or $[C(O)O]^-\frac{1}{2}M_{ea}^{2+}$, wherein $M_a$ is an alkali metal and $M_{ea}$ is an alkaline earth metal; and wherein the substituents R at the nitrogen atom are independently of each other selected from H, $C_1$-$C_{10}$-alkyl, phenyl and phenyl-$C_1$-$C_4$-alkyl, are referred to as compounds of formula Va.

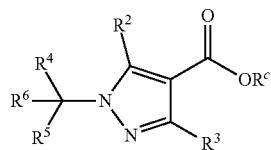

(Va)

Compounds of formula V, which correspond to compounds of formula Va, are preferred according to the present invention. The compounds of formula Va may be directly obtained from the compounds of formula IV according to the process of the invention, and they can easily be converted into the compounds of formula Vc to prepare compounds of formula VI II via the activated compounds of formula VI.

In a particular preferred embodiment of the invention, the compound of formula V is a compound of formula Va, wherein $R^c$ is $C_1$-$C_4$-alkyl or aryl-$C_1$-$C_4$-alkyl, preferably $C_1$-$C_4$-alkyl or benzyl.

Compounds of formula V, wherein R¹ is CN, are referred to as compounds of formula Vb.

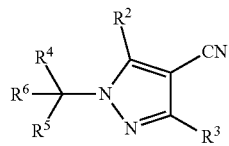

(Vb)

Compounds of formula V, which correspond to compounds of formula Vb, are preferred according to the present invention. The compounds of formula Vb may be directly obtained from the compounds of formula IV according to the process of the invention, and they can easily be converted into the compounds of formula Vc to prepare compounds of formula VI II via the activated compounds of formula VI.

Compounds of formula V, wherein R¹ is $C(Y)OR^c$ with Y being O and $R^c$ being H, are referred to as compounds of formula Vc.

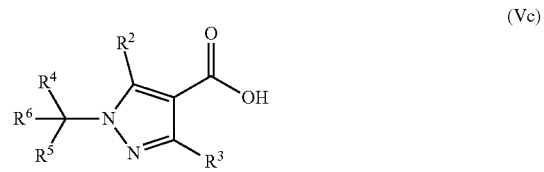

(Vc)

Compounds of formula V, which correspond to compounds of formula Vc, are preferred according to the present invention. In certain situations, the compounds of formula Vc may be directly obtained from the compounds of formula IV according to the process of the invention. However, it can be preferred to perform the cyclization of the compounds of formula IV with the carboxylic acid group being masked as an ester or a nitrile group. Thus, the compounds of formula Vc are may also be obtained from the compounds of formula Va or Vb as described above. The compounds of formula Vc then represent versatile reaction tools for the preparation of 4-pyrazole N-(het)arylamide compounds of formula VIII, as they can easily be activated for a subsequent amidation reaction to give the 4-pyrazole N-(het)arylamide compounds of formula VIII.

The substituent R² is present in the 5-position of the pyrazole ring of the compounds of formulae V, Va, Vb, Vc, VI and VIII. Furthermore, the substituent R² is present in the precursors III and IV of the compounds of formula V.

In a preferred embodiment of the invention R² is $C_1$-$C_{10}$-alkyl, which may be unsubstituted, may be partially or fully halogenated, or may be substituted by 1, 2 or 3 identical or different substituents $R^x$, $C_3$-$C_{12}$-cycloalkyl, aryl, or hetaryl, wherein the three last mentioned radicals may be unsubstituted or may be substituted by 1, 2, 3, 4, or 5 identical or different substituents selected from the radicals $R^y$ and $R^x$.

In a more preferred embodiment of the invention, R² is $C_1$-$C_4$-alkyl, which may be unsubstituted, or may be partially or fully halogenated.

It is even more preferred that R² is $CH_3$, $CH_2CH_3$ or fluoromethyl, and particularly preferred that R² is $CH_3$, $CF_2H$ or $CF_3$.

The substituent R³ is present in the 3-position of the pyrazole ring of the compounds of formulae V, Va, Vb, Vc, VI and VIII. Furthermore, the substituent R³ is present in the precursors III and IV of the compounds of formula V.

In a preferred embodiment of the invention R² is

H, $C_1$-$C_{10}$-alkyl, which may be unsubstituted, may be partially or fully halogenated, or may be substituted by 1, 2 or 3 identical or different substituents $R^x$, $C_3$-$C_{12}$-cycloalkyl, aryl, or hetaryl, wherein the cyclic moieties may be unsubstituted or may be substituted by 1, 2, 3, 4, or 5 identical or different substituents selected from the radicals $R^y$ and $R^x$.

In a more preferred embodiment of the invention, R³ is H.

As already indicated above, the process according to the present invention is particularly advantageous for regioselectively preparing N-substituted pyrazole compounds, which are 3- or 5-substituted or substituted with different substituents in the 3- and 5-position. Thus, compounds of formula V, wherein R³ and R² are different from each other are particularly preferred. It is particularly preferred that one of $R^3$ and $R^2$ is H and the other one is different from H. Alternatively, it can be preferred that $R^3$ and $R^2$ are both different from H, and different from each other.

Compounds of formula V, wherein $R^3$ is different from H and wherein $R^2$ is H, are to be understood as 3-substituted N-substituted pyrazole compounds and are referred to as compounds of formula V.3-$R^3_{subst}$.5-H, wherein $R^3_{subst}$ refers to a substituent defined for $R^3$, which is other than H.

Compounds of formula V, wherein $R^3$ is H and wherein $R^2$ is different from H, are to be understood as 5-substituted N-substituted pyrazole compounds and are referred to as compounds of formula V.3-H.5-$R^2_{subst}$, wherein $R^2_{subst}$ refers to a substituent defined for $R^2$, which is other than H.

Compounds of formula V, wherein $R^3$ and $R^2$ are different from H and different from each other, are to be understood as 3- and 5-substituted N-substituted pyrazole compounds, wherein the substituents in the 3- and 5-position are different from each other. Such compounds are referred to as compounds of formula V.3-$R^3_{subst}$.5-$R^2_{subst}$, wherein $R^3_{subst}$ refers to a substituent defined for $R^3$, which is other than H, and wherein $R^2_{subst}$ refers to a substituent defined for $R^2$, which is other than H, with the proviso that $R^3_{subst}$ and $R^2_{subst}$ are different from each other. The compounds are depicted below.

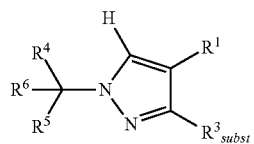

(V.3-$R^3_{subst}$.5-H)

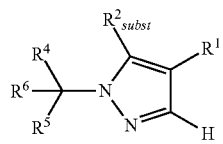

(V.3-$R^3_{subst}$.5-H)

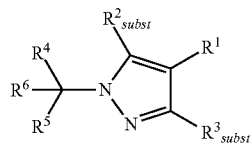

(V.3-$R^3_{subst}$.5-$R^2_{subst}$)

The meanings for $R^2$ and $R^3$, i.e. that one of $R^3$ and $R^2$ is H and the other one is different from H, or that $R^3$ and $R^2$ are both different from H, and different from each other, are also preferred for the precursors III and IV as well as for the compounds of formulae Va, Vb, Vc, VI and VIII.

Compounds of formula V.3-H.5-$R^2_{subst}$ and analogously substituted compounds of formulae III, IV, Va, Vb, Vc, VI and VIII are particularly preferred according to the present invention.

The substituents $R^4$ and $R^5$ are present in the compounds of formulae I, II, IV, V, Va, Vb, Vc, VI and VIII.

In one preferred embodiment of the invention, $R^4$ is selected from $C_1$-$C_{10}$-alkyl, which may be unsubstituted, may be partially or fully halogenated, or may be substituted by 1, 2 or 3 identical or different substituents $R^x$, and $C_3$-$C_{10}$-cycloalkyl, which may be unsubstituted or may be substituted by 1, 2, 3, 4, or 5 identical or different substituents $R^y$; and $R^5$ is selected from $C_1$-$C_{10}$-alkyl, which may be unsubstituted, may be partially or fully halogenated, or may be substituted by 1, 2 or 3 identical or different substituents $R^x$, and $C_3$-$C_{10}$-cycloalkyl, which may be unsubstituted or may be substituted by 1, 2, 3, 4, or 5 identical or different substituents $R^y$.

In a more preferred embodiment of this embodiment, $R^4$ is selected from $C_1$-$C_4$-alkyl, which may be unsubstituted, may be partially or fully halogenated, or may be substituted by 1 or 2 identical or different substituents $R^x$, wherein $R^x$ is selected from CN and C(O)NH$_2$, and $C_3$-$C_6$-cycloalkyl, which may be unsubstituted or may be substituted by 1, 2 or 3 identical or different substituents $R^y$, wherein $R^y$ is selected from halogen, CN and C(O)NH$_2$; and $R^5$ is selected from $C_1$-$C_4$-alkyl, which may be unsubstituted, may be partially or fully halogenated, or may be substituted by 1 or 2 identical or different substituents $R^x$, wherein $R^x$ is selected from CN and C(O)NH$_2$, and $C_3$-$C_6$-cycloalkyl, which may be unsubstituted or may be substituted by 1, 2 or 3 identical or different substituents $R^y$, wherein $R^y$ is selected from halogen, CN and C(O)NH$_2$.

In an even more preferred embodiment of this embodiment, $R^4$ is selected from $C_1$-$C_4$-alkyl, which may be unsubstituted, may be partially or fully halogenated, or may be substituted by 1 or 2 identical or different substituents $R^x$, wherein $R^x$ is selected from CN and C(O)NH$_2$, and $C_3$-$C_6$-cycloalkyl, which may be unsubstituted or may be substituted by 1, 2 or 3 identical or different substituents $R^y$, wherein $R^y$ is selected from halogen, CN and C(O)NH$_2$; and $R^5$ is selected from $C_1$-$C_2$-alkyl, which may be unsubstituted, may be partially or fully halogenated, or may be substituted by 1 or 2 identical or different substituents $R^x$, wherein $R^x$ is selected from CN and C(O)NH$_2$, and $C_3$-$C_4$-cycloalkyl, which may be unsubstituted or may be substituted by 1, 2 or 3 identical or different substituents $R^y$, wherein $R^y$ is selected from halogen, CN and C(O)NH$_2$.

It is particularly preferred according to this embodiment of the present invention that $R^4$ and $R^5$ are different from each other. For example, $R^5$ may be $C_1$-$C_2$-alkyl, which is unsubstituted, or $C_3$-$C_4$-cycloalkyl, which is unsubstituted, while $R^4$ may be $C_1$-$C_4$-alkyl, which may be unsubstituted, or partially or fully halogenated, or substituted with 1 or 2 identical or different substituents $R^x$ selected from CN and C(O)NH$_2$, or may be $C_3$-$C_6$-cycloalkyl, which may preferably be substituted with 1, 2 or 3 identical or different substituents $R^y$ selected from halogen, CN and C(O)NH$_2$.

Most preferably, $R^5$ is CH$_3$, while $R^4$ is $C_1$-$C_4$-alkyl, $C_1$-$C_2$-haloalkyl, or $C_3$-cycloalkyl, wherein the cycloalkyl group is preferably substituted with one substituent selected from CN and C(O)NH$_2$. Suitable combinations of $R^5$ and $R^4$ may thus e.g. be CH$_3$/i-Pr or CH$_3$/1-CN-cC$_3$H$_4$.

In another preferred embodiment of the invention, $R^4$ and $R^5$ together with the carbon atom to which they are attached form a 3- to 12-membered non-aromatic carbocycle, which may be partially or fully substituted by $R^j$.

In a more preferred embodiment of this embodiment,

R$^4$ and R$^5$ together with the carbon atom to which they are attached form a 3- to 12-membered non-aromatic, saturated carbocycle, which may be partially or fully substituted by R$^j$, wherein R$^j$ is selected from halogen, CN and C(O)NH$_2$.

In an even more preferred embodiment of this embodiment,

R$^4$ and R$^5$ together with the carbon atom to which they are attached form a 3- to 6-membered non-aromatic, saturated carbocycle, which may be partially or fully substituted by R$^j$, wherein R$^j$ is selected from halogen, CN and C(O)NH$_2$.

It is particularly preferred according to this embodiment of the present invention that R$^4$ and R$^5$ together with the carbon atom to which they are attached form a 6-membered carbocycle, which is partially or fully halogenated, preferably fluorinated. Thus, R$^4$ and R$^5$ may together represent e.g. —CH$_2$CH$_2$CF$_2$CH$_2$CH$_2$—.

The substituent R$^6$ is present in the compounds of formulae V, Va, Vb, Vc, VI and VIII and in the reagent, with which the compound of formula IV is reacted to give the compound of formula V.

In one preferred embodiment of the invention, R$^6$ is selected from H, CN and C$_1$-C$_2$-fluoroalkyl. More preferably R$^6$ is selected from H, CN, CHF$_2$ and CF$_3$, and most referably, R$^6$ is H.

Compounds of formula V, wherein R$^6$ is H may be referred to as compounds of formula V.R$^6$—H.

Compounds of formula V.R$^6$—H and analogously substituted compounds of formulae Va, Vb, Vc, VI and VIII are particularly preferred according to the present invention.

Compounds of formula V.3-H.5-R$^2_{subst}$, wherein R$^6$ is H, i.e. compounds of formula V.3-H.5-R$^2_{subst}$.R$^6$—H and analogously substituted compounds of formulae III, IV, Va, Vb, Vc, VI and VIII are particularly preferred according to the present invention.

As already indicated above, a center of chirality may be formed upon the formation of the compounds of formula V by reacting a compound of formula IV with a reagent comprising a R$^6$ group, if the substituents R$^4$ and R$^5$ of the compound of formula IV and R$^6$ are different from each other. If two or more of the three substituents R$^4$, R$^5$ and R$^6$ are identical, no center of chirality will be formed upon the formation of the compounds of formula V. It is particularly preferred according to the present invention that R$^4$, R$^5$ and R$^6$ are different from each other, so that a center of chirality is formed. If a center of chirality is formed, it is preferred that the two possible configurations of the center of chirality are formed in equal amounts. Thus, the formation of the compounds of formula V according to the present invention is usually not stereoselective, but a mixture, preferably a racemic mixture, of the two possible stereoisomers is obtained. If a center of chirality is present at the —CR$^4$R$^5$R$^6$ group of the compounds of formula V, generic formula V is therefore preferably intended to cover a mixture of the two possible stereoisomers. If no further centers of chirality are present in the compound, the stereoisomers are enantiomers, otherwise the stereoisomers may be diastereoisomers. The same considerations also apply for generic formulae Va, Vb, Vc, VI and VIII.

With regard to the reagent comprising the R$^6$ group, which is reacted with the compounds of formula IV to give the compounds of formula V, the following is noted.

For R$^6$ being H, it is preferred that the reagent is present in the form of "reagent-R$^6$", and transfers H as a hydride. In certain situations, it can also be preferred that the reagent transfers H as a hydrogen radical.

In one preferred embodiment of the invention, the reagent comprising H as the R$^6$ group is a reducing agent. Preferably, the reducing agents are selected from (ia) ionic hydride donors selected from the group consisting of complex hydrides of boron and aluminum, (ib) non-ionic hydride donors selected from the group consisting of dihydrogen, which is particularly preferably used in combination with a metal catalyst, Hantzsch ester, 1,4-dihydrobenzol, isopropanol, formic acid, and ammonium formate, and (ic) electron donors, which are used in combination with protons, wherein the electrons are donated by a cathode or a metal selected from Li, Na, K, Mg, Zn, Fe and Al.

Ionic hydride donors are described in the following and are particularly preferred according to the present invention.

Although the term "ionic" indicates that the "ionic hydride donors" have an ionic structure, ionic hydride donors principally belong to the group of reagents, which comprise R$^6$, i.e. H, covalently bonded, and may thus be referred to as "reagent-H", which may react with compounds of formula IV. However, an ionic structure is nevertheless present in ionic hydride donors because the reagent, which comprises H covalently bonded, is itself ionic, preferably anionic, i.e. in the form "[reagent-H]$^-$", so that the reagent is typically provided in the form of a salt "Ct+[reagent-H]$^-$", wherein Ct$^{+0}$ represents a cation, e.g. an alkali metal cation, and "[reagent-H]$^-$" is as defined above. Preferably, the ionic hydride donor is a negatively charged hydrido complex of a metal, which is provided in the form of a salt and is capable of transferring H as a hydride.

In a particular preferred embodiment of the invention, the ionic hydride donor is selected from the group consisting of complex hydrides of boron and aluminium.

The term "complex hydride of boron or aluminum" refers to hydrido complexes of boron or aluminum. Thus, R$^6$ being H may be covalently bonded to a boron or aluminum atom to give a hydrido complex, which is capable of transferring H as a hydride as indicated above. Preferably, the boron or aluminum complex is negatively charged due to the presence of four substituents, of which one is H as the group R$^6$, which can be transferred in the form of a hydride, and the three remaining substituents can independently of each other e.g. be selected from the group consisting of H, C$_1$-C$_4$-alkyl, C$_1$-C$_4$-alkoxy and CN. Thus, the complex may be described by the formula "[reagent-H]$^-$" defined above. Typically, the anionic hydrido complex of boron or aluminum is combined with a cation in the form of a salt, e.g. according to the formula "Ct$^+$[reagent-H]$^-$" mentioned above. The cation Ct$^+$ is typically an alkali metal ion, which is preferably Na$^+$ or Li$^+$.

Preferred complex hydrides of boron and aluminum include Na$^+$[BH$_4$]$^-$, Na$^+$[B(CN)H$_3$]$^-$, Na$^+$[BH(OAc)$_3$]$^-$, Li$^+$[AlH$_4$]$^-$, Li$^+$[Al*H (O tert-Bu)$_4$]$^-$, Li$^+$[BH$_4$]$^-$, Li$^+$[BHEt$_3$]$^-$, Li$^+$[BH(sec-Bu)$_3$]$^-$ and the like. Complex hydrides of aluminum are usually preferred, if a high reactivity of the reagent comprising the R$^6$ group is desired. Complex hydrides of boron are typically milder reducing agents. For the purposes of the present invention, complex hydrides of boron are usually preferred. Most preferably, the reagent comprising R$^6$ is Na$^+$[BH$_4$]$^-$ or Na$^+$[BCNH$_3$]$^-$, particularly preferably Na$^+$[B(CN)H$_3$]$^-$. The reagent Na$^+$[B(CN)H$_3$]$^-$ has the following structure.

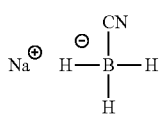

Typically, Na⁺[B(CN)H₃]⁻ is also referred to as NaB(CN)H₃ or NaBH₃CN. Similarly, also the other complex hydrides of boron and aluminium listed above are often referred to by a molecular formula without indicating charges.

The structures of other complex hydrides of boron and aluminum including the ones listed above are analogous.

In the following, non-ionic hydride donors are described.

The term "non-ionic hydride donor" refers to reagents comprising a $R^6$ group being H, which are non-ionic and typically belong to the group of reagents, which comprise $R^6$, i.e. H, covalently bonded. Preferably, the non-ionic hydride donor is a non-charged hydrogen source, which is capable of transferring H in the form of a hydride, and usually also transfers a proton, so that a dihydrogen molecule is transferred in the end. If the reagents transfer H in the form of a hydride, they may again be considered as "reagent-H" as described above.

As used herein, the term "non-ionic hydride donor" also covers dihydrogen because the result of a hydrogenation reaction with dihydrogen may principally also be seen in the transfer of a hydride and a proton. However, such a hydrogenation may of course also take place as such that two non-charged hydrogen atoms, i.e. hydrogen radicals, are transferred.

In a particular preferred embodiment of the invention, the reagent comprising the $R^6$ group is a non-ionic hydrogen donor, which is selected from the group consisting of Hantzsch ester, 1,4-dihydrobenzol, isopropanol, formic acid, ammonium formate, and dihydrogen.

Hantzsch ester, 1,4-dihydrobenzol, isopropanol, formic acid, and ammonium formate are also known in the art as "transfer hydrogenation reagents". They can be considered as hydrogen sources as they can transfer a hydride ion and a proton. Reactions with these transfer hydrogenation reagents can typically be carried out metal-free, i.e. in the absence of a metal catalyst.

The reaction with dihydrogen (H₂) as reducing agent is preferably performed in combination with a metal catalyst. A skilled person knows suitable metal catalysts to be used in combination with dihydrogen. Examples of suitable metal catalysts are provided further below.

In the following, the reductive cyclization, which is performed with protons in combination with electrons provided by an electrode or by a metal, is described.

The protons are preferably provided by protic solvents, preferably water or an alcohol such as methanol, ethanol or isopropanol, and the electrons are generated from an electrode (cathode) or a suitable metal, preferably a metal selected from Li, Na, K, Mg, Fe and Al.

For $R^6$ being different from H, the reagent may be present in a form, wherein $R^6$ is covalently bonded, i.e. in the form of "reagent-$R^6$", or in the form of a salt with $R^6$ representing the anion, i.e. in the form of "[reagent]+[$R^6$]⁻".

In one preferred embodiment of the invention, the reagent comprising the $R^6$ group being different from H is an organometallic reagent, wherein $R^6$ is selected from $C_1$-$C_6$-fluoroalkyl, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_2$-alkyl, $C_3$-$C_6$-cycloalkenyl, $C_3$-$C_6$-cycloalkenyl-$C_1$-$C_2$-alkyl, heterocyclyl, heterocyclyl-$C_1$-$C_2$-alkyl, aryl, aryl-$C_1$-$C_2$-alkyl, hetaryl, hetaryl-$C_1$-$C_2$-alkyl, wherein the carbon chains or cyclic moieties may be unsubstituted, partially or fully substituted by identical or different substituents $R^x$. Preferably, the reagent comprising the $R^6$ group is an organometallic reagent, wherein $R^6$ is selected from $C_1$-$C_4$-fluoroalkyl, $C_1$-$C_4$-alkyl, aryl, arylmethyl and allyl, and wherein $R^6$ is particularly preferably selected from $C_1$-$C_2$-fluoroalkyl, in particular from $CH_2F$ and $CF_3$.

Preferably, the organometallic reagent comprises a metal M selected from Li, Mg, Cu, Zn, Si, Mn or In. Depending on the metal, the organometallic reagent may be considered as "reagent-$R^6$" (e.g. M-$R^6$) or "[reagent]+[$R^6$]⁻" (e.g. [M]+[$R^6$]⁻), but should preferably be considered as "reagent-$R^6$" because the above listed metals are known to form covalent bonds rather than ionic bonds with organic groups as listed above for $R^6$.

Preferred organometallic reagents according to the present invention include Grignard reagents, cuprate reagents, allyl silanes (Hosomi-Sakurai reagents) and fluoroalkyl silanes (e.g. Ruppert's reagent).

Particularly preferably, the organometallic reagent is Ruppert's reagent, i.e. trimethyl(trifluoromethyl)silane, which transfers $CF_3$ as a $R^6$ group.

In another preferred embodiment of the invention, the reagent comprising the $R^6$ group being different from H is a nucleophilic reagent of formula H—$R^6$, $M_a^+R^{6-}$ or $½M_{ea}^{2+}R^{6-}$, wherein $M_a$ is an alkaline metal and $M_{ae}$ is an alkaline earth metal, and wherein $R^6$ is selected from CN, $OR^a$, $SR^a$, $NR^eR^f$, and groups of the general formula (i)

wherein $R^a$, $R^e$, $R^f$, $R^r$, $R^s$ and $R^t$ are as defined above.

The wavy line in the groups of the general formula (i) indicated the position, where the group (i) may be connected to H according to formula H—$R^6$, or may have been deprotonated to give a salt of formula $M_a^+R^{6-}$ or $½M_{ea}^{2+}R^{6-}$. If the group (i) is present in deprotonated, i.e. anionic, form, the negative charge may be delocalized over the 1,3-di(thio)carbonyl system. It is noted, however, that the carbon atom between the two (thio)carbonyl groups will nevertheless be the nucleophilic position of the group (i). Preferred groups (i) are 1,3-dicarbonyl compounds, which have been deprotonated in the 2-position with a suitable base, and are thus present in anionic form in the combination with a cation, which stems from the base. The reagent comprising group (i) as group $R^6$ may thus preferably be represented by the formula $M_a^+R^{6-}$ or $½M_{ea}^{2+}R^{6-}$, which may both be considered as falling under the above formula "[reagent]+[$R^6$]⁻", and wherein $M_a$ may e.g. be Li, K or Na, and $M_{ea}$ may e.g. be Mg or Ca. It is noted that, if the reagent comprising group (i) as group $R^6$ falls under formula H—$R^6$, it may be considered as a "reagent-$R^6$" described above with "reagent" being H.

Preferred groups $OR^a$ include $C_1$-$C_4$-alkoxy and $C_3$-$C_6$-cycloalkoxy.

Preferred groups $SR^a$ include $C_1$-$C_4$-alkylthio and $C_3$-$C_6$-cycloalkylthio.

Preferred groups $NR^eR^f$ include $C_1$-$C_4$-alkylamino, $C_1$-$C_4$-dialkylamino, wherein the alkyl chains may have an identical or different length, morpholine, piperazine and N-methylpiperazine.

For the group $R^6$ being $OR^a$, $SR^a$ or $NR^eR^f$, the reagent comprising the $R^6$ group can either be represented by the formula H—$R^6$, which can be considered as falling under the above formula "reagent-$R^6$", or by any one of formulae $M_a+R^{6-}$ and/$2M_{ea}^{2+}R^{6-}$, which may both be considered as falling under the above formula "[reagent]+$[R^6]^-$", and wherein $M_a$ may e.g. be Li, K or Na, and $M_{ea}$ may e.g. be Mg or Ca. For the reagent comprising $OR^a$ or $SR^a$ as $R^6$ group, it can be preferred that the reagent is present in the form of $M_a^+R^{6-}$ or $\frac{1}{2}M_{ea}^{2+}R^{6-}$. For the reagent comprising $NR^eR^f$ as $R^6$ group, it can be preferred that the reagent is present in the form of H—$R^6$ because H—$NR^eR^f$ also has a nucleophilic reactivity, if it is used in protonated form.

For the $R^6$ group being CN, similar considerations apply. Thus, the reagent comprising CN as the $R^6$ group can either be represented by the formula H—$R^6$, which can be considered as falling under the above formula "reagent-$R^6$", or by any one of formulae $M_a+R^{6-}$ and $\frac{1}{2}M_{ea}^{2+}R^{6-}$, which may both be considered as falling under the above formula "[reagent]+$[R^6]^-$", and wherein $M_a$ may e.g. be Li, K or Na, and $M_{ea}$ may e.g. be Mg or Ca. If $R^6$ is CN, the reagent comprising the $R^6$ group is preferably HCN, NaCN or KCN.

It is noted that it is particularly preferred for the reagent being a nucleophilic reagent comprising the $R^6$ group that $R^6$ is CN. NaCN is a particularly preferred reagent comprising a group $R^6$.

The following embodiments regarding the reagent comprising a $R^6$ group are preferred according to the present invention.

In one preferred embodiment, the $R^6$ group of the reagent comprising the $R^6$ group is H, and the reagent comprising the $R^6$ group is selected from
(ia) ionic hydride donors selected from the group consisting of complex hydrides of boron and aluminum, or
(ib) non-ionic hydride donors selected from the group consisting of dihydrogen, which is preferably used in combination with a metal catalyst, Hantzsch ester, 1,4-dihydrobenzol, isopropanol, formic acid, and ammonium formate.

In another preferred embodiment, the $R^6$ group of the reagent comprising the $R^6$ group is H, and the reagent comprising the $R^6$ group is selected from
(ia) ionic hydride donors selected from the group consisting of complex hydrides of boron and aluminum, or
(ib) dihydrogen, which used in combination with a metal catalyst.

With regard to option (a), the following embodiments are preferred.

In one preferred embodiment, the $R^6$ group of the reagent comprising the $R^6$ group is H, and the reagent comprising the $R^6$ group is an alkali salt of a negatively charged boron or aluminum complex, wherein the boron or aluminum is substituted by four substituents, of which at least one is H, and the three remaining substituents are independently selected from the group consisting of H, $C_1$-$C_4$-alkyl, $C_1$-$C_4$-alkoxy, and CN.

In a more preferred embodiment, the $R^6$ group of the reagent comprising the $R^6$ group is H, and the reagent comprising the $R^6$ group is a sodium salt of a negatively charged boron complex, wherein the boron is substituted by four substituents, of which at least one is H, and the three remaining substituents are independently selected from the group consisting of H, $C_1$-$C_4$-alkyl, $C_1$-$C_4$-alkoxy, and CN.

In a particularly preferred embodiment, the $R^6$ group of the reagent comprising the $R^6$ group is H, and the reagent comprising the $R^6$ group is $Na^+[B(CN)H_3]^-$.

With regard to option (b), the following embodiments are preferred.

In one preferred embodiment, the $R^6$ group of the reagent comprising the $R^6$ group is H, and the reagent comprising the $R^6$ group is dihydrogen ($H_2$), which is used in combination with a metal catalyst.

In a more preferred embodiment, the $R^6$ group of the reagent comprising the $R^6$ group is H, and the reagent comprising the $R^6$ group is dihydrogen, which is used in combination with a metal catalyst selected from the group consisting of Rayney-Nickel, Pd/C, Pt/C, and $PtO_2$.

In an even more preferred embodiment, the $R^6$ group of the reagent comprising the $R^6$ group is H, and the reagent comprising the $R^6$ group is dihydrogen, which is used in combination with a metal catalyst selected from the group consisting of Rayney-Nickel, Pd/C, Pt/C, and $PtO_2$, and wherein the dhydrogen is applied with a pressure, which does not exceed 100 bar, and preferably does not exceed 50 bar.

In an even more preferred embodiment, the $R^6$ group of the reagent comprising the $R^6$ group is H, and the reagent comprising the $R^6$ group is dihydrogen, which is used in combination with a metal catalyst selected from the group consisting of Rayney-Nickel, Pd/C, Pt/C, and $PtO_2$, and in combination with a catalytic amount of an acid, and wherein the dihydrogen is applied with a pressure, which does not exceed 100 bar, and preferably does not exceed 50 bar.

In an even more preferred embodiment, the $R^6$ group of the reagent comprising the $R^6$ group is H, and the reagent comprising the $R^6$ group is dihydrogen, which is used in combination with a metal catalyst selected from the group consisting of Rayney-Nickel, Pd/C, Pt/C, and $PtO_2$, and in combination with a catalytic amount of an acid, which is selected from aromatic sulfonic acids such as toluene sulfonic acid; alkylsulfonic acids, such as methyl sulfonic acid; aromatic carboxylic acids such as benzoic acid; alkylcarboxylic acids such as acetic acid; haloalkylcarboxylic acids such as trifluoroacetic acid, and mineral acids such as hydrogen chloride or sulfuric acid in methanol, and wherein the dihydrogen is applied with a pressure, which does not exceed 100 bar, and preferably does not exceed 50 bar.

In an even more preferred embodiment, the $R^6$ group of the reagent comprising the $R^6$ group is H, and the reagent comprising the $R^6$ group is dihydrogen, which is used in combination with a metal catalyst selected from the group consisting of Rayney-Nickel, Pd/C, Pt/C, and $PtO_2$, and in combination with a catalytic amount of an acid, which is selected from HCl, $H_2SO_4$, and trifluoracetic acid, and wherein the dihydrogen is applied with a pressure, which does not exceed 100 bar, and preferably does not exceed 50 bar.

Summarizing, the reagent comprising the $R^6$ group, which is reacted with the compounds of formula IV to give the compounds of formula V, may be
  a reducing agent, which may preferably be an ionic hydride donor, and is particularly preferably $Na^+[B(CN)H_3]^-$; or
  an organometallic reagent, which may preferably be a silane, such as an allyl silane or a fluoroalkylsilane, and is particularly preferably Ruppert's reagent; or
  a nucleophilic reagent, which may preferably be selected from HCN, or a salt, such as NaCN, or KCN, and is particularly preferably NaCN.

In summary, the following combinations of substituents are preferred in the compounds of formula V and its precursors or the reagents used in the process of the present invention.

Table 1
Combination, in which $R^1$ is H, $R^2$ is $CH_3$, $R^3$ is H and the combination of $R^4$ and $R^5$ corresponds in each case to one row of Table A Table 2
Combination, in which $R^1$ is H, $R^2$ is $CH_3$, $R^3$ is $C_3H_5$ and the combination of $R^4$ and $R^5$ corresponds in each case to one row of Table A Table 3
Combination, in which $R^1$ is H, $R^2$ is $CH_3$, $R^3$ is $C_6H_5$ and the combination of $R^4$ and $R^5$ corresponds in each case to one row of Table A Table 4
Combination, in which $R^1$ is H, $R^2$ is $C_3H_5$, $R^3$ is H and the combination of $R^4$ and $R^5$ corresponds in each case to one row of Table A Table 5
Combination, in which $R^1$ is H, $R^2$ is $C_3H_5$, $R^3$ is $CH_3$ and the combination of $R^4$ and $R^5$ corresponds in each case to one row of Table A Table 6
Combination, in which $R^1$ is H, $R^2$ is $C_3H_5$, $R^3$ is $C_6H_5$ and the combination of $R^4$ and $R^5$ corresponds in each case to one row of Table A Table 7
Combination, in which $R^1$ is H, $R^2$ is $C_6H_5$, $R^3$ is H and the combination of $R^4$ and $R^5$ corresponds in each case to one row of Table A Table 8
Combination, in which $R^1$ is H, $R^2$ is $C_6H_5$, $R^3$ is $CH_3$ and the combination of $R^4$ and $R^5$ corresponds in each case to one row of Table A Table 9
Combination, in which $R^1$ is H, $R^2$ is $C_6H_5$, $R^3$ is $C_3H_5$ and the combination of $R^4$ and $R^5$ corresponds in each case to one row of Table A Table 10
Combination, in which $R^1$ is H, $R^2$ is $CF_2H$, $R^3$ is H and the combination of $R^4$ and $R^5$ corresponds in each case to one row of Table A Table 11
Combination, in which $R^1$ is H, $R^2$ is $CF_2H$, $R^3$ is $CH_3$ and the combination of $R^4$ and $R^5$ corresponds in each case to one row of Table A Table 12
Combination, in which $R^1$ is H, $R^2$ is $CF_2H$, $R^3$ is $C_3H_5$ and the combination of $R^4$ and $R^5$ corresponds in each case to one row of Table A Table 13
Combination, in which $R^1$ is H, $R^2$ is $CF_2H$, $R^3$ is $C_6H_5$ and the combination of $R^4$ and $R^5$ corresponds in each case to one row of Table A Table 14
Combination, in which $R^1$ is H, $R^2$ is $CF_3$, $R^3$ is H and the combination of $R^4$ and $R^5$ corresponds in each case to one row of Table A Table 15
Combination, in which $R^1$ is H, $R^2$ is $CF_3$, $R^3$ is $CH_3$ and the combination of $R^4$ and $R^5$ corresponds in each case to one row of Table A Table 16
Combination, in which $R^1$ is H, $R^2$ is $CF_3$, $R^3$ is $C_3H_5$ and the combination of $R^4$ and $R^5$ corresponds in each case to one row of Table A Table 17
Combination, in which $R^1$ is H, $R^2$ is $CF_3$, $R^3$ is $C_6H_5$ and the combination of $R^4$ and $R^5$ corresponds in each case to one row of Table A Table 18
Combination, in which $R^1$ is F, $R^2$ is $CH_3$, $R^3$ is H and the combination of $R^4$ and $R^5$ corresponds in each case to one row of Table A Table 19
Combination, in which $R^1$ is F, $R^2$ is $CH_3$, $R^3$ is $C_3H_5$ and the combination of $R^4$ and $R^5$ corresponds in each case to one row of Table A Table 20
Combination, in which $R^1$ is F, $R^2$ is $CH_3$, $R^3$ is $C_6H_5$ and the combination of $R^4$ and $R^5$ corresponds in each case to one row of Table A Table 21
Combination, in which $R^1$ is F, $R^2$ is $C_3H_5$, $R^3$ is H and the combination of $R^4$ and $R^5$ corresponds in each case to one row of Table A Table 22
Combination, in which $R^1$ is F, $R^2$ is $C_3H_5$, $R^3$ is $CH_3$ and the combination of $R^4$ and $R^5$ corresponds in each case to one row of Table A Table 23
Combination, in which $R^1$ is F, $R^2$ is $C_3H_5$, $R^3$ is $C_6H_5$ and the combination of $R^4$ and $R^5$ corresponds in each case to one row of Table A Table 24
Combination, in which $R^1$ is F, $R^2$ is $C_6H_5$, $R^3$ is H and the combination of $R^4$ and $R^5$ corresponds in each case to one row of Table A Table 25
Combination, in which $R^1$ is F, $R^2$ is $C_6H_5$, $R^3$ is $CH_3$ and the combination of $R^4$ and $R^5$ corresponds in each case to one row of Table A Table 26
Combination, in which $R^1$ is F, $R^2$ is $C_6H_5$, $R^3$ is $C_3H_5$ and the combination of $R^4$ and $R^5$ corresponds in each case to one row of Table A Table 27
Combination, in which $R^1$ is F, $R^2$ is $CF_2H$, $R^3$ is H and the combination of $R^4$ and $R^5$ corresponds in each case to one row of Table A Table 28
Combination, in which $R^1$ is F, $R^2$ is $CF_2H$, $R^3$ is $CH_3$ and the combination of $R^4$ and $R^5$ corresponds in each case to one row of Table A Table 29
Combination, in which $R^1$ is F, $R^2$ is $CF_2H$, $R^3$ is $C_3H_5$ and the combination of $R^4$ and $R^5$ corresponds in each case to one row of Table A Table 30
Combination, in which $R^1$ is F, $R^2$ is $CF_2H$, $R^3$ is $C_6H_5$ and the combination of $R^4$ and $R^5$ corresponds in each case to one row of Table A Table 31
Combination, in which $R^1$ is F, $R^2$ is $CF_3$, $R^3$ is H and the combination of $R^4$ and $R^5$ corresponds in each case to one row of Table A Table 32
Combination, in which $R^1$ is F, $R^2$ is $CF_3$, $R^3$ is $CH_3$ and the combination of $R^4$ and $R^5$ corresponds in each case to one row of Table A Table 33
Combination, in which $R^1$ is F, $R^2$ is $CF_3$, $R^3$ is $C_3H_5$ and the combination of $R^4$ and $R^5$ corresponds in each case to one row of Table A Table 34
Combination, in which $R^1$ is F, $R^2$ is $CF_3$, $R^3$ is $C_6H_5$ and the combination of $R^4$ and $R^5$ corresponds in each case to one row of Table A Table 35
Combination, in which $R^1$ is $CH_3$, $R^2$ is $CH_3$, $R^3$ is H and the combination of $R^4$ and $R^5$ corresponds in each case to one row of Table A Table 36
Combination, in which $R^1$ is $CH_3$, $R^2$ is $CH_3$, $R^3$ is $C_3H_5$ and the combination of $R^4$ and $R^5$ corresponds in each case to one row of Table A Table 37
Combination, in which $R^1$ is $CH_3$, $R^2$ is $CH_3$, $R^3$ is $C_6H_5$ and the combination of $R^4$ and $R^5$ corresponds in each case to one row of Table A Table 38
Combination, in which $R^1$ is $CH_3$, $R^2$ is $C_3H_5$, $R^3$ is H and the combination of $R^4$ and $R^5$ corresponds in each case to one row of Table A Table 39
Combination, in which $R^1$ is $CH_3$, $R^2$ is $C_3H_5$, $R^3$ is $CH_3$ and the combination of $R^4$ and $R^5$ corresponds in each case to one row of Table A Table 40
Combination, in which $R^1$ is $CH_3$, $R^2$ is $C_3H_5$, $R^3$ is $C_6H_5$ and the combination of $R^4$ and $R^5$ corresponds in each case to one row of Table A Table 41
Combination, in which $R^1$ is $CH_3$, $R^2$ is $C_6H_5$, $R^3$ is H and the combination of $R^4$ and $R^5$ corresponds in each case to one row of Table A Table 42
Combination, in which $R^1$ is $CH_3$, $R^2$ is $C_6H_5$, $R^3$ is $CH_3$ and the combination of $R^4$ and $R^5$ corresponds in each case to one row of Table A Table 43
Combination, in which $R^1$ is $CH_3$, $R^2$ is $C_6H_5$, $R^3$ is $C_3H_5$ and the combination of $R^4$ and $R^5$ corresponds in each case to one row of Table A Table 44
Combination, in which $R^1$ is $CH_3$, $R^2$ is $CF_2H$, $R^3$ is H and the combination of $R^4$ and $R^5$ corresponds in each case to one row of Table A Table 45
Combination, in which $R^1$ is $CH_3$, $R^2$ is $CF_2H$, $R^3$ is $CH_3$ and the combination of $R^4$ and $R^5$ corresponds in each case to one row of Table A Table 46
Combination, in which $R^1$ is $CH_3$, $R^2$ is $CF_2H$, $R^3$ is $C_3H_5$ and the combination of $R^4$ and $R^5$ corresponds in each case to one row of Table A Table 47
Combination, in which $R^1$ is $CH_3$, $R^2$ is $CF_2H$, $R^3$ is $C_6H_5$ and the combination of $R^4$ and $R^5$ corresponds in each case to one row of Table A Table 48
Combination, in which $R^1$ is $CH_3$, $R^2$ is $CF_3$, $R^3$ is H and the combination of $R^4$ and $R^5$ corresponds in each case to one row of Table A Table 49
Combination, in which $R^1$ is $CH_3$, $R^2$ is $CF_3$, $R^3$ is $CH_3$ and the combination of $R^4$ and $R^5$ corresponds in each case to one row of Table A Table 50
Combination, in which $R^1$ is $CH_3$, $R^2$ is $CF_3$, $R^3$ is $C_3H_5$ and the combination of $R^4$ and $R^5$ corresponds in each case to one row of Table A Table 51
Combination, in which $R^1$ is $CH_3$, $R^2$ is $CF_3$, $R^3$ is $C_6H_5$ and the combination of $R^4$ and $R^5$ corresponds in each case to one row of Table A Table 52
Combination, in which $R^1$ is $C_6H_5$, $R^2$ is $CH_3$, $R^3$ is H and the combination of $R^4$ and $R^5$ corresponds in each case to one row of Table A Table 53
Combination, in which $R^1$ is $C_6H_5$, $R^2$ is $CH_3$, $R^3$ is $C_3H_5$ and the combination of $R^4$ and $R^5$ corresponds in each case to one row of Table A Table 54
Combination, in which $R^1$ is $C_6H_5$, $R^2$ is $CH_3$, $R^3$ is $C_6H_5$ and the combination of $R^4$ and $R^5$ corresponds in each case to one row of Table A Table 55
Combination, in which $R^1$ is $C_6H_5$, $R^2$ is $C_3H_5$, $R^3$ is H and the combination of $R^4$ and $R^5$ corresponds in each case to one row of Table A Table 56
Combination, in which $R^1$ is $C_6H_5$, $R^2$ is $C_3H_5$, $R^3$ is $CH_3$ and the combination of $R^4$ and $R^5$ corresponds in each case to one row of Table A Table 57
Combination, in which $R^1$ is $C_6H_5$, $R^2$ is $C_3H_5$, $R^3$ is $C_6H_5$ and the combination of $R^4$ and $R^5$ corresponds in each case to one row of Table A Table 58
Combination, in which $R^1$ is $C_6H_5$, $R^2$ is $C_6H_5$, $R^3$ is H and the combination of $R^4$ and $R^5$ corresponds in each case to one row of Table A Table 59
Combination, in which $R^1$ is $C_6H_5$, $R^2$ is $C_6H_5$, $R^3$ is $CH_3$ and the combination of $R^4$ and $R^5$ corresponds in each case to one row of Table A Table 60
Combination, in which $R^1$ is $C_6H_5$, $R^2$ is $C_6H_5$, $R^3$ is $C_3H_5$ and the combination of $R^4$ and $R^5$ corresponds in each case to one row of Table A Table 61
Combination, in which $R^1$ is $C_6H_5$, $R^2$ is $CF_2H$, $R^3$ is H and the combination of $R^4$ and $R^5$ corresponds in each case to one row of Table A Table 62
Combination, in which $R^1$ is $C_6H_5$, $R^2$ is $CF_2H$, $R^3$ is $CH_3$ and the combination of $R^4$ and $R^5$ corresponds in each case to one row of Table A Table 63
Combination, in which $R^1$ is $C_6H_5$, $R^2$ is $CF_2H$, $R^3$ is $C_3H_5$ and the combination of $R^4$ and $R^5$ corresponds in each case to one row of Table A Table 64
Combination, in which $R^1$ is $C_6H_5$, $R^2$ is $CF_2H$, $R^3$ is $C_6H_5$ and the combination of $R^4$ and $R^5$ corresponds in each case to one row of Table A Table 65
Combination, in which $R^1$ is $C_6H_5$, $R^2$ is $CF_3$, $R^3$ is H and the combination of $R^4$ and $R^5$ corresponds in each case to one row of Table A Table 66
Combination, in which $R^1$ is $C_6H_5$, $R^2$ is $CF_3$, $R^3$ is $CH_3$ and the combination of $R^4$ and $R^5$ corresponds in each case to one row of Table A Table 67
Combination, in which $R^1$ is $C_6H_5$, $R^2$ is $CF_3$, $R^3$ is $C_3H_5$ and the combination of $R^4$ and $R^5$ corresponds in each case to one row of Table A Table 68
Combination, in which $R^1$ is $C_6H_5$, $R^2$ is $CF_3$, $R^3$ is $C_6H_5$ and the combination of $R^4$ and $R^5$ corresponds in each case to one row of Table A Table 69
Combination, in which $R^1$ is $C(O)OCH_3$, $R^2$ is $CH_3$, $R^3$ is H and the combination of $R^4$ and $R^5$ corresponds in each case to one row of Table A Table 70
Combination, in which $R^1$ is $C(O)OCH_3$, $R^2$ is $CH_3$, $R^3$ is $C_3H_5$ and the combination of $R^4$ and $R^5$ corresponds in each case to one row of Table A Table 71
Combination, in which $R^1$ is $C(O)OCH_3$, $R^2$ is $CH_3$, $R^3$ is $C_6H_5$ and the combination of $R^4$ and $R^5$ corresponds in each case to one row of Table A Table 72
Combination, in which $R^1$ is $C(O)OCH_3$, $R^2$ is $C_3H_5$, $R^3$ is H and the combination of $R^4$ and $R^5$ corresponds in each case to one row of Table A Table 73
Combination, in which $R^1$ is $C(O)OCH_3$, $R^2$ is $C_3H_5$, $R^3$ is $CH_3$ and the combination of $R^4$ and $R^5$ corresponds in each case to one row of Table A Table 74
Combination, in which $R^1$ is $C(O)OCH_3$, $R^2$ is $C_3H_5$, $R^3$ is $C_6H_5$ and the combination of $R^4$ and $R^5$ corresponds in each case to one row of Table A Table 75
Combination, in which $R^1$ is $C(O)OCH_3$, $R^2$ is $C_6H_5$, $R^3$ is H and the combination of $R^4$ and $R^5$ corresponds in each case to one row of Table A Table 76
Combination, in which $R^1$ is $C(O)OCH_3$, $R^2$ is $C_6H_5$, $R^3$ is $CH_3$ and the combination of $R^4$ and $R^5$ corresponds in each case to one row of Table A Table 77
Combination, in which $R^1$ is $C(O)OCH_3$, $R^2$ is $C_6H_5$, $R^3$ is $C_3H_5$ and the combination of $R^4$ and $R^5$ corresponds in each case to one row of Table A Table 78
Combination, in which $R^1$ is $C(O)OCH_3$, $R^2$ is $CF_2H$, $R^3$ is H and the combination of $R^4$ and $R^5$ corresponds in each case to one row of Table A Table 79
Combination, in which $R^1$ is $C(O)OCH_3$, $R^2$ is $CF_2H$, $R^3$ is $CH_3$ and the combination of $R^4$ and $R^5$ corresponds in each case to one row of Table A Table 80
Combination, in which $R^1$ is $C(O)OCH_3$, $R^2$ is $CF_2H$, $R^3$ is $C_3H_5$ and the combination of $R^4$ and $R^5$ corresponds in each case to one row of Table A Table 81
Combination, in which $R^1$ is $C(O)OCH_3$, $R^2$ is $CF_2H$, $R^3$ is $C_6H_5$ and the combination of $R^4$ and $R^5$ corresponds in each case to one row of Table A Table 82
Combination, in which $R^1$ is $C(O)OCH_3$, $R^2$ is $CF_3$, $R^3$ is H and the combination of $R^4$ and $R^5$ corresponds in each case to one row of Table A Table 83
Combination, in which $R^1$ is $C(O)OCH_3$, $R^2$ is $CF_3$, $R^3$ is $CH_3$ and the combination of $R^4$ and $R^5$ corresponds in each case to one row of Table A Table 84
Combination, in which $R^1$ is $C(O)OCH_3$, $R^2$ is $CF_3$, $R^3$ is $C_3H_5$ and the combination of $R^4$ and $R^5$ corresponds in each case to one row of Table A Table 85
Combination, in which $R^1$ is $C(O)OCH_3$, $R^2$ is $CF_3$, $R^3$ is $C_6H_5$ and the combination of $R^4$ and $R^5$ corresponds in each case to one row of Table A Table 86
Combination, in which $R^1$ is $C(O)OCH_2CH_3$, $R^2$ is $CH_3$, $R^3$ is H and the combination of $R^4$ and $R^5$ corresponds in each case to one row of Table A Table 87
Combination, in which $R^1$ is $C(O)OCH_2CH_3$, $R^2$ is $CH_3$, $R^3$ is $C_3H_5$ and the combination of $R^4$ and $R^5$ corresponds in each case to one row of Table A Table 88
Combination, in which $R^1$ is $C(O)OCH_2CH_3$, $R^2$ is $CH_3$, $R^3$ is $C_6H_5$ and the combination of $R^4$ and $R^5$ corresponds in each case to one row of Table A Table 89
Combination, in which $R^1$ is $C(O)OCH_2CH_3$, $R^2$ is $C_3H_5$, $R^3$ is H and the combination of $R^4$ and $R^5$ corresponds in each case to one row of Table A Table 90
Combination, in which $R^1$ is $C(O)OCH_2CH_3$, $R^2$ is $C_3H_5$, $R^3$ is $CH_3$ and the combination of $R^4$ and $R^5$ corresponds in each case to one row of Table A Table 91
Combination, in which $R^1$ is $C(O)OCH_2CH_3$, $R^2$ is $C_3H_5$, $R^3$ is $C_6H_5$ and the combination of $R^4$ and $R^5$ corresponds in each case to one row of Table A Table 92
Combination, in which $R^1$ is $C(O)OCH_2CH_3$, $R^2$ is $C_6H_5$, $R^3$ is H and the combination of $R^4$ and $R^5$ corresponds in each case to one row of Table A Table 93
Combination, in which $R^1$ is $C(O)OCH_2CH_3$, $R^2$ is $C_6H_5$, $R^3$ is $CH_3$ and the combination of $R^4$ and $R^5$ corresponds in each case to one row of Table A Table 94
Combination, in which $R^1$ is $C(O)OCH_2CH_3$, $R^2$ is $C_6H_5$, $R^3$ is $C_3H_5$ and the combination of $R^4$ and $R^5$ corresponds in each case to one row of Table A Table 95
Combination, in which $R^1$ is $C(O)OCH_2CH_3$, $R^2$ is $CF_2H$, $R^3$ is H and the combination of $R^4$ and $R^5$ corresponds in each case to one row of Table A Table 96
Combination, in which $R^1$ is $C(O)OCH_2CH_3$, $R^2$ is $CF_2H$, $R^3$ is $CH_3$ and the combination of $R^4$ and $R^5$ corresponds in each case to one row of Table A Table 97
Combination, in which $R^1$ is $C(O)OCH_2CH_3$, $R^2$ is $CF_2H$, $R^3$ is $C_3H_5$ and the combination of $R^4$ and $R^5$ corresponds in each case to one row of Table A Table 98
Combination, in which $R^1$ is $C(O)OCH_2CH_3$, $R^2$ is $CF_2H$, $R^3$ is $C_6H_5$ and the combination of $R^4$ and $R^5$ corresponds in each case to one row of Table A Table 99
Combination, in which $R^1$ is $C(O)OCH_2CH_3$, $R^2$ is $CF_3$, $R^3$ is H and the combination of $R^4$ and $R^5$ corresponds in each case to one row of Table A Table 100
Combination, in which $R^1$ is $C(O)OCH_2CH_3$, $R^2$ is $CF_3$, $R^3$ is $CH_3$ and the combination of $R^4$ and $R^5$ corresponds in each case to one row of Table A Table 101
Combination, in which $R^1$ is $C(O)OCH_2CH_3$, $R^2$ is $CF_3$, $R^3$ is $C_3H_5$ and the combination of $R^4$ and $R^5$ corresponds in each case to one row of Table A Table 102
Combination, in which $R^1$ is $C(O)OCH_2CH_3$, $R^2$ is $CF_3$, $R^3$ is $C_6H_5$ and the combination of $R^4$ and $R^5$ corresponds in each case to one row of Table A Table 103
Combination, in which $R^1$ is $C(O)OC(CH_3)_3$, $R^2$ is $CH_3$, $R^3$ is H and the combination of $R^4$ and $R^5$ corresponds in each case to one row of Table A Table 104
Combination, in which $R^1$ is $C(O)OC(CH_3)_3$, $R^2$ is $CH_3$, $R^3$ is $C_3H_5$ and the combination of $R^4$ and $R^5$ corresponds in each case to one row of Table A Table 105
Combination, in which $R^1$ is $C(O)OC(CH_3)_3$, $R^2$ is $CH_3$, $R^3$ is $C_6H_5$ and the combination of $R^4$ and $R^5$ corresponds in each case to one row of Table A Table 106
Combination, in which $R^1$ is $C(O)OC(CH_3)_3$, $R^2$ is $C_3H_5$, $R^3$ is H and the combination of $R^4$ and $R^5$ corresponds in each case to one row of Table A Table 107
Combination, in which $R^1$ is $C(O)OC(CH_3)_3$, $R^2$ is $C_3H_5$, $R^3$ is $CH_3$ and the combination of $R^4$ and $R^5$ corresponds in each case to one row of Table A Table 108
Combination, in which $R^1$ is $C(O)OC(CH_3)_3$, $R^2$ is $C_3H_5$, $R^3$ is $C_6H_5$ and the combination of $R^4$ and $R^5$ corresponds in each case to one row of Table A Table 109
Combination, in which $R^1$ is $C(O)OC(CH_3)_3$, $R^2$ is $C_6H_5$, $R^3$ is H and the combination of $R^4$ and $R^5$ corresponds in each case to one row of Table A Table 110
Combination, in which $R^1$ is $C(O)OC(CH_3)_3$, $R^2$ is $C_6H_5$, $R^3$ is $CH_3$ and the combination of $R^4$ and $R^5$ corresponds in each case to one row of Table A Table 111
Combination, in which $R^1$ is $C(O)OC(CH_3)_3$, $R^2$ is $C_6H_5$, $R^3$ is $C_3H_5$ and the combination of $R^4$ and $R^5$ corresponds in each case to one row of Table A Table 112
Combination, in which $R^1$ is $C(O)OC(CH_3)_3$, $R^2$ is $CF_2H$, $R^3$ is H and the combination of $R^4$ and $R^5$ corresponds in each case to one row of Table A Table 113
Combination, in which $R^1$ is $C(O)OC(CH_3)_3$, $R^2$ is $CF_2H$, $R^3$ is $CH_3$ and the combination of $R^4$ and $R^5$ corresponds in each case to one row of Table A Table 114
Combination, in which $R^1$ is $C(O)OC(CH_3)_3$, $R^2$ is $CF_2H$, $R^3$ is $C_3H_5$ and the combination of $R^4$ and $R^5$ corresponds in each case to one row of Table A Table 115
Combination, in which $R^1$ is $C(O)OC(CH_3)_3$, $R^2$ is $CF_2H$, $R^3$ is $C_6H_5$ and the combination of $R^4$ and $R^5$ corresponds in each case to one row of Table A Table 116
Combination, in which $R^1$ is $C(O)OC(CH_3)_3$, $R^2$ is $CF_3$, $R^3$ is H and the combination of $R^4$ and $R^5$ corresponds in each case to one row of Table A Table 117
Combination, in which $R^1$ is $C(O)OC(CH_3)_3$, $R^2$ is $CF_3$, $R^3$ is $CH_3$ and the combination of $R^4$ and $R^5$ corresponds in each case to one row of Table A Table 118
Combination, in which $R^1$ is $C(O)OC(CH_3)_3$, $R^2$ is $CF_3$, $R^3$ is $C_3H_5$ and the combination of $R^4$ and $R^5$ corresponds in each case to one row of Table A Table 119
Combination, in which $R^1$ is $C(O)OC(CH_3)_3$, $R^2$ is $CF_3$, $R^3$ is $C_6H_5$ and the combination of $R^4$ and $R^5$ corresponds in each case to one row of Table A Table 120
Combination, in which $R^1$ is $C(O)OCH_2C_6H_5$, $R^2$ is $CH_3$, $R^3$ is H and the combination of $R^4$ and $R^5$ corresponds in each case to one row of Table A Table 121
Combination, in which $R^1$ is $C(O)OCH_2C_6H_5$, $R^2$ is $CH_3$, $R^3$ is $C_3H_5$ and the combination of $R^4$ and $R^5$ corresponds in each case to one row of Table A Table 122
Combination, in which $R^1$ is $C(O)OCH_2C_6H_5$, $R^2$ is $CH_3$, $R^3$ is $C_6H_5$ and the combination of $R^4$ and $R^5$ corresponds in each case to one row of Table A Table 123
Combination, in which $R^1$ is $C(O)OCH_2C_6H_5$, $R^2$ is $C_3H_5$, $R^3$ is H and the combination of $R^4$ and $R^5$ corresponds in each case to one row of Table A Table 124
Combination, in which $R^1$ is $C(O)OCH_2C_6H_5$, $R^2$ is $C_3H_5$, $R^3$ is $CH_3$ and the combination of $R^4$ and $R^5$ corresponds in each case to one row of Table A Table 125
Combination, in which $R^1$ is $C(O)OCH_2C_6H_5$, $R^2$ is $C_3H_5$, $R^3$ is $C_6H_5$ and the combination of $R^4$ and $R^5$ corresponds in each case to one row of Table A Table 126
Combination, in which $R^1$ is $C(O)OCH_2C_6H_5$, $R^2$ is $C_6H_5$, $R^3$ is H and the combination of $R^4$ and $R^5$ corresponds in each case to one row of Table A Table 127
Combination, in which $R^1$ is $C(O)OCH_2C_6H_5$, $R^2$ is $C_6H_5$, $R^3$ is $CH_3$ and the combination of $R^4$ and $R^5$ corresponds in each case to one row of Table A Table 128
Combination, in which $R^1$ is $C(O)OCH_2C_6H_5$, $R^2$ is $C_6H_5$, $R^3$ is $C_3H_5$ and the combination of $R^4$ and $R^5$ corresponds in each case to one row of Table A Table 129
Combination, in which $R^1$ is $C(O)OCH_2C_6H_5$, $R^2$ is $CF_2H$, $R^3$ is H and the combination of $R^4$ and $R^5$ corresponds in each case to one row of Table A Table 130
Combination, in which $R^1$ is $C(O)OCH_2C_6H_5$, $R^2$ is $CF_2H$, $R^3$ is $CH_3$ and the combination of $R^4$ and $R^5$ corresponds in each case to one row of Table A Table 131
Combination, in which $R^1$ is $C(O)OCH_2C_6H_5$, $R^2$ is $CF_2H$, $R^3$ is $C_3H_5$ and the combination of $R^4$ and $R^5$ corresponds in each case to one row of Table A Table 132
Combination, in which $R^1$ is $C(O)OCH_2C_6H_5$, $R^2$ is $CF_2H$, $R^3$ is $C_6H_5$ and the combination of $R^4$ and $R^5$ corresponds in each case to one row of Table A Table 133
Combination, in which $R^1$ is $C(O)OCH_2C_6H_5$, $R^2$ is $CF_3$, $R^3$ is H and the combination of $R^4$ and $R^5$ corresponds in each case to one row of Table A Table 134
Combination, in which $R^1$ is $C(O)OCH_2C_6H_5$, $R^2$ is $CF_3$, $R^3$ is $CH_3$ and the combination of $R^4$ and $R^5$ corresponds in each case to one row of Table A Table 135
Combination, in which $R^1$ is $C(O)OCH_2C_6H_5$, $R^2$ is $CF_3$, $R^3$ is $C_3H_5$ and the combination of $R^4$ and $R^5$ corresponds in each case to one row of Table A Table 136
Combination, in which $R^1$ is $C(O)OCH_2C_6H_5$, $R^2$ is $CF_3$, $R^3$ is $C_6H_5$ and the combination of $R^4$ and $R^5$ corresponds in each case to one row of Table A Table 137
Combination, in which $R^1$ is CN, $R^2$ is $CH_3$, $R^3$ is H and the combination of $R^4$ and $R^5$ corresponds in each case to one row of Table A Table 138
Combination, in which $R^1$ is CN, $R^2$ is $CH_3$, $R^3$ is $C_3H_5$ and the combination of $R^4$ and $R^5$ corresponds in each case to one row of Table A Table 139
Combination, in which $R^1$ is CN, $R^2$ is $CH_3$, $R^3$ is $C_6H_5$ and the combination of $R^4$ and $R^5$ corresponds in each case to one row of Table A Table 140
Combination, in which $R^1$ is CN, $R^2$ is $C_3H_5$, $R^3$ is H and the combination of $R^4$ and $R^5$ corresponds in each case to one row of Table A Table 141
Combination, in which $R^1$ is CN, $R^2$ is $C_3H_5$, $R^3$ is $CH_3$ and the combination of $R^4$ and $R^5$ corresponds in each case to one row of Table A Table 142
Combination, in which $R^1$ is CN, $R^2$ is $C_3H_5$, $R^3$ is $C_6H_5$ and the combination of $R^4$ and $R^5$ corresponds in each case to one row of Table A Table 143
Combination, in which $R^1$ is CN, $R^2$ is $C_6H_5$, $R^3$ is H and the combination of $R^4$ and $R^5$ corresponds in each case to one row of Table A Table 144
Combination, in which $R^1$ is CN, $R^2$ is $C_6H_5$, $R^3$ is $CH_3$ and the combination of $R^4$ and $R^5$ corresponds in each case to one row of Table A Table 145
Combination, in which $R^1$ is CN, $R^2$ is $C_6H_5$, $R^3$ is $C_3H_5$ and the combination of $R^4$ and $R^5$ corresponds in each case to one row of Table A Table 146
Combination, in which $R^1$ is CN, $R^2$ is $CF_2H$, $R^3$ is H and the combination of $R^4$ and $R^5$ corresponds in each case to one row of Table A Table 147
Combination, in which $R^1$ is CN, $R^2$ is $CF_2H$, $R^3$ is $CH_3$ and the combination of $R^4$ and $R^5$ corresponds in each case to one row of Table A Table 148
Combination, in which $R^1$ is CN, $R^2$ is $CF_2H$, $R^3$ is $C_3H_5$ and the combination of $R^4$ and $R^5$ corresponds in each case to one row of Table A Table 149
Combination, in which $R^1$ is CN, $R^2$ is $CF_2H$, $R^3$ is $C_6H_5$ and the combination of $R^4$ and $R^5$ corresponds in each case to one row of Table A Table 150
Combination, in which $R^1$ is CN, $R^2$ is $CF_3$, $R^3$ is H and the combination of $R^4$ and $R^5$ corresponds in each case to one row of Table A Table 151
Combination, in which $R^1$ is CN, $R^2$ is $CF_3$, $R^3$ is $CH_3$ and the combination of $R^4$ and $R^5$ corresponds in each case to one row of Table A Table 152
Combination, in which $R^1$ is CN, $R^2$ is $CF_3$, $R^3$ is $C_3H_5$ and the combination of $R^4$ and $R^5$ corresponds in each case to one row of Table A Table 153
Combination, in which $R^1$ is CN, $R^2$ is $CF_3$, $R^3$ is $C_6H_5$ and the combination of $R^4$ and $R^5$ corresponds in each case to one row of Table A

TABLE A

| No. | $R^4$ | $R^5$ |
|---|---|---|
| A-1 | H | H |
| A-2 | $CH_3$ | H |
| A-3 | $CH(CH_3)_2$ | H |
| A-4 | $cC_3H_5$ | H |
| A-5 | $C_6H_5$ | H |
| A-6 | $CH_2C_6H_5$ | H |
| A-7 | $CHFCH_3$ | H |
| A-8 | 1-$C(O)NH_2$-$cC_3H_4$ | H |
| A-9 | 1-CN—$C_3H_4$ | H |
| A-10 | $CH_3$ | $CH_3$ |
| A-11 | $CH(CH_3)_2$ | $CH_3$ |
| A-12 | $cC_3H_5$ | $CH_3$ |
| A-13 | $C_6H_5$ | $CH_3$ |
| A-14 | $CH_2C_6H_5$ | $CH_3$ |
| A-15 | $CHFCH_3$ | $CH_3$ |
| A-16 | 1-$C(O)NH_2$-$cC_3H_4$ | $CH_3$ |
| A-17 | 1-CN—$C_3H_4$ | $CH_3$ |
| A-18 | $CH(CH_3)_2$ | $CH(CH_3)_2$ |
| A-19 | $cC_3H_5$ | $CH(CH_3)_2$ |
| A-20 | $C_6H_5$ | $CH(CH_3)_2$ |
| A-21 | $CH_2C_6H_5$ | $CH(CH_3)_2$ |
| A-22 | $CHFCH_3$ | $CH(CH_3)_2$ |
| A-23 | 1-$C(O)NH_2$-$cC_3H_4$ | $CH(CH_3)_2$ |
| A-24 | 1-CN—$C_3H_4$ | $CH(CH_3)_2$ |
| A-25 | $cC_3H_5$ | $cC_3H_5$ |
| A-26 | $C_6H_5$ | $cC_3H_5$ |
| A-27 | $CH_2C_6H_5$ | $cC_3H_5$ |
| A-28 | $CHFCH_3$ | $cC_3H_5$ |
| A-29 | 1-$C(O)NH_2$-$cC_3H_4$ | $cC_3H_5$ |
| A-30 | 1-CN—$C_3H_4$ | $cC_3H_5$ |
| A-31 | $C_6H_5$ | $C_6H_5$ |
| A-32 | $CH_2C_6H_5$ | $C_6H_5$ |
| A-33 | $CHFCH_3$ | $C_6H_5$ |
| A-34 | 1-$C(O)NH_2$-$cC_3H_4$ | $C_6H_5$ |
| A-35 | 1-CN—$C_3H_4$ | $C_6H_5$ |
| A-36 | $CH_2C_6H_5$ | $CH_2C_6H_5$ |
| A-37 | $CHFCH_3$ | $CH_2C_6H_5$ |
| A-38 | 1-$C(O)NH_2$-$cC_3H_4$ | $CH_2C_6H_5$ |
| A-39 | 1-CN—$C_3H_4$ | $CH_2C_6H_5$ |
| A-40 | $CHFCH_3$ | $CHFCH_3$ |
| A-41 | 1-$C(O)NH_2$-$cC_3H_4$ | $CHFCH_3$ |
| A-42 | 1-CN—$C_3H_4$ | $CHFCH_3$ |
| A-43 | 1-$C(O)NH_2$-$cC_3H_4$ | 1-$C(O)NH_2$-$cC_3H_4$ |
| A-44 | 1-CN—$C_3H_4$ | 1-$C(O)NH_2$-$cC_3H_4$ |
| A-45 | 1-CN—$C_3H_4$ | 1-CN-$C_3H_4$ |
| A-46 | H | $CH_2OH$ |
| A-47 | $CH_3$ | $CH_2OH$ |

TABLE A-continued

| No. | $R^4$ | $R^5$ |
|---|---|---|
| A-48 | $CH(CH_3)_2$ | $CH_2OH$ |
| A-49 | $cC_3H_5$ | $CH_2OH$ |
| A-50 | $C_6H_5$ | $CH_2OH$ |
| A-51 | $CH_2C_6H_5$ | $CH_2OH$ |
| A-52 | $CHFCH_3$ | $CH_2OH$ |
| A-53 | $1\text{-}C(O)NH_2\text{-}cC_3H_4$ | $CH_2OH$ |
| A-54 | $1\text{-}CN\text{—}C_3H_4$ | $CH_2OH$ |
| A-55 | H | $CH(CH_3)OH$ |
| A-56 | $CH_3$ | $CH(CH_3)OH$ |
| A-57 | $CH(CH_3)_2$ | $CH(CH_3)OH$ |
| A-58 | $cC_3H_5$ | $CH(CH_3)OH$ |
| A-59 | $C_6H_5$ | $CH(CH_3)OH$ |
| A-60 | $CH_2C_6H_5$ | $CH(CH_3)OH$ |
| A-61 | $CHFCH_3$ | $CH(CH_3)OH$ |
| A-62 | $1\text{-}C(O)NH_2\text{-}cC_3H_4$ | $CH(CH_3)OH$ |
| A-63 | $1\text{-}CN\text{—}C_3H_4$ | $CH(CH_3)OH$ |
| A-64 | H | $C(CH_3)_2OH$ |
| A-65 | $CH_3$ | $C(CH_3)_2OH$ |
| A-66 | $CH(CH_3)_2$ | $C(CH_3)_2OH$ |
| A-67 | $cC_3H_5$ | $C(CH_3)_2OH$ |
| A-68 | $C_6H_5$ | $C(CH_3)_2OH$ |
| A-69 | $CH_2C_6H_5$ | $C(CH_3)_2OH$ |
| A-70 | $CHFCH_3$ | $C(CH_3)_2OH$ |
| A-71 | $1\text{-}C(O)NH_2\text{-}cC_3H_4$ | $C(CH_3)_2OH$ |
| A-72 | $1\text{-}CN\text{—}C_3H_4$ | $C(CH_3)_2OH$ |
| A-73 | H | $CH_2CH_2OH$ |
| A-74 | $CH_3$ | $CH_2CH_2OH$ |
| A-75 | $CH(CH_3)_2$ | $CH_2CH_2OH$ |
| A-76 | $cC_3H_5$ | $CH_2CH_2OH$ |
| A-77 | $C_6H_5$ | $CH_2CH_2OH$ |
| A-78 | $CH_2C_6H_5$ | $CH_2CH_2OH$ |
| A-79 | $CHFCH_3$ | $CH_2CH_2OH$ |
| A-80 | $1\text{-}C(O)NH_2\text{-}cC_3H_4$ | $CH_2CH_2OH$ |
| A-81 | $1\text{-}CN\text{—}C_3H_4$ | $CH_2CH_2OH$ |
| A-82 | H | $CH(CH_3)CH_2OH$ |
| A-83 | $CH_3$ | $CH(CH_3)CH_2OH$ |
| A-84 | $CH(CH_3)_2$ | $CH(CH_3)CH_2OH$ |
| A-85 | $cC_3H_5$ | $CH(CH_3)CH_2OH$ |
| A-86 | $C_6H_5$ | $CH(CH_3)CH_2OH$ |
| A-87 | $CH_2C_6H_5$ | $CH(CH_3)CH_2OH$ |
| A-88 | $CHFCH_3$ | $CH(CH_3)CH_2OH$ |
| A-89 | $1\text{-}C(O)NH_2\text{-}cC_3H_4$ | $CH(CH_3)CH_2OH$ |
| A-90 | $1\text{-}CN\text{—}C_3H_4$ | $CH(CH_3)CH_2OH$ |
| A-91 | H | 2-furyl |
| A-92 | $CH_3$ | 2-furyl |
| A-93 | $CH(CH_3)_2$ | 2-furyl |
| A-94 | $cC_3H_5$ | 2-furyl |
| A-95 | $C_6H_5$ | 2-furyl |
| A-96 | $CH_2C_6H_5$ | 2-furyl |
| A-97 | $CHFCH_3$ | 2-furyl |
| A-98 | $1\text{-}C(O)NH_2\text{-}cC_3H_4$ | 2-furyl |
| A-99 | $1\text{-}CN\text{—}C_3H_4$ | 2-furyl |
| A-100 | H | 3-furyl |
| A-101 | $CH_3$ | 3-furyl |
| A-102 | $CH(CH_3)_2$ | 3-furyl |
| A-103 | $cC_3H_5$ | 3-furyl |
| A-104 | $C_6H_5$ | 3-furyl |
| A-105 | $CH_2C_6H_5$ | 3-furyl |
| A-106 | $CHFCH_3$ | 3-furyl |
| A-107 | $1\text{-}C(O)NH_2\text{-}cC_3H_4$ | 3-furyl |
| A-108 | $1\text{-}CN\text{—}C_3H_4$ | 3-furyl |
| A-109 | H | $CH(OCH_3)_2$ |
| A-110 | $CH_3$ | $CH(OCH_3)_2$ |
| A-111 | $CH(CH_3)_2$ | $CH(OCH_3)_2$ |
| A-112 | $cC_3H_5$ | $CH(OCH_3)_2$ |
| A-113 | $C_6H_5$ | $CH(OCH_3)_2$ |
| A-114 | $CH_2C_6H_5$ | $CH(OCH_3)_2$ |
| A-115 | $CHFCH_3$ | $CH(OCH_3)_2$ |
| A-116 | $1\text{-}C(O)NH_2\text{-}cC_3H_4$ | $CH(OCH_3)_2$ |
| A-117 | $1\text{-}CN\text{—}C_3H_4$ | $CH(OCH_3)_2$ |
| A-118 | H | $CH_2cC_6H_{11}$ |
| A-119 | $CH_3$ | $CH_2cC_6H_{11}$ |
| A-120 | $CH(CH_3)_2$ | $CH_2cC_6H_{11}$ |
| A-121 | $cC_3H_5$ | $CH_2cC_6H_{11}$ |
| A-122 | $C_6H_5$ | $CH_2cC_6H_{11}$ |
| A-123 | $CH_2C_6H_5$ | $CH_2cC_6H_{11}$ |
| A-124 | $CHFCH_3$ | $CH_2cC_6H_{11}$ |
| A-125 | $1\text{-}C(O)NH_2\text{-}cC_3H_4$ | $CH_2cC_6H_{11}$ |
| A-126 | $1\text{-}CN\text{—}C_3H_4$ | $CH_2cC_6H_{11}$ |
| A-127 | H | $CH_2C(CH_3)_3$ |
| A-128 | $CH_3$ | $CH_2C(CH_3)_3$ |
| A-129 | $CH(CH_3)_2$ | $CH_2C(CH_3)_3$ |
| A-130 | $cC_3H_5$ | $CH_2C(CH_3)_3$ |
| A-131 | $C_6H_5$ | $CH_2C(CH_3)_3$ |
| A-132 | $CH_2C_6H_5$ | $CH_2C(CH_3)_3$ |
| A-133 | $CHFCH_3$ | $CH_2C(CH_3)_3$ |
| A-134 | $1\text{-}C(O)NH_2\text{-}cC_3H_4$ | $CH_2C(CH_3)_3$ |
| A-135 | $1\text{-}CN\text{—}C_3H_4$ | $CH_2C(CH_3)_3$ |
| A-136 | H | $CH(CH_2CH_3)_2$ |
| A-137 | $CH_3$ | $CH(CH_2CH_3)_2$ |
| A-138 | $CH(CH_3)_2$ | $CH(CH_2CH_3)_2$ |
| A-139 | $cC_3H_5$ | $CH(CH_2CH_3)_2$ |
| A-140 | $C_6H_5$ | $CH(CH_2CH_3)_2$ |
| A-141 | $CH_2C_6H_5$ | $CH(CH_2CH_3)_2$ |
| A-142 | $CHFCH_3$ | $CH(CH_2CH_3)_2$ |
| A-143 | $1\text{-}C(O)NH_2\text{-}cC_3H_4$ | $CH(CH_2CH_3)_2$ |
| A-144 | $1\text{-}CN\text{—}C_3H_4$ | $CH(CH_2CH_3)_2$ |
| A-145 | H | $C(CH_3)_2SCH_3$ |
| A-146 | $CH_3$ | $C(CH_3)_2SCH_3$ |
| A-147 | $CH(CH_3)_2$ | $C(CH_3)_2SCH_3$ |
| A-148 | $cC_3H_5$ | $C(CH_3)_2SCH_3$ |
| A-149 | $C_6H_5$ | $C(CH_3)_2SCH_3$ |
| A-150 | $CH_2C_6H_5$ | $C(CH_3)_2SCH_3$ |
| A-151 | $CHFCH_3$ | $C(CH_3)_2SCH_3$ |
| A-152 | $1\text{-}C(O)NH_2\text{-}cC_3H_4$ | $C(CH_3)_2SCH_3$ |
| A-153 | $1\text{-}CN\text{—}C_3H_4$ | $C(CH_3)_2SCH_3$ |
| A-154 | \multicolumn{2}{c}{$CH_2CH_2CF_2CH_2CH_2$} |
| A-155 | \multicolumn{2}{c}{$CH_2CH_2CH_2$} |
| A-156 | \multicolumn{2}{c}{$CH_2CH_2CH_2CH_2$} |
| A-157 | \multicolumn{2}{c}{$CH_2CH_2CH_2CH_2CH_2$} |
| A-158 | \multicolumn{2}{c}{$CH_2OC(CH_3)_2OCH_2$} |
| A-159 | \multicolumn{2}{c}{$CH_2OCH_2OCH_2$} |

In a preferred embodiment of the invention, the compounds of formula V are compounds, wherein $R^1$, $R^2$, $R^3$, $R^4$, and $R^5$ are according to any one of Tables 1 to 153 in combination with table A, entries A-1 to A-159, and wherein $R^6$ is H.

In another preferred embodiment of the invention, the compounds of formula V are compounds, wherein $R^1$, $R^2$, $R^3$, $R^4$, and $R^5$ are according to any one of Tables 1 to 153 in combination with table A, entries A-1 to A-159, and wherein $R^6$ is CN.

In yet another preferred embodiment of the invention, the compounds of formula V are compounds, wherein $R^1$, $R^2$, $R^3$, $R^4$, and $R^5$ are according to any one of Tables 1 to 153 in combination with table A, entries A-1 to A-159, and wherein $R^6$ is $CHF_2$.

In yet another preferred embodiment of the invention, the compounds of formula V are compounds, wherein $R^1$, $R^2$, $R^3$, $R^4$, and $R^5$ are according to any one of Tables 1 to 153 in combination with table A, entries A-1 to A-159, and wherein $R^6$ is $CF_3$.

Particularly preferred are compounds of formula V, wherein $R^1$, $R^2$, $R^3$, $R^4$, and $R^5$ are according to any one of Tables 1 to 153 in combination with table A, entries A-1 to A-159, and wherein $R^6$ is H.

If the meanings of $R^4$ and $R^5$ are different from each other and different from $R^6$, it is again noted that the compounds of formula V, for which the above combinations of substituents $R^1$, $R^2$, $R^3$, $R^4$ and $R^5$ as well as $R^6$ are preferred, may be present in the form of different stereoisomers because the —$CR^4R^5R^6$ group is then chiral.

The same combinations of substituents $R^1$, $R^2$, $R^3$, $R^4$ and $R^5$ as defined in the above tables 1 to 153 in combination with table A, entries A-1 to A-159, are also preferred for the compounds of formula IV.

Thus, in a preferred embodiment of the invention, the compounds of formula IV are compounds, wherein $R^1$, $R^2$, $R^3$, $R^4$, and $R^5$ are according to any one of Tables 1 to 153 in combination with table A, entries A-1 to A-159.

It is again noted that the wavy lines in generic formula IV indicate that the substituents $R^4$ and $R^5$ as well as the substituents $R^3$ and the hydrazone moiety may be present in both possible positions, so that all possible E- and Z-isomers can be realized.

The same combinations of substituents $R^1$, $R^2$, $R^3$, $R^4$ and $R^5$ as defined in the above tables 1 to 153 in combination with table A, entries A-1 to A-159, are also preferred for the precursors of the compounds of formula IV, i.e. the compounds of formula I, II and III, provided that the substituents are present.

Thus, in one preferred embodiment of the invention, the compounds of formula III are compounds, wherein $R^1$, $R^2$ and $R^3$ are as defined in Tables 1 to 153.

Furthermore, in one preferred embodiment of the invention, the compounds of formula II are compounds, wherein $R^4$ and $R^5$ are as defined in Tables A-1 to A-159.

Furthermore, in one preferred embodiment of the invention, the compounds of formula I are compounds, wherein $R^4$ and $R^5$ are as defined in Tables A-1 to A-159.

As already indicated above, the compounds of formula IV are obtainable from the compounds of formula III by reacting them with compounds of formula II.

Apart from the substituents discussed above, the compounds of formula III further comprise a substituent X, which represents a leaving group. In principal, any leaving group, which is known in the art, e.g. in the context of nucleophilic substitution reactions, is suitable as substituent X. In the process of preparing the compounds of formula IV as described herein, the substituent X of the compounds of formula III is substituted by the amino group of hydrazine, so that the substituent is no longer contained in the compounds of formula IV.

In a preferred embodiment of the invention, in the compounds of formula III X is halogen, OH, $C_1$-$C_{10}$-alkoxy, $C_3$-$C_{10}$-cycloalkoxy, $C_1$-$C_{10}$-alkyl-C(O)O—, $C_1$-$C_{10}$-alkyl-S(O)$_2$O—, $C_1$-$C_{10}$-haloalkyl-S(O)$_2$O—, phenyl-S(O)$_2$O—, tolyl-S(O)$_2$O—, $(C_1$-$C_{10}$-alkyloxy)$_2$P(O)O—, $C_1$-$C_{10}$-alkylthio, $C_3$-$C_{10}$-cycloalkylthio, $C_1$-$C_{10}$-alkyl-C(O)S—, $NH_2$, $C_1$-$C_{10}$-alkylamino, $C_1$-$C_{10}$-dialkylamino, morpholino, N-methylpiperazino or aza-$C_3$-$C_{10}$-cycloalkyl;

In a more preferred embodiment of the invention, in the compounds of formula III X is halogen, $C_1$-$C_4$-alkoxy, $C_1$-$C_4$-dialkylamino, morpholino, N-methylpiperazino or aza-$C_5$-$C_6$-cycloalkyl.

Preferably, X is halogen. As halogen, chlorine is particularly preferred.

With regard to the $C_1$-$C_4$-dialkylamino groups, it is noted that the alkyl chains may have identical or different chain lengths. Dimethylamino and diethylamino groups are particularly preferred according to the present invention.

Furthermore, $C_1$-$C_4$-alkoxy groups, in particular $C_1$-$C_2$-alkoxy groups, are particularly preferred according to the present invention.

The substituents $R^1$, $R^2$ and $R^3$ of the compounds of formula III were already discussed above.

Preferred compounds of formula III according to the present invention are compounds, wherein $R^1$, $R^2$ and $R^3$ are as defined above in any one of tables 1 to 153, and X is any one of Cl, $OCH_3$, $OCH_2CH_3$, $N(CH_3)_2$, $N(CH_2CH_3)_2$. It is to be understood that each combination between the substituents $R^1$, $R^2$ and $R^3$ according to tables 1 to 153 and X being Cl, $OCH_3$, $OCH_2CH_3$, $N(CH_3)_2$, $N(CH_2CH_3)_2$ is suitable for the compounds of formula III according to the present invention.

Thus, in a preferred embodiment of the invention, the compounds of formula III are compounds, wherein $R^1$, $R^2$ and $R^3$ are as defined in Tables 1 to 153, and wherein X is Cl.

In another preferred embodiment of the invention, the compounds of formula III are compounds, wherein $R^1$, $R^2$ and $R^3$ are as defined in Tables 1 to 153, and wherein X is $OCH_3$.

In yet another preferred embodiment of the invention, the compounds of formula III are compounds, wherein $R^1$, $R^2$ and $R^3$ are as defined in Tables 1 to 153, and wherein X is $OCH_2CH_3$.

In yet another preferred embodiment of the invention, the compounds of formula III are compounds, wherein $R^1$, $R^2$ and $R^3$ are as defined in Tables 1 to 153, and wherein X is $N(CH_3)_2$.

In yet another preferred embodiment of the invention, the compounds of formula III are compounds, wherein $R^1$, $R^2$ and $R^3$ are as defined in Tables 1 to 153, and wherein X is $N(CH_2CH_3)_2$.

The compounds of formula II do not contain any further substituents apart from the substituents $R^4$ and $R^5$, which were already discussed above. It is again noted, however, that the substituents $R^4$ and $R^5$ may preferably be selected in accordance with Table A above.

The compounds of formula II are obtainable from the compounds of formula I by reacting them with hydrazine.

The compounds of formula I do not contain any further substituents apart from substituents $R^4$ and $R^5$, which were already discussed above, and may particularly preferably selected in accordance with Table A.

With regard to hydrazine as a reagent to be reacted with the compounds of formula I in the process of the present invention, the following is noted.

Hydrazine (also called diazane) is a compound with the formula $H_2N$—$NH_2$. Although hydrazine may principally be used in anhydrous form, it is preferred that hydrazine is used in the form of an organic solution or that hydrazine is used in the form of the monohydrate $H_2N$—$NH_2 \times H_2O$ or in the form of an aqueous solution of said monohydrate. It is particularly preferred that hydrazine is used in the form of the monohydrate $H_2N$—$NH_2 \times H_2O$ or in the form of an aqueous solution of said monohydrate.

If hydrazine is used in a solution in an organic solvent, the solvent is preferably an alcohol, e.g. isopropanol, ethanol or methanol. Preferred concentrations for alcoholic hydrazine solutions are in the range of from 20% to 50% by weight, preferably 34% to 50% by weight of hydrazine, based on the total weight of the solution. It is particularly preferred that hydrazine and the alcohol are present in a weight ratio of about 1:1 in such alcoholic solutions.

If hydrazine is used in a solution in an aqueous solvent, the solvent is preferably water, and the concentration typically refers to the concentration of the monohydrate of hydrazine ($H_2N$—$NH_2 \times H_2O$). Preferred concentrations for aqueous hydrazine monohydrate solutions are in the range of 45 to 100% by weight, preferably 60 to 100% by weight, e.g., 80 to 100% or 70 to 90% by weight of hydrazine monohydrate based on the total weight of the solution. Preferably, hydrazine is used as 100% hydrazine monohydrate or as an aqueous solution of hydrazine monohydrate with a concentration of about 80 wt.-% of hydrazine monohydrate based on the total weight of the solution.

Alternatively, hydrazine may be used in the form of a salt. Hydrazine can easily be converted into salts by treatment with mineral or organic acids such as sulfuric acid, hydrochloric acid or acetic acid to give, e.g. salts of the formula [$H_2N$—$NH_3$]$^+$$HSO_4^-$, [$H_2N$—$NH_3$]$^+$$Cl^-$ or [$H_2N$—$NH_3$]$^+$ [$O(C$=$O)CH_3$]$^-$, respectively. In certain preferred embodiments, hydrazine may be used in the form of an acetate or hydrochloride salt in the process according to the present invention. The salt may be added to the reaction mixture as a solid or in solution in an organic or aqueous solvent, e.g. in methanol, ethanol, isopropanol or water.

As already indicated above, the compounds of formula V may be present as compounds of formula Va, Vb or Vc.

In principal, the same combinations of substituents $R^1$, $R^2$, $R^3$, $R^4$ and $R^5$ as defined in the above tables 1 to 153 in combination with table A, entries A-1 to A-159 are also preferred for the compounds of formulae Va, Vb and Vc and the compounds, which are obtainable from the compounds of formula Vc, namely the compounds of formulae VI and VIII. It is noted, however, that these generic formulae are already pre-defined in terms of the substituent $R^1$, so that only the specific combinations of $R^2$, $R^3$, $R^4$ and $R^5$ may be derived from the above tables.

The compounds of formula Va, Vb and Vc fall under the definition of the compounds of formula V, if $R^1$ is selected as such that $R^1$ is CN (compound of formula Vb) or $C(O)OR^c$ (compound of formula Va) or C(O)OH (compound of formula Vc). If $R^1$ in the compounds of formula V is $C(O)OR^c$, it is further preferred that $R^c$ is $C_1$-$C_4$-alkyl, e.g. $CH_3$, $CH_2CH_3$, $C(CH_3)_3$, or that $R^1$ is aryl-$C_1$-$C_4$-alkyl, e.g. $CH_2C_6H_5$.

For the remaining substituents, the same substituent definitions are preferred as discussed above in tables 1 to 153 in combination with table A. Furthermore, $R^6$ is preferably H, CN, $CHF_2$, or $CF_3$.

Thus, in one preferred embodiment of the invention, the compounds of formula Vb are compounds, wherein $R^2$, $R^3$, $R^4$, and $R^5$ are according to any one of Tables 1 to 153 in combination with table A, entries A-1 to A-159, and wherein $R^6$ is H.

Furthermore, in one preferred embodiment of the invention, the compounds of formula Va are compounds, wherein $R^2$, $R^3$, $R^4$, and $R^5$ are according to any one of Tables 1 to 153 in combination with table A, entries A-1 to A-159, and wherein $R^6$ is H, and wherein $R^c$ is $CH_3$.

In another preferred embodiment of the invention, the compounds of formula Va are compounds, wherein $R^2$, $R^3$, $R^4$, and $R^5$ are according to any one of Tables 1 to 153 in combination with table A, entries A-1 to A-159, and wherein $R^6$ is H, and wherein $R^c$ is $CH_2CH_3$.

In another preferred embodiment of the invention, the compounds of formula Va are compounds, wherein $R^2$, $R^3$, $R^4$, and $R^5$ are according to any one of Tables 1 to 153 in combination with table A, entries A-1 to A-159, and wherein $R^6$ is H, and wherein $R^c$ is $C(CH_3)_3$.

In another preferred embodiment of the invention, the compounds of formula Va are compounds, wherein $R^2$, $R^3$, $R^4$, and $R^5$ are according to any one of Tables 1 to 153 in combination with table A, entries A-1 to A-159, and wherein $R^6$ is H, and wherein $R^c$ is $CH_2C_6H_5$.

Moreover, in one preferred embodiment of the invention, the compounds of formula Vc are compounds, wherein $R^2$, $R^3$, $R^4$, and $R^5$ are according to any one of Tables 1 to 153 in combination with table A, entries A-1 to A-159, and wherein $R^6$ is H.

Further to the above discussed preferred substituent combinations, it can be preferred for the compounds of formula Va, Vb and Vc that
$R^2$ is $CH_3$ or halomethyl,
$R^3$ is H,
$R^4$ is $C_1$-$C_4$-alkyl, $C_1$-$C_2$-haloalkyl, or $C_3$-cycloalkyl, wherein the cycloalkyl group is preferably substituted with one substituent selected from CN and $C(O)NH_2$,
$R^5$ is $C_1$-$C_2$-alkyl or $C_3$-$C_4$-cycloalkyl,
or $R^4$ and $R^5$ together with the carbon atom to which they are attached form a 6-membered carbocycle, which is partially or fully halogenated, preferably fluorinated, and $R^6$ is H.

In view of the fact that the above compounds of formulae Va, Vb and Vc are versatile reaction tools for obtaining further pyrazole derivatives, the substituents of the compounds of formula V are particularly preferably selected as such that $R^2$ is $CH_3$, $R^3$ is H, $R^6$ is H and the remaining substituent definitions are selected as indicated in one of the rows B-1 to B-30 of Table B.

TABLE B

| | $R^1$ | $R^4$ | $R^5$ |
|---|---|---|---|
| B-1 | CN | $CH(CH_3)_2$ | $CH_3$ |
| B-2 | CN | $CHFCH_3$ | $CH_3$ |
| B-3 | CN | 1-CN-$cC_3H_4$ | $CH_3$ |
| B-4 | CN | 1-$C(O)NH_2$-$cC_3H_4$ | $CH_3$ |
| B-5 | CN | | $CH_2CH_2CF_2CH_2CH_2$ |
| B-6 | $C(O)OCH_3$ | $CH(CH_3)_2$ | $CH_3$ |
| B-7 | $C(O)OCH_3$ | $CHFCH_3$ | $CH_3$ |
| B-8 | $C(O)OCH_3$ | 1-CN-$cC_3H_4$ | $CH_3$ |
| B-9 | $C(O)OCH_3$ | 1-$C(O)NH_2$-$cC_3H_4$ | $CH_3$ |
| B-10 | $C(O)OCH_3$ | | $CH_2CH_2CF_2CH_2CH_2$ |
| B-11 | $C(O)OCH_2CH_3$ | $CH(CH_3)_2$ | $CH_3$ |
| B-12 | $C(O)OCH_2CH_3$ | $CHFCH_3$ | $CH_3$ |
| B-13 | $C(O)OCH_2CH_3$ | 1-CN-$cC_3H_4$ | $CH_3$ |
| B-14 | $C(O)OCH_2CH_3$ | 1-$C(O)NH_2$-$cC_3H_4$ | $CH_3$ |
| B-15 | $C(O)OCH_2CH_3$ | | $CH_2CH_2CF_2CH_2CH_2$ |
| B-16 | $C(O)OC(CH_3)_3$ | $CH(CH_3)_2$ | $CH_3$ |
| B-17 | $C(O)OC(CH_3)_3$ | $CHFCH_3$ | $CH_3$ |
| B-18 | $C(O)OC(CH_3)_3$ | 1-CN-$cC_3H_4$ | $CH_3$ |
| B-19 | $C(O)OC(CH_3)_3$ | 1-$C(O)NH_2$-$cC_3H_4$ | $CH_3$ |
| B-20 | $C(O)OC(CH_3)_3$ | | $CH_2CH_2CF_2CH_2CH_2$ |
| B-21 | $C(O)OCH_2C_6H_5$ | $CH(CH_3)_2$ | $CH_3$ |
| B-22 | $C(O)OCH_2C_6H_5$ | $CHFCH_3$ | $CH_3$ |
| B-23 | $C(O)OCH_2C_6H_5$ | 1-CN-$cC_3H_4$ | $CH_3$ |
| B-24 | $C(O)OCH_2C_6H_5$ | 1-$C(O)NH_2$-$cC_3H_4$ | $CH_3$ |
| B-25 | $C(O)OCH_2C_6H_5$ | | $CH_2CH_2CF_2CH_2CH_2$ |
| B-26 | C(O)OH | $CH(CH_3)_2$ | $CH_3$ |
| B-27 | C(O)OH | $CHFCH_3$ | $CH_3$ |
| B-28 | C(O)OH | 1-CN-$cC_3H_4$ | $CH_3$ |
| B-29 | C(O)OH | 1-$C(O)NH_2$-$cC_3H_4$ | $CH_3$ |
| B-30 | C(O)OH | | $CH_2CH_2CF_2CH_2CH_2$ |

Rows B-1 to B-5 correspond to preferred compounds of formula Vb, rows B-6 to B-25 correspond to preferred compounds of formula Va and rows B-26 to B-30 correspond to preferred compounds of formula Vc, which may be used in the process of the present invention.

As already indicated above, the compounds of formula Va and Vb can be obtained from the compounds of formula IV according the present invention. The compounds of formula Vc are obtainable from the compounds of formula Va or Vb. Alternatively, the compounds of formula Vc may directly be obtained from the compounds of formula IV according the present invention.

The compounds of formula Vc may be further converted into compounds of formula VI according to the present invention.

Apart from the substituents discussed above, the compounds of formula VI further comprise a substituent $X^1$, which represents a leaving group. In principal, any leaving group, which is known in the art, e.g. in the context of activated carboxylic acid derivatives, is suitable as substituent $X^1$.

For example, $X^1$ may be a leaving group, which is based on a peptide coupling reagent. Suitable peptide coupling reagents are described by Han et al. in Tetrahedron 60 (2004) 2447-2467. In this regard, N,N'-bis(2-oxo-3-oxazolidinyl)-phosphinic chloride (BOP-Cl) and O-(7-azabenzotriazol-1-yl)-1,1,3,3-tetramethyluronium hexafluorophosphate (HATU) are preferred according to the present invention.

Furthermore, $X^1$ may be a leaving group selected from active esters, azide and halogens.

In a preferred embodiment of the invention,
$X^1$ is halogen, $N_3$, p-nitrophenoxy, or pentafluorophenoxy.

Preferably, $X^1$ is halogen, in particular Cl.

Thus, in one preferred embodiment of the invention, the compounds of formula VI are compounds, wherein $R^2$, $R^3$, $R^4$, and $R^5$ are according to any one of Tables 1 to 153 in combination with table A, entries A-1 to A-159, and wherein $R^6$ is H, and wherein $X^1$ is Cl.

In another preferred embodiment of the invention, the compounds of formula VI are compounds, wherein $R^2$, $R^3$, $R^4$, and $R^5$ are according to any one of Tables 1 to 153 in combination with table A, entries A-1 to A-159, and wherein $R^6$ is H, and wherein $X^1$ is $N_3$.

In another preferred embodiment of the invention, the compounds of formula VI are compounds, wherein $R^2$, $R^3$, $R^4$, and $R^5$ are according to any one of Tables 1 to 153 in combination with table A, entries A-1 to A-159, and wherein $R^6$ is H, and wherein $X^1$ is p-nitrophenoxy.

In another preferred embodiment of the invention, the compounds of formula VI are compounds, wherein $R^2$, $R^3$, $R^4$, and $R^5$ are according to any one of Tables 1 to 153 in combination with table A, entries A-1 to A-159, and wherein $R^6$ is H, and wherein $X^1$ is pentafluorophenoxy.

The compounds of formula VI may be further converted into compounds of formula VIII.

In the process of preparing the compounds of formula VIII as described above, the substituent $X^1$ of the compounds of formula VI is substituted by the amine group of the N-(het)arylamine of formula VII, so that the substituent is no longer contained in the compounds of formula VIII.

However, apart from the remaining substituents discussed above, the compounds of formula VIII further comprise the N-(het)arylamide group, wherein the amide nitrogen atom is substituted by $R^{1N}$ and the (het)aryl group comprises a substituent U and substituents $R^{P1}$, $R^{P2}$ and $R^{P3}$. The same substituents are also present in the compounds of formula VII, with which the compounds of formula VI may be reacted to give the compounds of formula VIII.

In a preferred embodiment of the invention,
U is N or CH;
$R^{P1}$, $R^{P2}$, $R^{P3}$ are H; and
$R^{1N}$ is H, $C_1$-$C_2$-alkyl or $C_1$-$C_2$-alkoxy-$C_1$-$C_2$-alkyl.

In particular, the following combinations of substituents U, $R^{P1}$, $R^{P2}$, $R^{P3}$ and $R^{1N}$ according to Table C are preferred in the compounds of formula VII and VIII.

TABLE C

| | U | $R^{P1}$, $R^{P2}$, $R^{P3}$ | $R^{1N}$ |
|---|---|---|---|
| C-1 | N | H | H |
| C-2 | N | H | $CH_3$ |
| C-3 | N | H | $CH_2CH_3$ |

TABLE C-continued

| | U | $R^{P1}$, $R^{P2}$, $R^{P3}$ | $R^{1N}$ |
|---|---|---|---|
| C-4 | N | H | $CH_2OCH_3$ |
| C-5 | N | H | $CH_2OCH_2CH_3$ |
| C-6 | N | H | $CH_2CH_2OCH_3$ |
| C-7 | N | H | $CH_2CH_2OCH_2CH_3$ |
| C-8 | CH | H | H |
| C-9 | CH | H | $CH_3$ |
| C-10 | CH | H | $CH_2CH_3$ |
| C-11 | CH | H | $CH_2OCH_3$ |
| C-12 | CH | H | $CH_2OCH_2CH_3$ |
| C-13 | CH | H | $CH_2CH_2OCH_3$ |
| C-14 | CH | H | $CH_2CH_2OCH_2CH_3$ |

Thus, in a preferred embodiment of the invention, the compounds of formula VII are compounds, wherein U, $R^{P1}$, $R^{P2}$, $R^{P3}$, and $R^{1N}$ are as defined in any one of rows C-1 to C-14 of table C.

Furthermore, in a preferred embodiment of the invention, the compounds of formula VI II are compounds, wherein $R^2$, $R^3$, $R^4$, and $R^5$ are according to any one of Tables 1 to 153 in combination with table A, entries A-1 to A-159, and wherein $R^6$ is H, and wherein U, $R^{P1}$, $R^{P2}$, $R^{P3}$, and $R^{1N}$ are as defined in any one of rows C-1 to C-14 of table C.

As already indicated above, the present invention is also directed to compounds of formulae Va, Vb, Vc and VI.

In one embodiment, the present invention relates to a compound of formula Va or a salt, stereoisomer, tautomer or N-oxide thereof

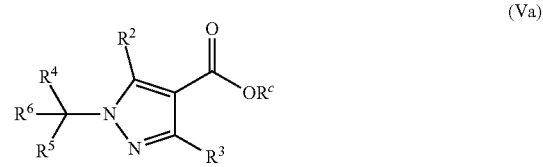

(Va)

wherein
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is 1-CN-$cC_3H_4$, $R^5$ is $CH_3$ and $R^6$ is H; or
$R^2$ is $CH_3$, $R_3$ is H, $R^4$ is 1-C(O)$NH_2$-$cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H;
and wherein
$R^c$ is $C_1$-$C_4$-alkyl or aryl-$C_1$-$C_4$-alkyl, or wherein $R^c$ together with the C(O)O group forms a salt [C(O)O]$^-$NR$_4^+$, [C(O)O]$^-$M$_a^+$ or [C(O)O]$^-$½M$_{ea}^{2+}$, wherein M$_a$ is an alkali metal and M$_{ea}$ is an alkaline earth metal; and wherein the substituents R at the nitrogen atom are independently of each other selected from H, $C_1$-$C_{10}$-alkyl, phenyl and phenyl-$C_1$-$C_4$-alkyl.

If $R^c$ together with the C(O)O group forms a salt, the salt is preferably selected from [C(O)O]$^-$NH$_4^+$, [C(O)O]$^-$Na$^+$, [C(O)O]$^-$K$^+$, [C(O)O]$^-$½Ca$^{2+}$ and [C(O)O]$^-$½Mg$^{2+}$, and is particularly preferably [C(O)O]$^-$Na$^+$. If $R^c$ together with the C(O)O group forms a salt, this is to be understood as a carboxylate salt, wherein the negative charge is delocalized in the carboxylate group [C(O)O]–.

If $R^c$ is selected as such that the C(O)O$R^c$ group is an ester group, it is preferred that $R^c$ is $C_1$-$C_4$-alkyl or benzyl, more preferably, ethyl or tert-butyl.

It is particularly preferred according to the invention that $R^c$ is selected as such that the C(O)OR$^c$ group is an ester group. In this context, $C_1$-$C_4$-alkyl or benzyl ester groups are particularly preferred.

In another embodiment, the present invention relates to a compound of formula Vb or a salt, stereoisomer, tautomer or N-oxide thereof

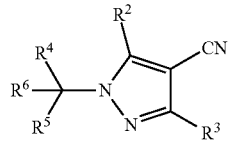

(Vb)

wherein
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is 1-CN-$cC_3H_4$, $R^5$ is $CH_3$ and $R^6$ is H; or
$R^2$ is $CH_3$, $R_3$ is H, $R^4$ is 1-C(O)NH$_2$-$cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H.

In yet another embodiment, the present invention relates to a compound of formula Vc or a salt, stereoisomer, tautomer or N-oxide thereof

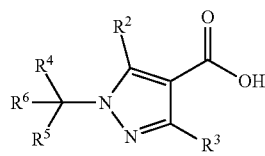

(Vc)

wherein
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is 1-CN-$cC_3H_4$, $R^5$ is $CH_3$ and $R^6$ is H; or
$R^2$ is $CH_3$, $R_3$ is H, $R^4$ is 1-C(O)NH$_2$-$cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H.

In yet another embodiment, the present invention relates to a compound of formula VI or a salt, stereoisomer, tautomer or N-oxide thereof

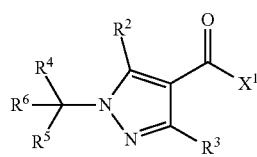

(VI)

wherein
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is 1-CN-$cC_3H_4$, $R^5$ is $CH_3$ and $R^6$ is H; or
$R^2$ is $CH_3$, $R_3$ is H, $R^4$ is 1-C(O)NH$_2$-$cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H;
and wherein
$X^1$ is a leaving group.

Suitable leaving groups include leaving groups, which are known in the art in the context of activated carboxylic acid derivatives.

For example, $X^1$ may be a leaving group, which is based on a peptide coupling reagent. Suitable peptide coupling reagents are described by Han et al. in Tetrahedron 60 (2004) 2447-2467. In this regard, N,N'-bis(2-oxo-3-oxazolidinyl)-phosphinic chloride (BOP-Cl) and O-(7-azabenzotriazol-1-yl)-1,1,3,3-tetramethyluronium hexafluorophosphate (HATU) are preferred according to the present invention.

Furthermore, $X^1$ may be a leaving group selected from active esters, azide and halogens.

Preferably, $X^1$ is selected from halogen, $N_3$, p-nitrophenoxy and pentafluorophenoxy, and more preferably, $X^1$ is halogen, and particularly preferably $X^1$ is Cl.

As already indicated above, the process of the present invention covers the preparation of a compound of formula V by cyclizing a compound of formula IV by reacting it with a reagent comprising a $R^6$ group. Said reaction step provides for the benefits of the present invention, namely the versatile and convenient provision of compounds of formula V, thereby preferably ensuring regioselectivity. Preferably, the process of the present invention also includes the preparation of the compounds of formula IV, so that in particular a reaction sequence of the following steps (b) and (c) or the steps (a), (b) and (c) is covered by the present invention:

(a) I→II:

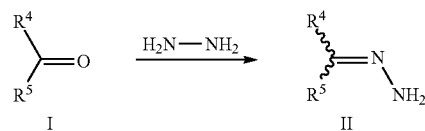

(b) II+μl→IV:

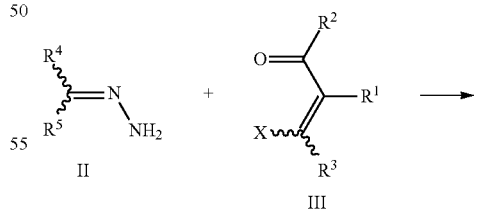

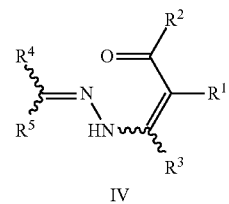

IV (c) IV→V:

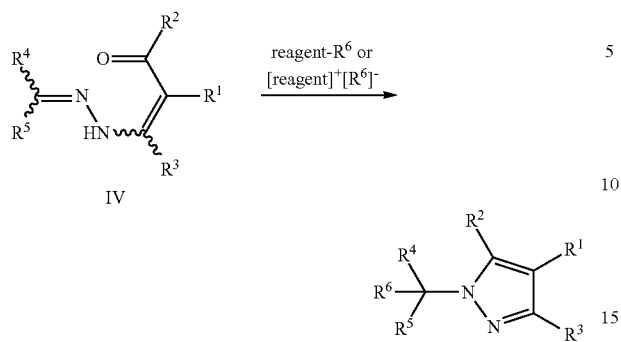

It is emphasized that the above reaction steps may not only be performed separately, i.e. under isolation of the compounds of formulae II and IV, but that the reaction steps may also be performed in a one-pot reaction, i.e. without isolating the compounds of formulae II and/or IV.

One option is that steps (a), (b) and (c) are combined in a one-pot reaction, e.g. by combining the compounds of formula I with hydrazine, so that first the compound of formula II is in situ formed, then adding the compound of formula III to give the compound of formula IV in situ, and then adding the reagent comprising the $R^6$ group to give a compound of formula V. Another option is that steps (a) and (b) are performed in a one-pot reaction and the compound of formula IV is isolated, and that then step (c) is performed. And yet another option is that step (a) is performed as a first step and the compound of formula II is isolated, and that then steps (b) and (c) are then performed in a one-pot reaction.

Furthermore, it is emphasized that the reactions may be performed on a technical scale. Preferably, the reactants are converted equally well and only minor deviations in terms of yield are observed.

As also already discussed above, the compounds of formula V are versatile reaction tools for the preparation of pesticidally active agents. For example, if the compounds of formula V are compounds of formula Va or Vb, these compounds may be converted into compounds of formula Vc. The compounds of formula Vc, which can either be obtained from the compounds of formula Va or Vb or as a reaction product of the above reaction step (c), can then be further converted into compounds of formula VI. In a further reaction step, the compounds of formula VIII may then be obtained. Thus, the following reaction sequence comprising step (d), preferably step (d) and step (e), and particularly preferably steps (d), (e) and (f), may be performed subsequent to the above reaction sequence according to the present invention.

(d) Va or Vb→Vc:

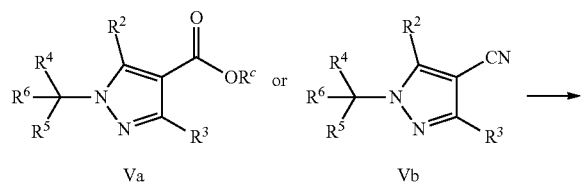

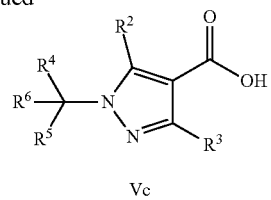

(e) Vc→VI:

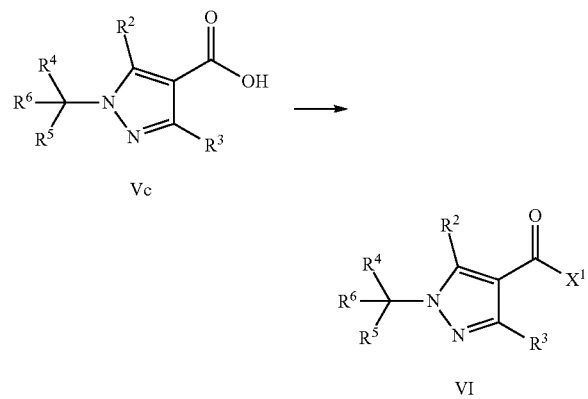

(f) VI+VII→VIII:

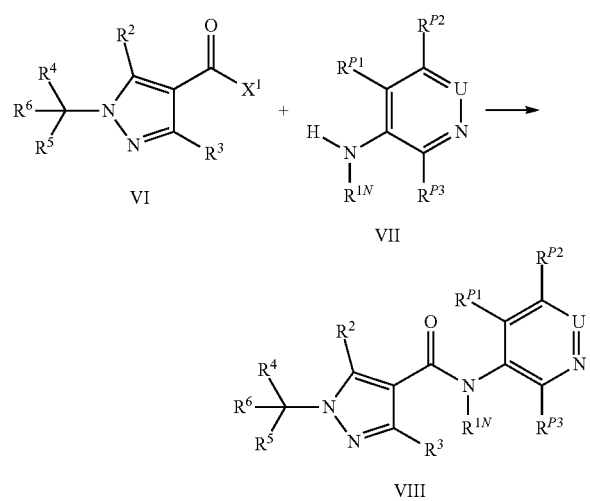

It is noted that also steps (e) and (f) may be performed as a one-pot reaction so that the activated compound VI does not have to be isolated prior to the amidation reaction.

The above reaction steps of the process of the invention will be described hereinafter, wherein it will be referred to the steps (a), (b), (c), (d), (e) and (f) as indicated above with step (c) being the essential step of the process of the present invention.

The reaction steps of the process of the invention as described hereinafter are performed in reaction vessels customary for such reactions, the reactions being carried out in a continuous, semi-continuous or batchwise manner.

In general, the particular reactions will be carried out under atmospheric pressure. The reactions may, however, also be carried out under reduced pressure.

The temperatures and the duration times of the reactions may be varied in broad ranges, which the person skilled in the art knows from analogous reactions. The temperatures often depend on the reflux temperature of the solvents. Other reactions are preferably performed at room temperature, i.e. at about 25° C., or under ice cooling, i.e. at about 0° C. The end of the reaction can be monitored by methods known to a person skilled in the art, e.g. thin layer chromatography or HPLC.

If not otherwise indicated, the molar ratios of the reactants, which are used in the reactions, are in the range of from 0.2:1 to 1:0.2, preferably from 0.5:1 to 1:0.5, more preferably from 0.8:1 to 1:0.8. Preferably, equimolar amounts are used.

If not otherwise indicated, the reactants can in principle be contacted with one another in any desired sequence.

The person skilled in the art knows when the reactants or reagents are moisture sensitive, so that the reaction should be carried out under protective gases such as under a nitrogen atmosphere, and dried solvents should be used.

The person skilled in the art also knows the best work-up of the reaction mixture after the end of the reaction.

In the following, the process of the invention is described in further detail.

The reaction conditions for step (a) of the process are as follows.

In step (a) of the process of the invention, a compound of formula I is reacted with hydrazine to give a compound of formula II. Said reaction is a hydrazone formation, which can be performed under reaction conditions known in the art. In particular, the reaction can be carried out by a process, wherein hydrazine monohydrate or a solution of hydrazine, is reacted with a compound of formula I either in the absence of a solvent or in an aqueous or organic solvent, wherein a basic or an acidic catalyst may optionally be present.

In a preferred embodiment the reaction is conducted in the absence of a solvent.

In a preferred embodiment the reaction is conducted in the absence of a catalyst.

Suitable reaction temperatures for the reaction are in the range of from 0° C. to 80° C., preferably from 15° C. to 50° C., more preferably from 20 to 25° C. In certain situations it can be preferred to start at a lower temperature of from 20 to 25° C. for about 1 hour and then heat the reaction mixture to a higher temperature of from 50 to 80° C. In other situations, it can be preferred to start at a medium temperature of from 30 to 50° C. for about 1 hour and then stir the reaction mixture at a temperature of from 20 to 25° C.

The overall reaction times may vary in a broad range, e.g. from 1 hour to 3 days. It is therefore preferred that the reaction is monitored by analytical methods and stopped after complete conversion of the compound of formula I into formula II.

The compound of formula I is commercially available or can be prepared by methods known in the art.

As already indicated above, hydrazine is preferably provided in the form of the monohydrate or in the form of a solution of said monohydrate in water. Preferred concentrations for aqueous hydrazine monohydrate solutions are in the range of 45 to 100% by weight, preferably 60 to 100% by weight, e.g., 80 to 100% or 70 to 90% by weight of hydrazine monohydrate based on the total weight of the solution. Preferably, hydrazine is used as 100% hydrazine monohydrate or as an aqueous solution of hydrazine monohydrate with a concentration of about 80 wt.-% of hydrazine monohydrate based on the total weight of the solution.

Preferably, hydrazine is used at least in stochiometric amounts. Preferably, hydrazine is used in amounts in the range of from 1.0 to 10.0 mol, preferably from 1.0 to 2.0 mol, more preferably from 1.0 to 1.5 mol, per mol of the compound of formula I.

For practical reasons, it is preferred that the compound of formula I is added to hydrazine monohydrate or a solution thereof and not vice versa, so that it is avoided that an excess of the compound of formula I compared to hydrazine is present in the reaction mixture upon mixing the two components.

If a solvent is present, it is preferred that the solvent is an organic solvent, either an aprotic or a protic solvent or a mixture thereof. Suitable aprotic solvents include aromatic solvents, ethers, or mixtures thereof. Preferred aromatic solvents are e.g. benzene, toluene, xylene (ortho-xylene, meta-xylene or para-xylene), mesitylene, chlorobenzene, 1,2-dichlorobenzene, 1,3-dichlorobenzene, 1,4-dichlorobenzene, or mixtures thereof. Preferred ethers are open-chained and cyclic ethers, in particular diethyl ether, methyl-tert-butyl-ether (MTBE), 2-methoxy-2-methylbutane, cyclopentylmethylether, 1,4-dioxane, tetrahydrofuran, 2-methyltetrahydrofuran, or mixtures thereof. Protic solvents are typically preferred as solvents. Suitable protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Particularly preferred are $C_1$-$C_4$-alkanols, e.g. methanol, ethanol, isopropanol, butanol, or mixtures thereof, in particular ethanol.

The reaction may also be performed in the presence of an acidic or basic catalyst. Preferred acid catalysts include HCl in $H_2O$, HCl in MeOH, HCl in dioxane; $H_2SO_4$, $H_3PO_4$ and salts of $H_2SO_4$ and $H_3PO_4$; aromatic sulfonic acids such as toluene sulfonic acid; alkylsulfonic acids, such as methyl sulfonic acid; aromatic carboxylic acids such as benzoic acid; alkylcarboxylic acids such as acetic acid; salts of rare earth metals; and Lewis acids such as $BF_3$, $BF_3 \times OEt_2$, $BF_3 \times SMe_2$, $TiCl_4$, $Ti(OiPr)_4$. A preferred acid catalyst is acetic acid. Preferred basic catalysts include BaO, CaO, $MgCO_3$, $CaCO_3$, $Na_2CO_3$, $K_2CO_3$ and $NEt_3$. A preferred basic catalyst is BaO.

The acidic or basic catalyst is preferably used in amounts in the range of from 0.001 to 10 mol, preferably from 0.01 to 0.5 mol, more preferably from 0.02 to 0.3 mol, per mol of the compound of formula I. For acidic catalysts, amounts in the range of from 0.05 to 0.2 mol per mol of the compound of formula I can be preferred. For basic catalysts, amounts in the range of from 0.15 to 0.25 or from 0.2 to 0.3 mol per mol of the compound of formula I can be preferred.

The reaction conditions for step (b) of the process of the invention are as follows.

In step (b), a compound of formula II is reacted with a compound of formula III to give a compound of formula IV. Said reaction corresponds to a substitution reaction at an α,β-unsaturated carbonyl compound comprising a leaving group in the β-position with a hydrazone acting as a nucleophile. The reaction can be performed under reaction conditions known in the art. In particular, the reaction can be carried out by a process, wherein the compound of formula II is reacted with a compound of formula III either in the absence of a solvent or in an organic solvent, wherein a basic catalyst may optionally be present.

Suitable reaction temperatures for the reaction are in the range of from −20° C. to 50° C., preferably from 15° C. to 40° C., more preferably from 20 to 25° C. It is typically preferred that the compounds of formulae II and III are mixed with each other at temperatures below 0° C., preferably about −20° C., and that the mixture is then allowed to warm to a reaction temperature defined above.

The overall reaction times may vary in a broad range, e.g. from 1 hour to 1 day, preferably from 3 to 12 hours.

The compound of formula II may be provided as the crude product of step (a), i.e. without performing any purification steps prior to step (b), or as part of the reaction mixture obtained in step (a), to which the compound of formula III may then be added.

The compound of formula III is commercially available or can be prepared by methods known in the art.

Preferably, the compound of formula III is used in amounts in the range of from 0.1 to 10.0 mol, preferably from 0.8 to 1.5 mol, more preferably from 0.9 to 1.3 mol per mol of the compound of formula II.

If a solvent is present, it is preferred that the solvent is an organic solvent, either an aprotic or a protic solvent or a mixture thereof. Suitable aprotic solvents include aromatic solvents, ethers, or mixtures thereof. Preferred aromatic solvents are e.g. benzene, toluene, xylene (ortho-xylene, meta-xylene or para-xylene), mesitylene, chlorobenzene, 1,2-dichlorobenzene, 1,3-dichlorobenzene, 1,4-dichlorobenzene, or mixtures thereof. Preferred ethers are open-chained and cyclic ethers, in particular diethyl ether, methyl-tert-butyl-ether (MTBE), 2-methoxy-2-methylbutane, cyclopentylmethylether, 1,4-dioxane, tetrahydrofuran, 2-methyltetrahydrofuran, or mixtures thereof. A particularly suitable open-chained ether is e.g. MTBE. Protic solvents are typically preferred as solvents. Suitable protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Particularly preferred are $C_1$-$C_4$-alkanols, e.g. methanol, ethanol, isopropanol, butanol, or mixtures thereof, in particular ethanol.

In principal, the reaction can easily be performed without having to use a catalyst. However, the reaction may also be performed in the presence of a basic catalyst. Preferred basic catalysts include BaO, CaO, $MgCO_3$, $CaCO_3$, $Na_2CO_3$, $K_2CO_3$ and $NEt_3$.

If a basic catalyst is used, amounts in the range of from 0.01 to 2.0 mol, preferably from 1.0 to 2.0 mol, per mol of the compound of formula II are preferred.

The reaction conditions for step (c) of the process of the invention are as follows.

In step (c), a compound of formula IV is reacted with a reagent comprising a $R^6$ group to give a compound of formula V. The reaction conditions are described hereinafter. In particular, the reaction can be carried out by a process, wherein the compound of formula IV is reacted with the reagent comprising the $R^6$ group either in the presence of a solvent, wherein an acidic catalyst or a metal catalyst may optionally be present.

The selection of the solvent depends on the type of the reagent comprising the $R^6$ group. In general organic solvents including aprotic solvents, such as aromatic solvents, ethers or mixtures thereof, and protic solvents may be used. Preferred aromatic solvents are e.g. benzene, toluene, xylene (ortho-xylene, meta-xylene or para-xylene), mesitylene, chlorobenzene, 1,2-dichlorobenzene, 1,3-dichlorobenzene, 1,4-dichlorobenzene, or mixtures thereof. Preferred ethers are open-chained and cyclic ethers, in particular diethyl ether, methyl-tert-butyl-ether (MTBE), 2-methoxy-2-methylbutane, cyclopentylmethylether, 1,4-dioxane, tetrahydrofuran, 2-methyltetrahydrofuran, or mixtures thereof. Preferred protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Particularly preferred are $C_1$-$C_4$-alkanols, e.g. methanol, ethanol, isopropanol, butanol, or mixtures thereof.

If the reagent is reducing agent, preferably an ionic hydride donor, protic organic solvents can be preferred. Suitable protic solvents include $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Particularly preferred are $C_1$-$C_4$-alkanols, e.g. methanol, ethanol, isopropanol, butanol, or mixtures thereof, in particular methanol, ethanol and isopropanol. If the reducing agent is an ionic hydride donor of higher reactivity, such as in case of $Li[AlH_4]^-$, it can be preferred that the solvent is an aprotic organic solvent, e.g. an ether solvent such as diethyl ether, methyl-tert-butyl ether (MTBE), 2-methoxy-2-methylbutane, cyclopentylmethylether, 1,4-dioxane, tetrahydrofuran, 2-methyltetrahydrofuran, or mixtures thereof. Ether solvents such as the ones listed above are also preferred, if the reagent is a non-ionic hydride donor.

On the other hand, protic solvents as mentioned above are again preferred, if electron donors are used in combination with protons to act as a reducing agent because protons are required for the in situ formation of hydrogen radicals.

If the reagent is an organometallic agent, aprotic organic solvents are typically preferred. Suitable aprotic solvents include aliphatic hydrocarbons, cycloaliphatic hydrocarbons, halogenated alkanes, aromatic hydrocarbons, open-chained ethers, cyclic ethers, esters, aliphatic or alicyclic carbonates, in particular aromatic solvents and open-chained and cyclic ethers. Preferred aprotic solvents are open-chained and cyclic ethers. Preferred open-chained ethers are diethyl ether, methy-tert-butyl ether (MTBE), 2-methoxy-2-methylbutane and cyclopentylmethylether. Preferred cyclic ethers are tetrahydrofuran, 2-methyltetrahydrofuran and 1,4-dioxane.

If the reagent is a nucleophilic reagent, both protic and aprotic organic solvents may be used.

Protic solvents such as $C_1$-$C_4$-alkanols, in particular methanol, ethanol and isopropanol, can again be preferred.

The reaction temperatures also depend on the type of the reagent comprising the $R^6$ group.

If the reagent is a reducing agent, the reaction temperatures may be in the range of from −20° C. to 50° C., preferably from 10° C. to 30° C., more preferably from 20° C. to 25° C. In certain situations, it can be preferred to start the reaction at a higher temperature of from 30° C. to 50° C. and then continue the reaction at room temperature.

If the reagent is an organometallic reagent, lower reaction temperatures of −78° C. to 0° C. may be suitable. Alternatively, the reaction temperature may be in the range of from 0° C. to 50° C., preferably from 10° C. to 30° C., more preferably from 20 to 25° C. In certain situations it can be preferred to start at a lower temperature of about −78° C., −20° C. or 0° C. for about 1 hour and then allow the reaction mixture to warm to a temperature of from 0° C. to 25° C.

If the reagent is a nucleophilic reagent, the reaction temperatures may be in the range of from 0° C. to 50° C., preferably from 10° C. to 30° C., more preferably from 20 to 25° C. Alternatively, it can be preferred that the reaction mixture is heated, e.g. to a reaction temperature of from 50° C. to 80° C.

The overall reaction times may vary in a broad range, preferably from 1 hour to 4 days, e.g. from 4 hours to 8 hours, from 10 to 18 hours, from 24 hours to 48 hours, or from 2 days to 4 days. It is therefore preferred that the reaction is monitored by analytical methods and stopped after complete conversion of the compound of formula IV into the compound of formula V.

The compound of formula IV can be provided as a crude product of step (b), i.e. without performing any purification steps prior to step (c), or as part of the reaction mixture obtained in step (b), to which the reagent comprising the $R^6$ group may then be added.

The reagent comprising the $R^6$ group is preferably used at least in stochiometric amounts, e.g. in amounts in the range of from 1.0 to 10.0 mol, preferably from 1.0 to 2.0 mol per mol of the compound of formula IV. If the reagent comprises more than one $R^6$ groups, which may be transferred, it can also be sufficient to use sub-stochiometric amounts, e.g. in the range of from 0.1 to less than 1.0 mol, preferably 0.5 to less than 1.0 mol per mol of the compound of formula IV. In principal, the reagent may therefore be used in amounts in the range of from 0.1 to 10.0 mol per mol of the compound of formula IV. Preferably, the reagent is used in amounts of from 0.8 to 2.0 mol, more preferably from 1.0 to 1.5 mol, per mol of the compound of formula IV.

If the reagent comprising the $R^6$ group is in gaseous form, e.g. in case of dihydrogen, the reagent is typically used in an excess by performing the reaction in an atmosphere of the reagent comprising the $R^6$ group. A certain pressure may be applied, which preferably does not exceed 100 bar for practical reasons.

The reagent comprising the $R^6$ group may be added all at once or portion wise. In particular for the reagent being a reducing agent, e.g. an ionic hydride donor such as $Na^+[B(CN)H_3]^-$, it is preferred that the reagent is provided in two or three portions.

If the amount of the reagent comprising the $R^6$ group is used all at once, it is preferred for practical reasons that the compound of formula IV is added to the reagent comprising the $R^6$ group.

Similarly, if the amount of the reagent comprising the $R^6$ group is used portion wise, it is preferred that the compound of formula IV is added to the first portion of the reducing agent. Typically, about half of the amount of the reagent comprising the $R^6$ group is used in this context. The mixture is then stirred for a certain reaction time of e.g. 10 to 18 hours, and one or two further portions of the reagent are added later on, so that the total amount of the reagent is finally added to the reaction mixture. The reaction mixture is then again stirred for a certain reaction time of, e.g., 10 to 18 hours, 12 to 24 hours, or 3 to 4 days.

Preferred pH values for the reaction of the compounds of formula IV with the reagent comprising the $R^6$ group, e.g. an ionic hydride donor such as $Na^+[B(CN)H_3]^-$, are in the range of from 4 to 6.

In general, the reaction may be performed in the presence of an acidic catalyst. This is particularly preferred, if the reagent comprising the $R^6$ group is a reducing agent or a nucleophilic reagent. Preferred acid catalysts include HCl in $H_2O$, HCl in MeOH, HCl in dioxane; $H_2SO_4$, $H_3PO_4$ and salts of $H_2SO_4$ and $H_3PO_4$; aromatic sulfonic acids such as toluene sulfonic acid; alkylsulfonic acids, such as methyl sulfonic acid; aromatic carboxylic acids such as benzoic acid; alkylcarboxylic acids such as acetic acid; salts of rare earth metals; and Lewis acids such as $BF_3$, $BF_3 \times OEt_2$, $BF_3 \times SMe_2$, $TiCl_4$, $Ti(OiPr)_4$. Preferred acids catalysts further include aromatic sulfonic acids such as toluene sulfonic acid; alkylsulfonic acids, such as methyl sulfonic acid; aromatic carboxylic acids such as benzoic acid; alkylcarboxylic acids such as acetic acid; haloalkylcarboxylic acids such as trifluoroacetic acid, and mineral acids such as hydrogen chloride or sulfuric acid in methanol. A preferred acid catalyst is acetic acid or HCl in MeOH. Acetic acid is particularly preferred.

The acidic catalyst is preferably used in amounts in the range of from 0.001 to 10 mol, preferably from 1.0 to 5.0 mol, e.g. 1.0 to 2.0 mol or 2.0 to 4.0 mol, per mol of the compound of formula IV. For acetic acid, amounts of 1.0 to 3.0 mol per mol of the compound of formula IV are preferred, and for HCl in MeOH, amounts of 1.0 to 5.0 mol per mol of the compound of formula IV are preferred.

Alternatively or additionally, a metal catalyst may be present in the reaction mixture. Suitable metal catalysts include Cu, Pd, Pt, Ni, Fe, Rh, Ru either as the elements or in the form of a salt, and either pure or on an inert carrier. Suitable catalysts include Rayney-Nickel, Pd/C, Pt/C and the like. Preferred metal catalysts are selected from the group consisting of Rayney-Nickel, Pd/C, Pt/C, Ru/C, Rh/C, and $PtO_2$, in particular from Rayney-Nickel, Pd/C, Pt/C, and $PtO_2$.

The resulting compounds of formula V, which can be obtained according to step (c) of the process of the invention, can be purified by methods known in the art, e.g. by distillation, if esters of formula Va are prepared.

The reaction conditions for step (d) of the process of the invention are as follows.

In step (d), a compound of formula Va or Vb is converted into a compound of formula Vc. Typically, said reaction may be understood as a hydrolysis reaction because an ester or a nitrile is hydrolyzed to give the free acid. However, other conversion reactions of esters or nitriles into the free acids, such as the conversion of tert-butyl esters into the free acids by the addition of trifluoroacetic acid, are also covered by the invention.

If the reaction is a according to step (d) is a hydrolysis reaction, the reaction may be carried out by a process, wherein the compound of formula Va or Vb is reacted with water e.g. in the presence of a base or in the presence of an acid, or by a process, wherein the compound of formula Va or Vb is reacted with a water soluble base, preferably an oxo-base, in an aqueous solvent, or by a process, wherein the compound of formula Va or Vb is reacted with a hydroxide in a protic aqueous or organic solvent. Such hydrolysis reactions can be performed according to procedures known in the art.

It is preferred according to the present invention that step (d) is performed by dissolving a compound of formula Va in a protic solvent, either an aqueous solvent such as water or in a protic organic solvent, a such as a $C_1$-$C_4$-alkanol, e.g. methanol, ethanol or isopropanol, and adding a hydroxide.

Suitable hydroxides include alkali metal hydroxides such as lithium, sodium or potassium hydroxide, and mixtures thereof. Sodium hydroxide is particularly preferred.

It is preferred that sodium hydroxide is used in amounts of from 1 to 10 mol, preferably from 2.0 to 6.0 mol, e.g. 2.0 to 3.0 mol or 5.0 to 6.0 mol, per mol of the compound of formula Va.

Suitable reaction temperatures may vary from 20 to 100° C., e.g. from 20 to 25° C. or from 50 to 100° C.

The reaction times may vary from 1 hour to 2 days, e.g. from 1 to 3 hours or from 12 hours to 24 hours or from 1 to 2 days.

The conversion of compounds of formula Va into compounds of formula Vc can be enhanced, and complete conversion can more easily be ensured, if the alcohol, which is formed upon hydrolysis of the compounds of formula Va, is removed from the reaction mixture, e.g. by distillation.

The conversions of compounds of formula Vb into compounds of formula Vc is advantageously performed in an acidic medium, preferably in the presence of $H_2SO_4$ or in the presence of HCl in MeOH. As intermediate compounds, iminoester compounds are formed, which are then hydrolysed to the desired acids of formula Vc.

The resulting compounds of formula Vc can be purified by methods known in the art, e.g. by crystallization under suitable pH conditions.

The reaction conditions for steps (e) and (f) of the process are as follows.

In step (e), the compound of formula Vc is activated by converting it into the activated acid derivative of formula VI. Suitable peptide coupling reagents, which may be used for introducing the leaving group $X^1$ of the compounds of formula VI starting from compounds of formula V, are described by Han et al. in Tetrahedron 60 (2004) 2447-2467. In this regard, N,N'-bis(2-oxo-3-oxazolidinyl)-phosphinic chloride (BOP-Cl) and O-(7-azabenzotriazol-1-yl)-1,1,3,3-tetramethyluronium hexafluorophosphate (HATU) are preferred according to the present invention.

In addition to the conversion of the compounds of formula Vc into activated acid derivatives of formula VI by means of these peptide coupling reagents, it has also been described in the art how leaving groups such as halogen, $N_3$, p-nitrophenoxy and pentafluorophenoxy can be introduced into the compounds of formula Vc to give the corresponding compounds of formula VI. In this regard, reference is made to WO 2009/027393 and WO 2010/034737.

The compound of formula VI may either be directly converted into a compound of formula VIII or isolated. It is preferred, however, that the compound of formula VI is directly converted into the compound of formula VIII.

The coversion of compounds of formula VI into compounds of formula VIIII by reacting the compounds of formula VI with compounds of formula VIII has already been described in WO 2009/027393 and WO 2010/034737.

EXAMPLES

I. Characterization

The characterization can be done by coupled High Performance Liquid Chromatography/mass spectrometry (HPLC/MS), by NMR or by their melting points.

HPLC/MS: the following methods A), B), C) and D) have been used, and will be referred to further below.
A) Phenomenex Kinetex 1.7 μm XB-C18 100A; 50×2.1 mm; mobile phase: A: water+0.1% trifluoroacetic acid (TFA); B: acetonitrile (MeCN)+0.1% TFA; gradient: 5-100% B in 1.50 minutes; 100% B 0.20 min; flow: 0.8-1.0 mL/min in 1.50 minutes at 60° C. MS-method: ESI positive.
B) The gradient was 10-80% B in 1.15 min with a hold at 90% B for 0.4 min, 80-10% B in 0.01 min, and then hold at 10% B for 0.54 min (1.0 mL/min flow rate). Mobile phase A was 0.0375% TFA in water, mobile phase B was 0.018% TFA in MeCN. Column temperature was 40° C. The column used for the chromatography was a 2.1×30 mm Halo C18 column (2.7 μm particles). MS-method: ESI positive.
C) The gradient was 10-80% B in 1.15 min with a hold at 90% B for 0.4 min, 80-10% B in 0.01 min, and then hold at 10% B for 0.54 min (1.0 mL/min flow rate). Mobile phase A was 0.0375% TFA in water, mobile phase B was 0.018% TFA in MeCN. Column temperature was 40° C. The column used for the chromatography was 2.0×30 mm phenomenex LunaC18 column (3 μm particles). MS-method: ESI positive.
D) The gradient was 5-95% B in 0.7 min, 95-95% B in 0.45 min, 95-5% B in 0.01 min, and then hold at 0% B for 0.44 min (1.5 mL/min flow rate). Mobile phase A was 0.0375% TFA in water, mobile phase B was 0.018% TFA in MeCN. Column temperature was 40° C. The column used for the chromatography was a Chromolith Flash RP-18e 25-2 mm column. MS-method: ESI positive.

$^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

Abbreviations used are: h for hour(s), min for minute(s) and room temperature for 20-25° C.

II. Preparation Examples

Example 1 (Step (a)): 1-cyclohexylpropan-2-one Hydrazone

A mixture of 1-cyclohexylpropan-2-one (10 g), hydrazine monohydrate (4.3 g), barium oxide (2.8 g) and ethanol (100 ml) was refluxed for 14 h. After cooling to room temperature, diethyl ether (120 ml) was added. The mixture was filtered and the filtrate was evaporated to give the crude title compound (9.0 g, ca. 82% yield).

Example 2 (Step (b)): ethyl 2-[[2-(2-cyclohexyl-1-methyl-ethylidene)hydrazino]methylene]-3-oxo-butanoate Crude 1-cyclohexylpropan-2-one hydrazone (9.0 g) in ethanol (20 ml) was added to ethyl 2-(ethoxymethylene)-3-oxo-butanoate (11 g) in ethanol (80 ml) at −20° C. within 40 min. After 30 min, the mixture was stirred at room temperature over night and directly used in the next step.

Example 3 (step (c)): ethyl 1-(2-cyclohexyl-1-methyl-ethyl)-5-methyl-pyrazole-4-carboxylate Acetic acid (4.3 ml) was added to the reaction mixture from step 2. Sodium cyanoborohydride (2.4 g) was added portionwise within 30 min at room temperature. After stirring over night, more acetic acid (2.5 ml) and more sodium cyanoborohydride (1.1 g) was added. After stirring over night, again more acetic acid (3 ml) and more sodium cyanoborohydride (2.0 g) was added and the mixture was stirred at 50° C. for 3 h and then concentrated in vacuo. Water (80 ml) was added to the residue, and the aqueous phase was extracted three times with tert-butyl methyl ether. The combined organic extracts were washed with water, dried over sodium sulfate and concentrated in vacuo to give the crude title compound (17 g, ca. 80% purity, ca. 84% yield over 2 steps).

Example 4 (step (d)): 1-(2-cyclohexyl-1-methyl-ethyl)-5-methyl-pyrazole-4-carboxylic Acid A mixture of crude ethyl 1-(2-cyclohexyl-1-methyl-ethyl)-5-methyl-pyrazole-4-carboxylate (17 g, ca. 80% purity), aqueous sodium hydroxide solution (2 M, 56 ml) and ethanol (150 ml) was stirred at room temperature for 2 d and then concentrated in vacuo. Water was added to the residue, and the aqueous phase was extracted three times with tert-butyl methyl ether. Concentrated hydrochloric acid was added under ice cooling to adjust the pH to ca. 4. The precipitate was filtered off, washed with water, triturated with tert-butyl methyl ether and dried in vacuo to give the title compound (5.3 g, ca. 43% yield, 30% yield over all 4 steps). $^1$H-NMR (d$_6$-DMSO): 7.76 (s, 1H), 4.46 (m, 1H), 2.49 (s, 3H), 1.84 (m, 1H), 1.70 (d, 11.3 Hz, 1H), 1.66-1.43 (m, 5H), 1.31 (d, 6.6 Hz, 3H), 1.09 (m, 3H), 0.89 (m, 3H).

In accordance with the above 4-step reaction procedure for preparing compounds of formula V.c by performing

- step (a) to provide compounds of formula II (Example 1),
- step (b) to provide compounds of formula IV (Example 2),
- step (c) to provide compounds of formula Va (Example 3), and
- step (d) to provide compounds of formula Vc (Example 4), a variety of compounds of formula V.a and V.c have been prepared. The relevant substituents of the compounds of formula V.c and its precursors are listed in the following table D. Furthermore, the yields and analytical HPLC/MS data are provided. The relevant reaction scheme is again depicted below.

Step (a):

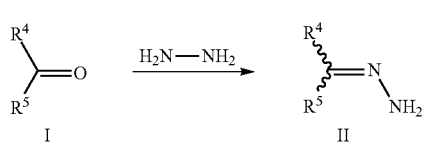

Step (b):

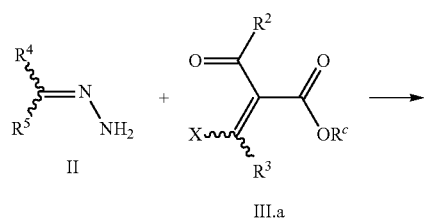

Step (c):

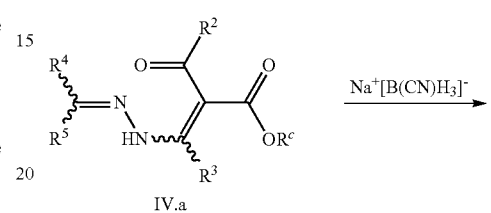

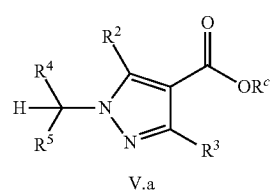

Step (d):

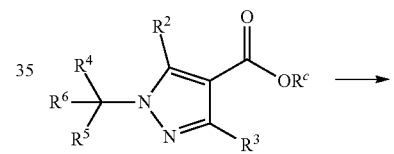

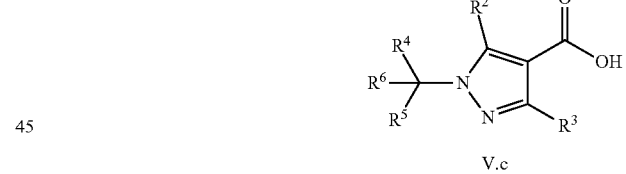

TABLE D

| # | R$^5$ | R$^4$ | R$^c$ in V.a | R$^2$ | R$^3$ | X in III.a | yield I→V.a [%] | V.a RT [min] | Method | V.a m/z [MH]$^+$ | V.c RT [min] | Method | V.c m/z [MH]$^+$ |
|---|-------|-------|--------------|-------|-------|------------|-----------------|--------------|--------|------------------|--------------|--------|------------------|
| 1 | CH$_3$ | CH(CH$_3$)OH | CH$_2$CH$_3$ | CH$_3$ | H | OCH$_2$CH$_3$ | 55 | 0.846 | A | 227.1 | 0.590 | A | 199.2 |
| 2 | CH$_3$ | CH$_2$CH$_2$OH | CH$_2$CH$_3$ | CH$_3$ | H | OCH$_2$CH$_3$ | 12 | 0.870 | A | 227.2 | n/a | n/a | n/a |
| 3 | CH$_3$ | 1-CN-cC$_3$H$_4$ | CH$_2$CH$_3$ | CH$_3$ | H | OCH$_2$CH$_3$ | n/a | 0.961 | A | 248.3 | n/a | n/a | n/a |
| 4 | CH$_3$ | CH(CH$_3$)SCH$_2$CH(CH$_3$)$_2$ | CH$_2$CH$_3$ | CH$_3$ | H | OCH$_2$CH$_3$ | 18 | 1.332 | A | 298.8 | n/a | n/a | n/a |
| 5 | CH$_3$ | 2-furyl | CH$_2$CH$_3$ | CH$_3$ | H | OCH$_2$CH$_3$ | 5 | 1.064 | A | 249.5 | n/a | n/a | n/a |
| 6 | CH$_3$ | 2-furyl | CH$_2$CH$_3$ | CF$_3$ | H | OCH$_2$CH$_3$ | 3 | 1.091 | A | 302.8 | n/a | n/a | n/a |
| 7 |  | CH$_2$CH$_2$C(F$_2$)CH$_2$CH$_2$ | CH$_2$CH$_3$ | CH$_3$ | H | OCH$_2$CH$_3$ | 85 | 1.116 | A | 273.5 | 0.837 | A | 245.1 |
| 8 |  | CH$_2$SCH$_2$CH$_2$CH(CN) | CH$_2$CH$_3$ | CH$_3$ | H | OCH$_2$CH$_3$ | 35 | 0.894 | A | 280.0 | n/a | n/a | n/a |
| 9 | CH$_3$ | CH(OCH$_3$)$_2$ | CH$_2$CH$_3$ | CH$_3$ | H | OCH$_2$CH$_3$ | 85 | 1.002 | A | 257.5 | 0.709 | A | 228.8 |
| 10 |  | CH$_2$CH$_2$CH(OCH$_2$C$_6$H$_5$) | CH$_2$CH$_3$ | CH$_3$ | H | OCH$_2$CH$_3$ | 16 | 1.189 1.225$^a$ | A | 314.8 | n/a | n/a | n/a |
| 11 | CH$_3$ | CH$_2$CH$_2$CHC(CH$_3$)$_2$ | CH$_2$CH$_3$ | CH$_3$ | H | OCH$_2$CH$_3$ | 86 | 1.276 | A | 265.3 | 1.061 | A | 237.4 |
| 12 | CH$_3$ | 1-C(O)NH$_2$-cC$_3$H$_4$ | CH$_2$CH$_3$ | CH$_3$ | H | OCH$_2$CH$_3$ | 24 | 0.841 | A | 265.8 | 0.582 | A | 238.4 |
| 13 | CH$_3$ | CH$_2$cC$_6$H$_{11}$ | CH$_2$CH$_3$ | CH$_3$ | H | OCH$_2$CH$_3$ | 69 | 1.381 | A | 279.2 | 1.129 | A | 251.2 |
| 14 | CH$_3$ | CH$_2$C(CH$_3$)$_3$ | CH$_2$CH$_3$ | CH$_3$ | H | OCH$_2$CH$_3$ | 96 | 1.310 | A | 253.2 | 1.038 | A | 225.2 |

TABLE D-continued

| # | $R^5$ | $R^4$ | $R^c$ in V.a | $R^2$ | $R^3$ | X in III.a | yield I→V.a [%] | V.a RT [min] | Method | V.a m/z [MH]$^+$ | V.c RT [min] | Method | V.c m/z [MH]$^+$ |
|---|---|---|---|---|---|---|---|---|---|---|---|---|---|
| 15 | CH$_3$ | CH(CH$_2$CH$_3$)$_2$ | CH$_2$CH$_3$ | CH$_3$ | H | OCH$_2$CH$_3$ | n/a | 1.315 | A | 253.2 | 1.037 | A | 225.2 |
| 16 |  | CH$_2$CH$_2$CH$_2$CH$_2$CH(CF$_3$) | CH$_2$CH$_3$ | CH$_3$ | H | OCH$_2$CH$_3$ | 38 | 1.284 | A | 305.1 | 1.040 | A | 277.1 |
| 17 | CH$_3$ | CH(CH$_3$)CH$_2$CH$_2$CH$_3$ | CH$_2$CH$_3$ | CH$_3$ | H | OCH$_2$CH$_3$ | 77 | 1.310 | A | 253.2 | 1.046 | A | 225.2 |
| 18 | CH$_3$ | CH(CH$_3$)CH$_2$OH | CH$_2$CH$_3$ | CH$_3$ | H | OCH$_2$CH$_3$ | 88 | 0.889 | A | 241.5 | 0.614 | A | 213.4 |
| 19 | CH$_3$ | CH(CH$_3$)$_2$ | CH$_2$CH$_3$ | CH$_3$ | H | OCH$_2$CH$_3$ | 64 | 1.510 | A | 225.1 | 0.890 | A | 197.2 |
| 20 | CH$_3$ | [cyclopropyl-C(O)O-tBu structure] | CH$_2$CH$_3$ | CH$_3$ | H | OCH$_2$CH$_3$ | 42 | 1.542 / 1.637$^a$ | C | 349.2 | n/a | n/a | n/a |
| 21 | CH$_3$ | [spiro-cyclopropyl-CH$_2$OCH$_3$ structure] | CH$_2$CH$_3$ | CH$_3$ | H | N(CH$_3$)$_2$ | 35 | 1.385 / 1.431$^a$ | C | 293.2 | 1.111 / 1.150$^a$ | B | 265.2 |
| 22 | CH$_3$ | [cyclopropyl-CH$_2$O-(4-methoxyphenyl) structure] | CH$_2$CH$_3$ | CH$_3$ | H | N(CH$_3$)$_2$ | 58 | 1.579 | C | 375.1 | n/a | n/a | n/a |
| 23 | CH$_3$ | C(CH$_3$)$_2$OH | CH$_2$CH$_3$ | CH$_3$ | H | N(CH$_3$)$_2$ | 22 | 1.308 | C | 255.2 | 0.965 | B | 227.2 |
| 24 | CH$_3$ | 2-Br-2-CH$_3$-cC$_3$H$_3$ | CH$_2$CH$_3$ | CH$_3$ | H | OCH$_2$CH$_3$ | 39 | 0.885 / 0.910$^a$ | D | 315.1 | n/a | n/a | n/a |
| 25 |  | CH$_2$OC(CH$_3$)$_2$OCH$_2$ | CH$_2$CH$_3$ | CH$_3$ | H | N(CH$_3$)$_2$ | 35 | 1.328 | B | 269.2 | 1.022 | B | 241.1 |
| 26 | CH$_3$ | C(CH$_3$)$_2$SCH$_3$ | CH$_2$CH$_3$ | CH$_3$ | H | N(CH$_3$)$_2$ | 33 | 1.328 | C | 271.2 | 1.253 | B | 243.2 |
| 27 | CH$_3$ | 1-C(O)OC(CH$_3$)$_3$-cC$_3$H$_4$ | CH$_2$CH$_3$ | CH$_3$ | H | N(CH$_3$)$_2$ | 39 | 0.934 | D | 323.2 | n/a | n/a | n/a |
| 28 | cC$_3$H$_5$ | 1-CH$_2$OCH$_2$C$_6$H$_5$-cC$_3$H$_4$ | CH$_2$CH$_3$ | CH$_3$ | H | N(CH$_3$)$_2$ | 44 | 0.947 | D | 369.2 | n/a | n/a | n/a |
| 29 | cC$_3$H$_5$ | C(CH$_3$)$_2$CH$_2$OCH$_2$C$_6$H$_5$ | CH$_2$CH$_3$ | CH$_3$ | H | N(CH$_3$)$_2$ | 66 | 0.990 | D | 371.2 | n/a | n/a | n/a |
| 30 | CH$_3$ | [dimethyl-dioxane structure] | CH$_2$CH$_3$ | CH$_3$ | H | N(CH$_3$)$_2$ | 28 | 0.835 | D | 311.2 | 1.077 | B | 283.3 |
| 31 | CH$_3$ | CH$_2$OH | C(CH$_3$)$_3$ | CH$_3$ | H | N(CH$_3$)$_2$ | 41 | 0.697 | D | 241.1 | n/a | n/a | n/a |
| 32 | CH$_3$ | C(CH$_3$)(CO$_2$CH$_2$CH$_3$)(CH$_2$)$_3$NHCO$_2$C(CH$_3$)$_3$ | C(CH$_3$)$_3$ | CH$_3$ | H | N(CH$_3$)$_2$ | 31 | 1.063 | D | 468.4 | n/a | n/a | n/a |
| 33 | CH$_3$ | CH(CH$_3$)OH | CH$_2$CH$_3$ | CH$_3$ | H | N(CH$_3$)$_2$ | 46 | 1.002 | B | 227.2 | n/a | n/a | n/a |
| 34 | CH$_3$ | C(CH$_3$)$_2$OH | C(CH$_3$)$_3$ | CH$_3$ | H | N(CH$_3$)$_2$ | 74 | 0.784 | D | 269.2 | n/a | n/a | n/a |
| 35 | CH$_3$ | CH(CH$_3$)OH | C(CH$_3$)$_3$ | CH$_3$ | H | N(CH$_3$)$_2$ | 69 | 0.757 | D | 255.2 | n/a | n/a | n/a |

$^a$mixture of two diastereoisomers

The reaction procedure of Examples 1 to 4 refers compounds with a substitution pattern according to entry 13 of table D.

The compounds according to the remaining entries were either prepared analogously or according to the reaction conditions exemplified below referring to certain entries of the above table D. The reaction conditions exemplified below are not limited to the entries of table D to which they refer, but were also suitable for the preparation of other compounds disclosed in table D.

It is noted that steps (a) and (b), steps (b) and (c) were also performed in a one-pot reaction in the preparation of certain compounds.

The following reaction conditions for steps (a), (b), (c) and (d) are relevant for the preparation of the compounds listed above (abbreviations: rt=room temperature, i.e. 20 to 25° C., rfx=reflux temperature, i.e. boiling point of the solvent; MeOH=methanol; EtOH=ethanol; AcOH=acetic acid; MTBE=methyltertbutyl ether; eq=equivalent).

Step (a):

| # | corresponds to entry x in table D | conditions |
|---|---|---|
| (a)-1 | 7 | $N_2H_4 \times H_2O$ (1.2 eq), BaO (0.02 eq), I (2 g/1 eq), MeOH (2 ml), rt, rfx overnight |
| (a)-2 | 13 | $N_2H_4 \times H_2O$ (1.2 eq), BaO (0.26 eq), EtOH (50 ml), I (10 g/1 eq), rt, rfx 14 h |
| (a)-3 | 1 | I (10 g/1 eq), BaO (0.26 eq), EtOH (80 ml), 10-20° C., $N_2H_4 \times H_2O$ (1.2 eq), rt 1 h, 80° C. overnight |
| (a)-4 | 12 | $N_2H_4 \times H_2O$ (1 eq), AcOH (0.17 eq), I (262 g/1 eq), EtOH (2200 ml), rt 3 days |
| (a)-5 | 8 | $N_2H_4 \times H_2O$ (10 g/1.2 eq), EtOH (100 ml), I (262 g/1 eq), EtOH (100 ml), rt overnight |
| (a)-6 | 10 | I (3.6 g/1 eq), BaO (0.26 eq), EtOH (100 ml), rt, $N_2H_4 \times H_2O$ (1.2 eq), rt 3 days |
| (a)-7 | 19 | MeOH (3.25 eq), $N_2H_4 \times H_2O$ (1.28 eq), BaO (0.02 eq), 33-47° C., I (2415 g/1 eq), 25° C. overnight |

Steps (a)+(b):

| # | corresponds to entry x in table D | conditions |
|---|---|---|
| (a) + (b)-1 | 3 | $N_2H_4 \times H_2O$ (1 eq), AcOH (0.1 eq), I (1.376 g/1 eq), EtOH (15 ml), rt overnight; III.a (6.15 g/1.2 eq), rt overnight |
| (a) + (b)-2 | 14 | $N_2H_4 \times H_2O$ (1.2 eq), BaO (0.26 eq), EtOH (50 ml), rt, I (5 g/1 eq), rfx overnight; III.a (1 eq), EtOH (50 ml), −20° C., II (5.5 g/1 eq), EtOH (20 ml), 30 min −20° C., rt overnight |

Step (b):

| # | corresponds to entry x in table D | conditions |
|---|---|---|
| (b)-1 | 9 | III.a (1.1 eq), EtOH (60 ml), rt, II (12.5 g/1 eq), EtOH (40 ml), rt-37° C., rt overnight |
| (b)-2 | 1 | III.a (16.96 g/1 eq), EtOH (70 ml), 0-10° C., II (9.3 g/1 eq), EtOH (30 ml), rt overnight |
| (b)-3 | 12 | III.a (450 g/1.51 eq), EtOH (3000 ml), AcOH (8.5 ml), II (221 g/1 eq), rt overnight |
| (b)-4 | 19 | III.a (609 g/1 eq), II (3818 g/1.09 eq) in MTBE (9.36% solution), 3 h rt-33° C. overnight |

Step (b)+(c):

| # | corresponds to entry x in table D | conditions |
|---|---|---|
| (b) + (c)-1 | 16 | III.a (0.83 g/1 eq), EtOH (15 ml), −20° C., II (0.8 g/1 eq), EtOH (5 ml), −20° C. 30 min, rt over 3 days, AcOH (0.34 g/1.3 eq), 0-5° C. NaB(CN)H$_3$ (0.28 g/1 eq), rt overnight, NaB(CN)H$_3$ (0.25 g), AcOH (0.4 ml), 6 h 40° C., rt overnight, 20 ml isopropanol, AcOH (1.3 eq), rt, NaB(CN)H$_3$ (1 eq), rt overnight, NaB(CN)H$_3$ (0.15 g), AcOH (0.2 ml), 6 h 40° C., rt overnight, NaB(CN)H$_3$ (0.1 g), 6 h 40° C., rt overnight |
| (b) + (c)-2 | 17 | III.a (7.12 g/1 eq), EtOH (50 ml), rt, II (4.9 g/1 eq), EtOH (20 ml), rt overnight, AcOH (2.61 g/1.2 eq), rt, NaB(CN)H$_3$ (1.67 g/0.7 eq), rt over 3 days, isopropanol (100 ml), 10° C., AcOH (1.2 eq), 10° C., NaB(CN)H$_3$ (0.65 eq), rt overnight, NaB(CN)H$_3$ (0.5 g), AcOH (0.5 ml), 6 h 40° C., rt overnight |
| (b) + (c)-3 | 1 | III.a (16.96 g/1 eq), EtOH (70 ml), 0-10° C., II (9.3 g/1 eq), EtOH (30 ml), rt overnight, EtOH (120 ml), AcOH (1.3 eq), 10-17° C., NaB(CN)H$_3$ (1 eq), rt 3 days |
| (b) + (c)-4 | 8 | III.a (7.55 g/1 eq), EtOH (50 ml), −20° C., II (5.2 g/1 eq), EtOH (20 ml), −20° C. 30 min, rt over 3 days, MeOH (100 ml), AcOH (1.3 eq), 0-5° C., NaB(CN)H$_3$ (2.51 g/1 eq), rt overnight, NaB(CN)H$_3$ (1.2 g), AcOH (1.5 ml), 6 h 40° C., rt overnight, NaB(CN)H$_3$ (1.5 g), AcOH (2 ml), 6 h 40° C., rt overnight, isopropanol (100 ml), NaB(CN)H$_3$ (1 eq), rt overnight |

-continued

| # | corresponds to entry x in table D | conditions |
|---|---|---|
| (b) + (c)-5 | 15 | III.a (10.86 g/1 eq), EtOH (80 ml), −20° C., II (9 g/1 eq), EtOH (20 ml), −20° C. 20 min, rt overnight, AcOH (4.53 g/1.3 eq), NaB(CN)H₃ (2.37 g/0.65 eq), rt overnight, 3 h 50° C., NaB(CN)H₃ (1.1 g), AcOH (2.5 ml), rt overnight, NaB(CN)H₃ (2 g), AcOH (3 ml), 3 h 50° C. |
| (b) + (c)-6 | 13 | III.a (10.86 g/1 eq), EtOH (80 ml), −20° C., II (1 eq), EtOH (20 ml), −20° C. 30 min, rt overnight, AcOH (4.53 g/1.3 eq), rt, NaB(CN)H₃ (2.37 g/0.65 eq), rt overnight, 3 h 50° C., NaB(CN)H₃ (1.1 g), AcOH (2.5 ml), 3 h 50° C., rt overnight, NaB(CN)H₃ (2 g), AcOH (3 ml), 3 h 50° C. |
| (b) + (c)-7 | 11 | III.a (13.01 g/1 eq), EtOH (60 ml), rt, II (1 eq), EtOH (20 ml), rt overnight, AcOH (5.45 g/3.64 eq), 0-5° C., NaB(CN)H₃ (1.02 g/0.65 eq), rt 3 days |

Step (c):

| # | corresponds to entry x in table D | conditions |
|---|---|---|
| (c)-1 | 9 | IV.a (27.9 g/1 eq), isopropanol (100 ml), rt, NaB(CN)H₃ (0.6 eq), AcOH (1.2 eq), rt overnight, NaB(CN)H₃ (0.6 eq), rt overnight |
| (c)-2 | 10 | IV.a (1 g/1 eq), EtOH (20 ml), rt, AcOH (2.4 eq), NaB(CN)H₃ (1.2 eq), rt over 3 days |
| (c)-3 | 17 | IV.a (9.5 g/1 eq), isopropanol (100 ml), 10° C., NaB(CN)H₃ (0.65 eq), AcOH (1.2 eq) rt overnight, NaB(CN)H₃ (0.5 g), AcOH (0.5 ml), 6 h 40° C., rt overnight |
| (c)-4 | 18 | IV.a (18 g/1 eq), MeOH (120 ml), AcOH (1.2 eq), rt, NaB(CN)H₃ (1 eq), rt overnight |
| (c)-5 | 18 | IV.a (15.7 g/1 eq), isopropanol (100 ml), AcOH (1.25 eq), rt, NaB(CN)H₃ (1 eq), rt over 3 days, AcOH (2.5 ml), NaB(CN)H₃ (1 g), 4 h 40° C., rt overnight |
| (c)-6 | 7 | IV.a (1.9 g/1 eq), 0-5° C., NaB(CN)H₃ (0.65 eq), AcOH (1.3 eq), rt overnight, NaB(CN)H₃ (0.3 eq), rt over 3 days |
| (c)-7 | 12 | IV.a (100 g/1 eq), MeOH (1400 ml), rt, NaB(CN)H₃ (2.19 eq), HCl (1N in MeOH, 1000 ml), 40° C., rt overnight |
| (c)-8 | 19 | IV.a (889 g/1 eq), MeOH (3000 ml), AcOH (400 g), rt-30° C., NaB(CN)H₃ (1.09 eq), rt overnight |

Step (d):

| # | corresponds to entry x in table D | conditions |
|---|---|---|
| (d)-1 | 13 | V.a (17 g/1 eq), EtOH (150 ml), NaOH (2M in H₂O, 4.49 g/2.3 eq), rt overnight, NaOH (2M in H₂O, 25 ml), rt 24 h |
| (d)-2 | 1 | V.a (15.3 g/1 eq), EtOH (80 ml), NaOH (2.5 eq), H₂O (40 ml), rt overnight |
| (d)-3 | 12 | V.a (120 g/1 eq), MeOH (1400 ml), NaOH (5.96 eq), H₂O (58.54 eq), rt overnight |
| (d)-4 | 7 | V.a (2.15 g/1 eq), EtOH 30 ml), NaOH(2M in H₂O, 2.5 eq), 45° C. 2.5 h |
| (d)-5 | 19 | NaOH (10% in H₂O, 3 eq), rt, V.a (724 g/1 eq), 1 h 95° C. |

The invention claimed is:

1. A compound of formula V or a salt, stereoisomer, tautomer or N-oxide thereof

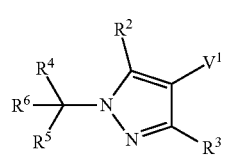
(V)

wherein
$R^2$ is $CH_3$, $R^3$ is H, $R^4$ is $CH(CH_3)_2$, $R^5$ is $CH_3$ and $R^6$ is H; or
$R^2$ is $CH_3$, $R^3$ is H, $R^4$ is $CHFCH_3$, $R^5$ is $CH_3$ and $R^6$ is H; or
$R^2$ is $CH_3$, $R^3$ is H, $R^4$ is 1-CN-c$C_3H_4$, $R^5$ is $CH_3$ and $R^6$ is H; or
$R^2$ is $CH_3$, $R^3$ is H, $R^4$ is 1-C(O)NH$_2$-c$C_3H_4$, $R^5$ is $CH_3$ and $R^6$ is H; or
$R^2$ is $CH_3$, $R^3$ is H, $R^4$ and $R^5$ together are $CH_2CH_2CF_2CH_2CH_2$, and $R^6$ is H;
wherein
$R^1$ is CN or COOR$^c$; R$^c$ is H, $C_1$-$C_4$-alkyl or aryl-$C_1$-$C_4$-alkyl, or wherein R$^c$ together with the C(O)O group forms a salt [C(O)O]⁻NR₄⁺, [C(O)O]⁻M_a⁺ or [C(O)O]⁻½M_ea²⁺, wherein M_a is an alkali metal and M_ea is an alkaline earth metal.

2. The compound of claim 1, wherein said compound has formula Va or a salt, stereoisomer, tautomer or N-oxide thereof

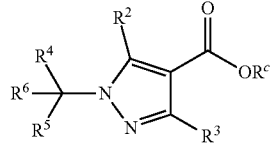

(Va)

wherein
$R^2$ is $CH_3$, $R^3$ is H, $R^4$ is $CH(CH_3)_2$, $R^5$ is $CH_3$ and $R^6$ is H; or
$R^2$ is $CH_3$, $R^3$ is H, $R^4$ is $CHFCH_3$, $R^5$ is $CH_3$ and $R^6$ is H; or
$R^2$ is $CH_3$, $R^3$ is H, $R^4$ is 1-CN-$cC_3H_4$, $R^5$ is $CH_3$ and $R^6$ is H; or
$R^2$ is $CH_3$, $R^3$ is H, $R^4$ is 1-C(O)NH₂-$cC_3H_4$, $R^5$ is $CH_3$ and $R^6$ is H; or
$R^2$ is $CH_3$, $R^3$ is H, $R^4$ and $R^5$ together are $CH_2CH_2CF_2CH_2CH_2$, and $R^6$ is H;
and wherein
$R^c$ is $C_1$-$C_4$-alkyl or aryl-$C_1$-$C_4$-alkyl, or wherein $R^c$ together with the C(O)O group forms a salt [C(O)O]⁻NR₄⁺, [C(O)O]⁻M_a⁺ or [C(O)O]⁻½M_ea²⁺, wherein M_a is an alkali metal and M_ea is an alkaline earth metal.

3. The compound of claim 1, wherein said compound has formula Vc or a salt, stereoisomer, tautomer or N-oxide thereof

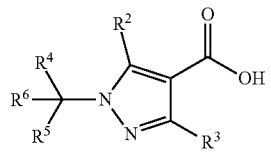

(Vc)

wherein
$R^2$ is $CH_3$, $R^3$ is H, $R^4$ is $CH(CH_3)_2$, $R^5$ is $CH_3$ and $R^6$ is H; or
$R^2$ is $CH_3$, $R^3$ is H, $R^4$ is $CHFCH_3$, $R^5$ is $CH_3$ and $R^6$ is H; or
$R^2$ is $CH_3$, $R^3$ is H, $R^4$ is 1-CN-$cC_3H_4$, $R^5$ is $CH_3$ and $R^6$ is H; or $R^2$ is $CH_3$, $R^3$ is H, $R^4$ is 1-C(O)NH₂-$cC_3H_4$, $R^5$ is $CH_3$ and $R^6$ is H; or
$R^2$ is $CH_3$, $R^3$ is H, $R^4$ and $R^5$ together are $CH_2CH_2CF_2CH_2CH_2$, and $R^6$ is H.

4. The compound of claim 1, wherein said compound has formula Vb or a salt, stereoisomer, tautomer or N-oxide thereof

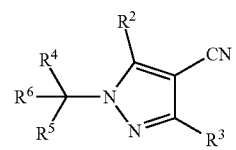

(Vb)

wherein
$R^2$ is $CH_3$, $R^3$ is H, $R^4$ is $CH(CH_3)_2$, $R^5$ is $CH_3$ and $R^6$ is H; or
$R^2$ is $CH_3$, $R^3$ is H, $R^4$ is $CHFCH_3$, $R^5$ is $CH_3$ and $R^6$ is H; or
$R^2$ is $CH_3$, $R^3$ is H, $R^4$ is 1-CN-$cC_3H_4$, $R^5$ is $CH_3$ and $R^6$ is H; or
$R^2$ is $CH_3$, $R^3$ is H, $R^4$ is 1-C(O)NH₂-$cC_3H_4$, $R^5$ is $CH_3$ and $R^6$ is H; or
$R^2$ is $CH_3$, $R^3$ is H, $R^4$ and $R^5$ together are $CH_2CH_2CF_2CH_2CH_2$, and $R^6$ is H.

5. A compound of formula IV or a salt, stereoisomer, tautomer or N-oxide thereof

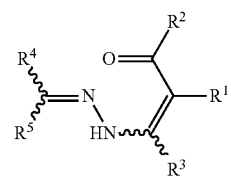

(IV)

wherein
$R^1$ is CN, C(O)OCH₃, C(O)OCH₂CH₃, C(O)OC(CH₃)₃, C(O)OCH₂C₆H₅, or COOH;
$R^2$ is $CH_3$, $R^3$ is H, and
$R^4$ is $CH(CH_3)_2$, and $R^5$ is $CH_3$; or
$R^4$ is $CHFCH_3$, and $R^5$ is $CH_3$; or
$R^4$ is 1-CN-$cC_3H_4$, and $R^5$ is $CH_3$; or
$R^4$ is 1-C(O)NH₂-$cC_3H_4$, and $R^5$ is $CH_3$; or
$R^4$ and $R^5$ together are $CH_2CH_2CF_2CH_2CH_2$.

* * * * *